US008674114B2

(12) United States Patent
Kawakami et al.

(10) Patent No.: US 8,674,114 B2
(45) Date of Patent: Mar. 18, 2014

(54) CARBAZOLE COMPOUND, LIGHT-EMITTING ELEMENT MATERIAL, AND ORGANIC SEMICONDUCTOR MATERIAL

(75) Inventors: Sachiko Kawakami, Kanagawa (JP); Kaori Ogita, Kanagawa (JP); Nobuharu Ohsawa, Tochigi (JP); Hiromi Seo, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/469,619

(22) Filed: May 11, 2012

(65) Prior Publication Data

US 2012/0289708 A1 Nov. 15, 2012

(30) Foreign Application Priority Data

May 13, 2011 (JP) ................. 2011-108093

(51) Int. Cl.
*C07D 409/14* (2006.01)
(52) U.S. Cl.
USPC .......................................... 548/440
(58) Field of Classification Search
None
See application file for complete search history.

(56) References Cited

U.S. PATENT DOCUMENTS

2009/0015140 A1   1/2009   Kawakami et al.
2009/0302745 A1*  12/2009  Otsu et al. ............... 313/504
2010/0069647 A1   3/2010   Suzuki et al.
2012/0071668 A1   3/2012   Suzuki et al.
2012/0074390 A1   3/2012   Seo et al.
2012/0091887 A1   4/2012   Osaka et al.
2012/0133274 A1   5/2012   Kawakami et al.

FOREIGN PATENT DOCUMENTS

JP      2007-15933        1/2007
WO   WO2012033108    *   3/2012

OTHER PUBLICATIONS

Chen et al., Single-crystalline orthorhombic molybdenum oxide nanobelts: synthesis and photocatalytic properties. CrystEngComm. 2010, 12, 3740-3747.*
Goldsmith et al., "C-H Bond Activation by a Ferric Methoxide Complex: Modeling the Rate-Determining Step in the Mechanism of Lipoxygenase", J. Am. Chem. Soc., vol. 124 (1), 2002, pp. 83-96.
Onishi et al., "High Molecular EL Materials—Development of Light-Emitting High Molecular Compounds: A Method of Measuring an Energy Level", Kyoritsu Shuppan, Dec. 25, 2004, pp. 64-67 (with English translation), (English translation only).

* cited by examiner

*Primary Examiner* — Michael Barker
*Assistant Examiner* — Po-Chih Chen
(74) *Attorney, Agent, or Firm* — Husch Blackwell LLP

(57) ABSTRACT

A novel carbazole compound that can be used for a transport layer, a host material, or a light-emitting material in a light-emitting element. In the carbazole compound, two carbazole skeletons each include carbazole, the 3-position of which is bonded to the 4-position of a dibenzofuran skeleton or a dibenzothiophene skeleton and these two carbazole skeletons are linked via benzene or biphenyl. The carbazole compound has an excellent carrier-transport property and a wide energy gap and can be suitably used for a material in a light-emitting element or for an organic semiconductor material.

15 Claims, 35 Drawing Sheets

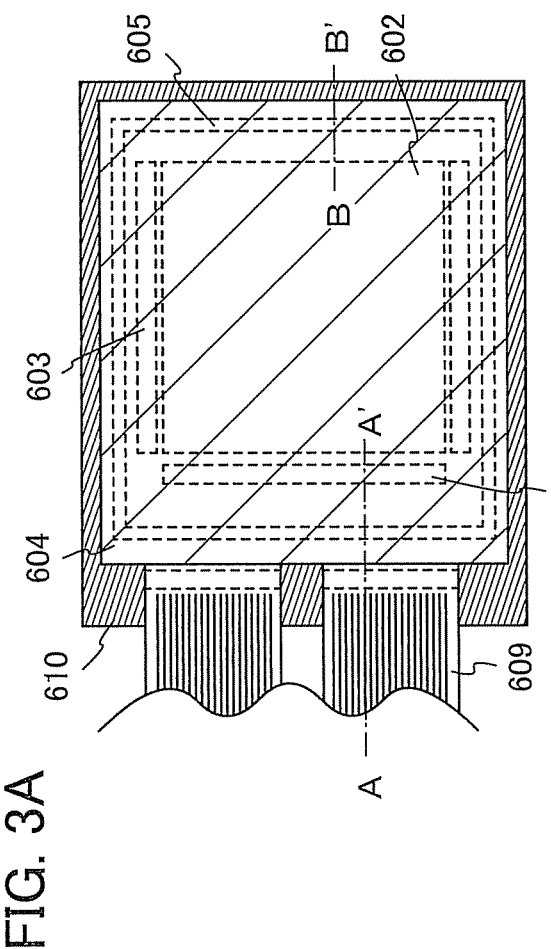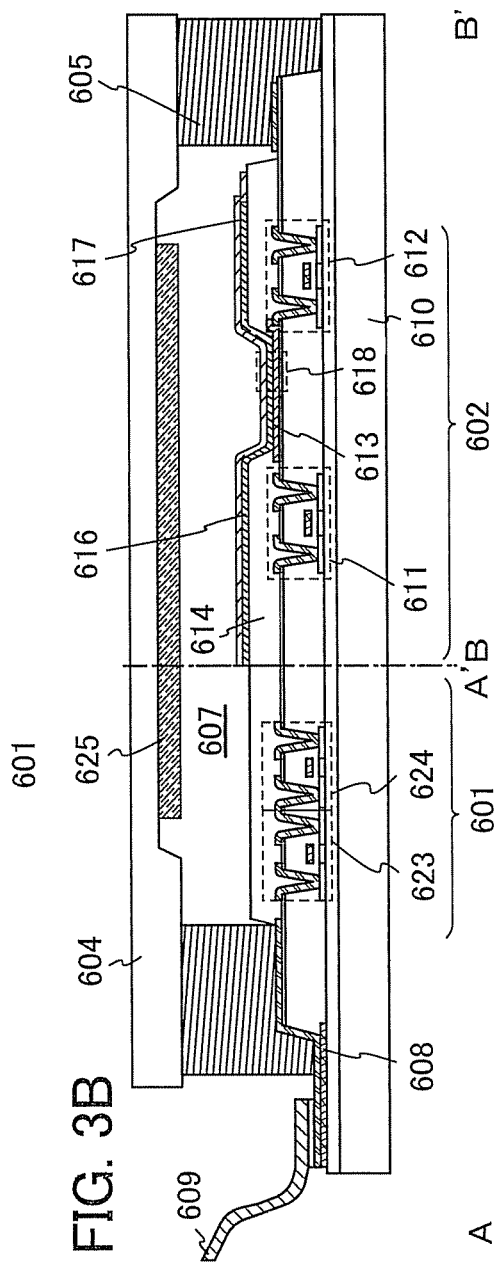
FIG. 3A
FIG. 3B

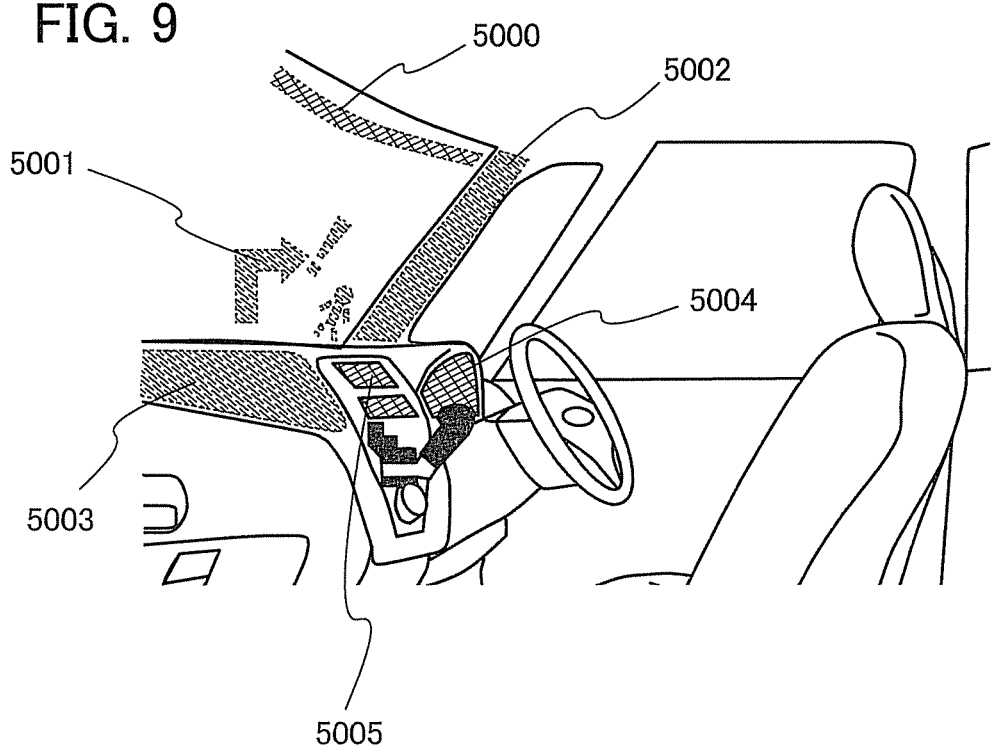

CARBAZOLE COMPOUND, LIGHT-EMITTING ELEMENT MATERIAL, AND ORGANIC SEMICONDUCTOR MATERIAL

BACKGROUND OF THE INVENTION

1. Field of the Invention

The present invention relates to a carbazole compound that can be used for a light-emitting element material. The present invention further relates to a light-emitting element material and an organic semiconductor material each using the carbazole compound.

2. Description of the Related Art

As next generation lighting devices or display devices, display devices using light-emitting elements (organic EL elements) in which organic compounds are used for light-emitting substances have been developed at an accelerated pace because such devices have advantages such as thinness, lightweightness, high speed response to input signals, and low power consumption.

In an organic EL element, voltage application between electrodes, between which a light-emitting layer is provided, causes recombination of electrons and holes injected from the electrodes, which brings a light-emitting substance into an excited state, and the return from the excited state to the ground state is accompanied by light emission. Since the wavelength of light emitted from a light-emitting substance is peculiar to the light-emitting substance, use of different types of organic compounds for light-emitting substances makes it possible to provide light-emitting elements which exhibit various wavelengths, i.e., various colors.

In the case of display devices which are expected to display images, such as displays, at least three-color light, i.e., red light, green light, and blue light are necessary for reproduction of full-color images. Further, in application to lighting devices, light having wavelength components evenly spreading in the visible light region is ideal for obtaining a high color rendering property, but actually, light obtained by mixing two or more kinds of light having different wavelengths is often used for lighting application. Note that it is known that a mixture of three-color light, i.e., red light, green light, and blue light can produce white light having a high color rendering property.

Light emitted from a light-emitting substance is peculiar to the substance, as described above. However, important performances as a light-emitting element, such as lifetime, power consumption, and even emission efficiency, are not only dependent on the light-emitting substance but also greatly dependent on layers other than the light-emitting layer, an element structure, properties of an emission center substance and a host material, compatibility between them, carrier balance, and the like. Therefore, it is true that many kinds of light-emitting element materials are necessary for a growth in this field. For the above-described reasons, light-emitting element materials with a variety of molecular structures have been proposed (e.g., see Patent Document 1).

As is generally known, the generation ratio of a singlet excited state to a triplet excited state in a light-emitting element using electroluminescence is 1:3. Therefore, a light-emitting element in which a phosphorescent material capable of converting the triplet excited state to light emission is used as an emission center substance can theoretically realize higher emission efficiency than a light-emitting element in which a fluorescent material capable of converting the singlet excited state to light emission is used as an emission center substance.

However, since the triplet excited state of a substance is at a lower energy level than the singlet excited state of the substance, a substance that emits phosphorescence has a larger energy gap than a substance that emits fluorescence when the emissions are at the same wavelength.

In order that excitation energy can be efficiently converted to light emission from an emission center substance, a substance having a larger energy gap or higher triplet excitation energy (energy difference between a triplet excited state and a singlet ground state) than the emission center substance is used to serve as a host material in a host-guest type light-emitting layer or to be contained in each transport layer in contact with a light-emitting layer.

Therefore, a host material and a carrier-transport material each having a further larger energy gap are necessary in order that fluorescence having a shorter wavelength than that of blue light or phosphorescence having a shorter wavelength than that of green light be efficiently obtained. There are however not many variations of materials that have a sufficiently large energy gap in addition to good characteristics as a light-emitting element material, and as described above, the performance of a light-emitting element depends also on the compatibility between substances. In consideration of the above, it is difficult to say that there are sufficient variations of materials with which light-emitting elements having good characteristics can be manufactured.

REFERENCE

Patent Document 1: Japanese Published Patent Application No. 2007-15933

SUMMARY OF THE INVENTION

Therefore, an object of one embodiment of the present invention is to provide a novel carbazole compound that can be used for a transport layer, a host material, or a light-emitting material in a light-emitting element.

Another object of one embodiment of the present invention is to provide a light-emitting element material using the above novel carbazole compound.

Another object of one embodiment of the present invention is to provide an organic semiconductor material using the above novel carbazole compound. Note that in one embodiment of the present invention, it is only necessary that at least one of the above-described objects should be achieved.

The present inventors have found the good carrier-transport property of a carbazole compound, in which two carbazole skeletons each include carbazole, the 3-position of which is bonded to the 4-position of a dibenzofuran skeleton or a dibenzothiophene skeleton and these two carbazole skeletons are linked via benzene or biphenyl, and found that the carbazole compound can be suitably used for a material in a light-emitting element or for an organic semiconductor material. Further, the inventors have found that the carbazole compound has a large energy gap.

Specifically, one embodiment of the present invention is a carbazole compound represented by a general formula (G1) below.

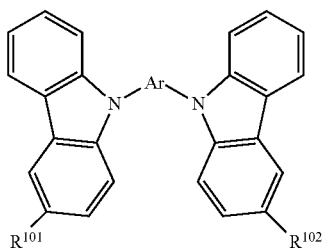

In the general formula (G1), Ar represents a substituted or unsubstituted phenylene group or a substituted or unsubstituted biphenyldiyl group, and $R^{101}$ and $R^{102}$ each independently represent a group represented by a general formula (g1) below.

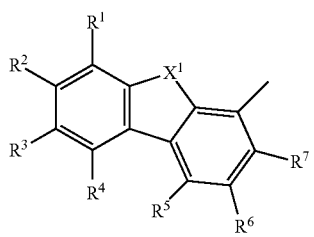

In the general formula (g1), $X^1$ represents sulfur or oxygen, and $R^1$ to $R^7$ each independently represent any of hydrogen, an alkyl group having 1 to 4 carbon atoms, and an aryl group having 6 to 12 carbon atoms.

Another embodiment of the present invention is a carbazole compound represented by the general formula (G1) below.

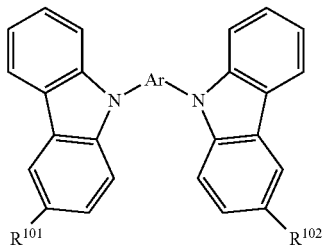

In the general formula (G1), Ar represents an unsubstituted phenylene group or an unsubstituted biphenyldiyl group, and $R^{101}$ and $R^{102}$ each independently represent a group represented by the following general formula (g1).

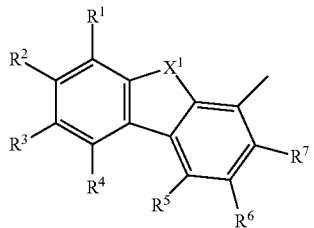

In the general formula (g1), $X^1$ represents sulfur or oxygen, and $R^1$ to $R^7$ each independently represent any of hydrogen, an alkyl group having 1 to 4 carbon atoms, and an aryl group having 6 to 12 carbon atoms.

Another embodiment of the present invention is a carbazole compound represented by a general formula (G2) below.

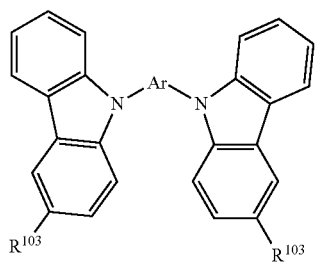

In the general formula (G2), Ar represents a substituted or unsubstituted phenylene group or a substituted or unsubstituted biphenyldiyl group, and $R^{103}$ represents a group represented by the following general formula (g1).

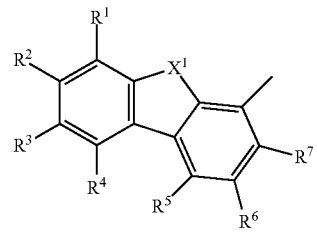

In the general formula (g1), $X^1$ represents sulfur or oxygen, and $R^1$ to $R^7$ each independently represent any of hydrogen, an alkyl group having 1 to 4 carbon atoms, and an aryl group having 6 to 12 carbon atoms.

Another embodiment of the present invention is a carbazole compound represented by the general formula (G2) below.

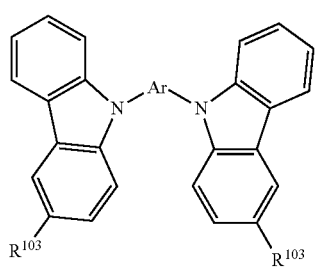

In the general formula (G2), Ar represents an unsubstituted phenylene group or an unsubstituted biphenyldiyl group, and $R^{103}$ represents a group represented by the following general formula (g1).

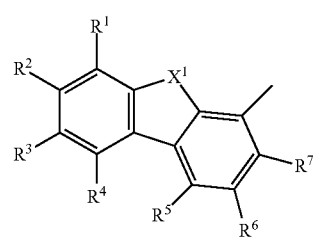

In the general formula (g1), $X^1$ represents sulfur or oxygen, and $R^1$ to $R^7$ each independently represent any of hydrogen, an alkyl group having 1 to 4 carbon atoms, and an aryl group having 6 to 12 carbon atoms.

Another embodiment of the present invention is a carbazole compound represented by a general formula (G3) below.

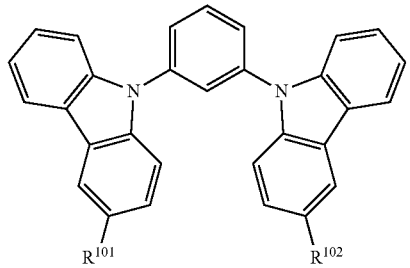

(G3)

In the general formula (G3), $R^{101}$ and $R^{102}$ each independently represent a group represented by the following general formula (g1).

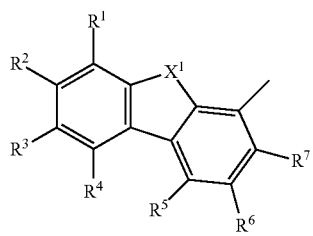

(g1)

In the general formula (g1), $X^1$ represents sulfur or oxygen, and $R^1$ to $R^7$ each independently represent any of hydrogen, an alkyl group having 1 to 4 carbon atoms, and an aryl group having 6 to 12 carbon atoms.

Another embodiment of the present invention is a carbazole compound represented by a general formula (G4) below.

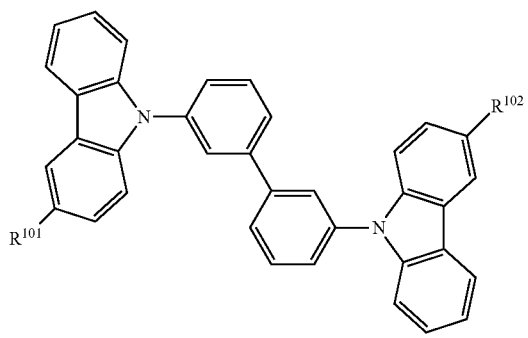

(G4)

In the general formula (G4), $R^{101}$ and $R^{102}$ each independently represent a group represented by the following general formula (g1).

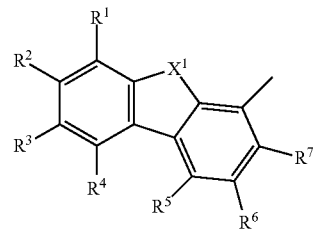

(g1)

In the general formula (g1), $X^1$ represents sulfur or oxygen, and $R^1$ to $R^7$ each independently represent any of hydrogen, an alkyl group having 1 to 4 carbon atoms, and an aryl group having 6 to 12 carbon atoms.

Another embodiment of the present invention is a carbazole compound represented by a general formula (G5) below.

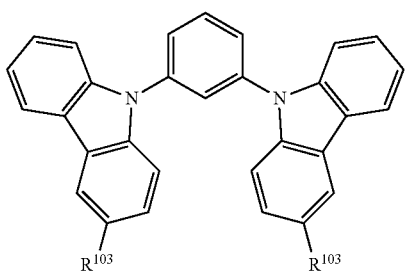

(G5)

In the general formula (G5), $R^{103}$ represents a group represented by the following general formula (g1).

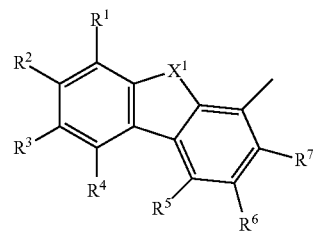

(g1)

In the general formula (g1), $X^1$ represents sulfur or oxygen, and $R^1$ to $R^7$ each independently represent any of hydrogen, an alkyl group having 1 to 4 carbon atoms, and an aryl group having 6 to 12 carbon atoms.

Another embodiment of the present invention is a carbazole compound represented by a general formula (G6) below.

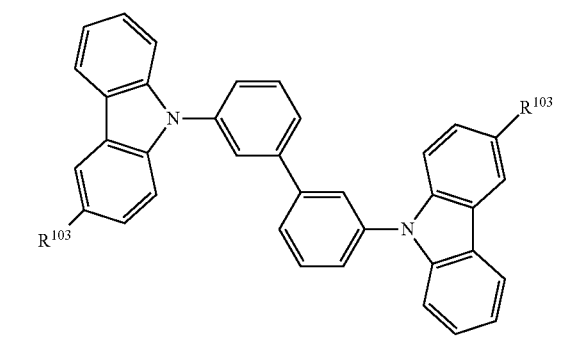

(G6)

In the general formula (G6), $R^{103}$ represents a group represented by the following general formula (g1).

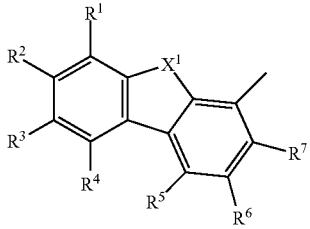

(g1)

In the general formula (g1), $X^1$ represents sulfur or oxygen, and $R^1$ to $R^7$ each independently represent any of hydrogen, an alkyl group having 1 to 4 carbon atoms, and an aryl group having 6 to 12 carbon atoms.

Another embodiment of the present invention is a carbazole compound which has any of the above structures and in which the group represented by the general formula (g1) is represented by the following general formula (g2).

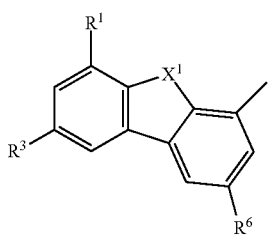

(g2)

In the general formula (g2), $X^1$ represents sulfur or oxygen, and $R^1$, $R^3$, and $R^6$ each independently represent any of hydrogen, an alkyl group having 1 to 4 carbon atoms, and an aryl group having 6 to 12 carbon atoms.

Another embodiment of the present invention is a carbazole compound which has any of the above structures and in which the group represented by the general formula (g1) is represented by the following general formula (g3).

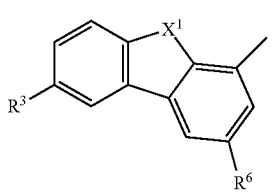

(g3)

In the general formula (g3), $X^1$ represents sulfur or oxygen, and $R^3$ and $R^6$ each independently represent any of hydrogen, an alkyl group having 1 to 4 carbon atoms, and an aryl group having 6 to 12 carbon atoms.

Another embodiment of the present invention is a carbazole compound which has any of the above structures and in which the group represented by the general formula (g1) is represented by the following general formula (g4).

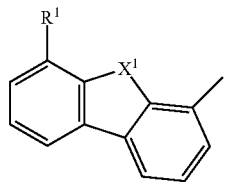

(g4)

In the general formula (g4), $X^1$ represents sulfur or oxygen, and $R^1$ represents any one of hydrogen, an alkyl group having 1 to 4 carbon atoms, and an aryl group having 6 to 12 carbon atoms.

Another embodiment of the present invention is a carbazole compound which has any of the above structures and in which the group represented by the general formula (g1) is represented by the following general formula (g5).

(g5)

In the general formula (g4), $X^1$ represents sulfur or oxygen.

Another embodiment of the present invention is a carbazole compound which has any of the above structures and in which $X^1$ represents sulfur.

The carbazole compound with such a structure has a high carrier-transport property and can be suitably used for a host material or a carrier-transport layer in a light-emitting element. Since the carbazole compound has a high carrier-transport property, a light-emitting element having low driving voltage can be fabricated.

Further, the carbazole compound has a wide energy gap, and therefore can be suitably used for a host material, into which an emission center substance that emits fluorescence or phosphorescence having a wavelength equal to or longer than that of blue light is dispersed. Since the carbazole compound has a wide energy gap and thus high triplet excitation energy, the energy of carriers that recombine in the host material can be effectively transferred to the emission center substance. Thus, a light-emitting element with high emission efficiency can be fabricated.

Also for a carrier-transport layer adjacent to a light-emitting layer containing an emission center substance that emits fluorescence or phosphorescence which is blue or green light, the carbazole compound having a wide energy gap can be suitably used without deactivating excitation energy of the emission center substance. Thus, a light-emitting element with high emission efficiency can be fabricated.

Since the carbazole compound exhibits an excellent carrier-transport property, a light-emitting element having low driving voltage can be provided.

As described above, the carbazole compound has excellent properties for use for a material of a light-emitting element. Therefore, another embodiment of the present invention is a light-emitting element material including a carbazole compound having any of the above structures.

Another embodiment of the present invention is an organic semiconductor material containing a carbazole compound having any of the above structures.

Another embodiment of the present invention is a light-emitting element including a carbazole compound having any of the above structures.

Another embodiment of the present invention is a light-emitting device using the light-emitting element having the above structure.

Another embodiment of the present invention is a lighting device including the light-emitting element having the above structure.

Another embodiment of the present invention is an electronic device including the light-emitting element having the above structure.

A carbazole compound having any of the above-described structures is a substance having both an excellent carrier-transport property and a wide energy gap, and can be suitably used for a material included in a transport layer or a host material or an emission center substance in a light-emitting layer in a light-emitting element. A light-emitting element using a light-emitting element material including the carbazole compound can have high emission efficiency. A light-emitting element including the carbazole compound can have low voltage. A light-emitting element including the carbazole compound can have a long lifetime. Further, the carbazole compound can also be used for an organic semiconductor material.

BRIEF DESCRIPTION OF THE DRAWINGS

In the accompanying drawings:

FIGS. 3A and 3B are conceptual diagrams of an active matrix light-emitting device;

FIG. 9 illustrates in-vehicle display devices and lighting devices;

DETAILED DESCRIPTION OF THE INVENTION

Figure 1A:
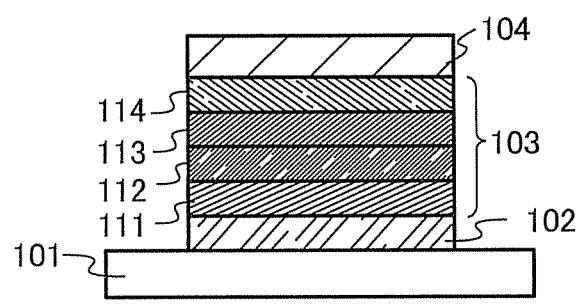
FIGS. 1A and 1B are each a conceptual diagram of a light-emitting element.

Hereinafter, embodiments of the present invention will be described. It is easily understood by those skilled in the art that modes and details disclosed herein can be modified in various ways without departing from the spirit and scope of the present invention. Therefore, the present invention is not construed as being limited to description of the embodiments.

Embodiment 1

A carbazole compound in this embodiment has a structure in which two carbazole skeletons each include carbazole, the 3-position of which is bonded to the 4-position of a dibenzofuran skeleton or a dibenzothiophene skeleton and these two carbazole skeletons are linked via benzene or biphenyl.

The carbazole compound is a novel compound that has a wide energy gap and high triplet excitation energy and can be suitably used for a material in a light-emitting element. The carbazole compound also has an excellent carrier-transport property and can also be suitably used for an organic semiconductor material.

Carbon in the dibenzofuran skeleton or the dibenzothiophene skeleton may also have a substituent. The substituent can be either an alkyl group having 1 to 4 carbon atoms or an aryl group having 6 to 12 carbon atoms. Specific examples of the alkyl group having 1 to 4 carbon atoms are a methyl group, an ethyl group, a propyl group, and a butyl group. Specific examples of the aryl group having 6 to 12 carbon atoms are a phenyl group, a naphthyl group, a biphenyl group, and a tolyl group.

Further, the carbazole compound having such a structure has a wide energy gap, and therefore can be suitably used for a host material, into which an emission center substance that emits fluorescence or phosphorescence having a wavelength equal to or longer than that of blue light is dispersed. Since the carbazole compound has a wide energy gap and thus high triplet excitation energy, the energy of carriers that recombine in the host material can be effectively transferred to the emission center substance. Thus, a light-emitting element with high emission efficiency can be fabricated.

Also for a carrier-transport layer adjacent to a light-emitting layer containing an emission center substance that emits fluorescence or phosphorescence having a wavelength equal to or longer than that of blue light, the carbazole compound having a wide energy gap can be suitably used without deactivating excitation energy of the emission center substance. Thus, a light-emitting element with high emission efficiency can be fabricated.

The carbazole compound has a high carrier-transport property and can be suitably used for a host material or a carrier-transport layer in a light-emitting element. Since the carbazole compound has a high carrier-transport property, a light-emitting element having low driving voltage can be fabricated.

The above-described carbazole compound can also be represented by the general formula (G1) below.

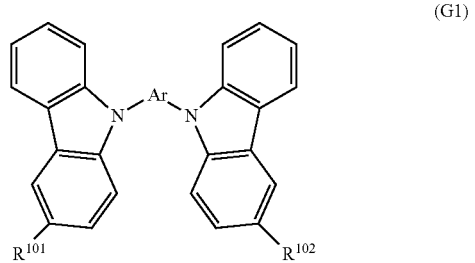

(G1)

In the general formula (G1), Ar represents a substituted or unsubstituted phenylene group or a substituted or unsubstituted biphenyldiyl group, and $R^{101}$ and $R^{102}$ each independently represent a group represented by the following general formula (g1).

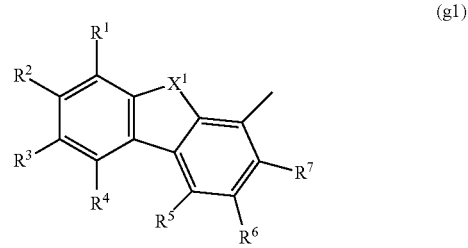

(g1)

In the general formula (g1), $X^1$ represents sulfur or oxygen, and $R^1$ to $R^7$ each independently represent any of hydrogen, an alkyl group having 1 to 4 carbon atoms, and an aryl group having 6 to 12 carbon atoms. In the formula (G1), when the group denoted as Ar has a substituent, the substituent can be an alkyl group having 1 to 4 carbon atoms, an alkoxyl group having 1 or 2 carbon atoms, fluorine, an aryl group having 6 to 12 carbon atoms, a trialkylsilyl group, or the like.

Specific examples of the groups denoted as Ar in the general formula (G1) are groups represented by the following structural formulae (Ar-1) to (Ar-30).

(Ar-1)

(Ar-2)

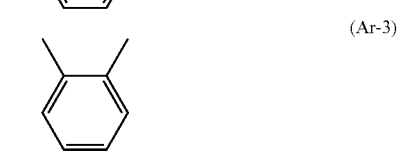

(Ar-3)

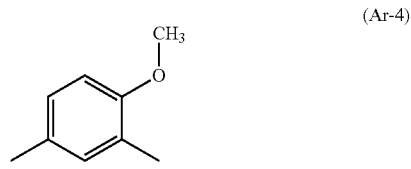

(Ar-4)

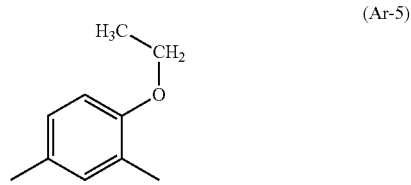

(Ar-5)

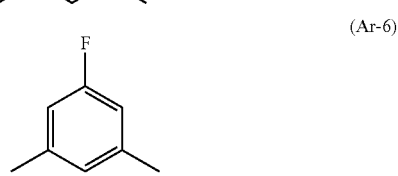

(Ar-6)

-continued
(Ar-7)
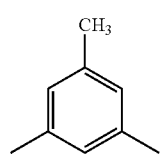
(Ar-8)
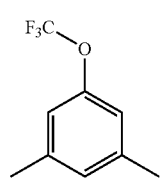
(Ar-9)
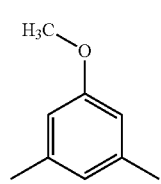
(Ar-10)
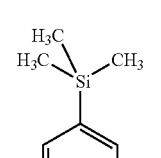
(Ar-11)
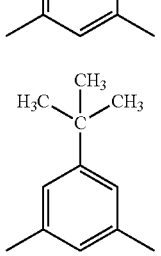
(Ar-12)
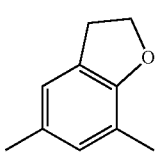
(Ar-13)
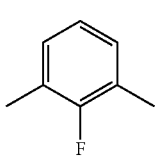
(Ar-14)
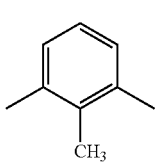
(Ar-15)
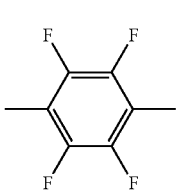
-continued
(Ar-16)
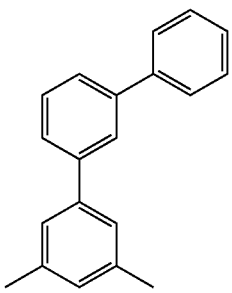
(Ar-17)
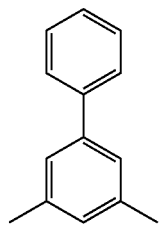
(Ar-18)
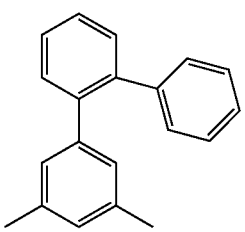
(Ar-19)
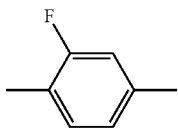
(Ar-20)
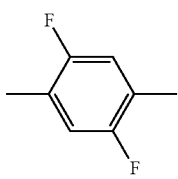
(Ar-21)
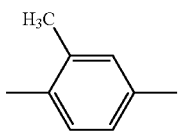
(Ar-22)
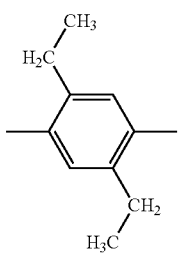

(Ar-23) 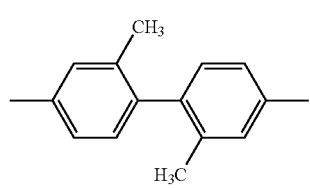

(Ar-24) 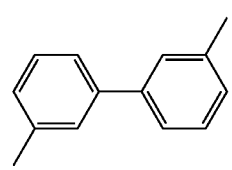

(Ar-25) 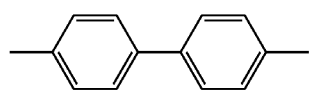

(Ar-26) 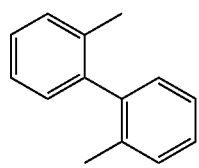

(Ar-27) 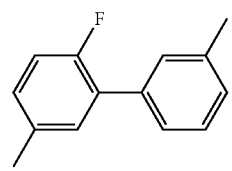

(Ar-28) 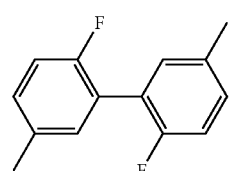

(Ar-29) 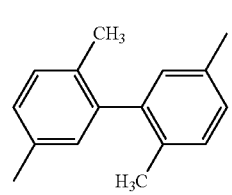

(Ar-30) 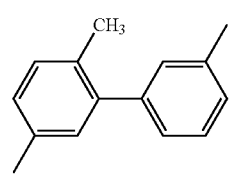

Specific examples of the groups represented by $R^1$ to $R^7$ in the general formula (g1) are groups represented by the following structural formulae (R-1) to (R-6).

(R-1) 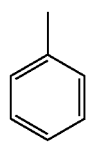

(R-2) 

(R-3) 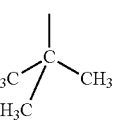

(R-4) 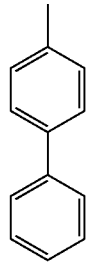

(R-5) 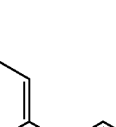

(R-6) 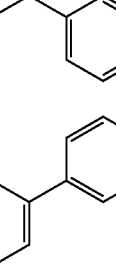

It is preferable in the above general formula (g1) that, when the dibenzothiophene skeleton or the dibenzofuran skeleton has a substituent, the substituent be positioned at one or more of $R^1$, $R^3$, and $R^6$. This is because the substituent is easy to introduce through bromination or conversion into boronic acid and a compound having with such a substituent is easy to synthesize. It is further preferable that $R^1$ to $R^7$ be each hydrogen, in which case the compound can have an advantage in terms of availability of a raw material and synthesis can be inexpensive.

When Ar is a phenylene group, the phenylene group is preferably meta-substituted or ortho-substituted, in which case the compound can have an advantage in terms of energy gap. Also when Ar is a biphenyldiyl group, the biphenyldiyl group is preferably a curved biphenyldiyl group such as a biphenyl-3,3'-diyl group or a biphenyl-2,2'-diyl group, in which case the compound can have a large energy gap or high triplet excitation energy.

Specific examples of structures of the carbazole compound represented by the above general formula (G1) are substances represented by the following structural formulae (100) to (149) and the like.

(100)
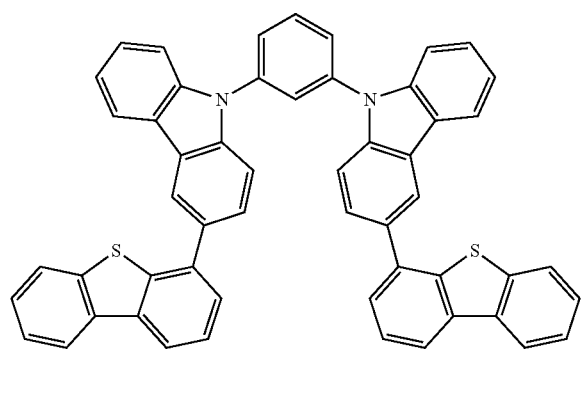
(101)
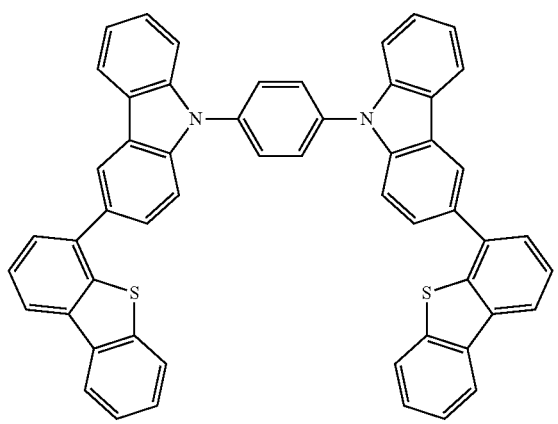
(102)
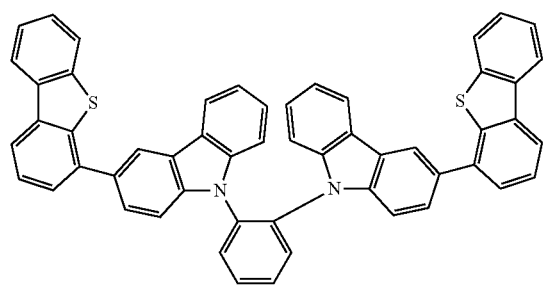
(103)
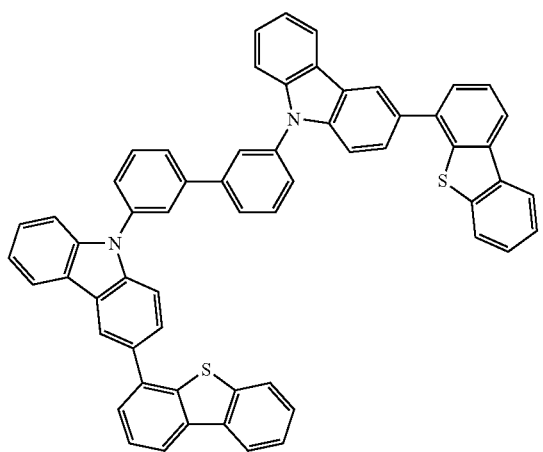
(104)
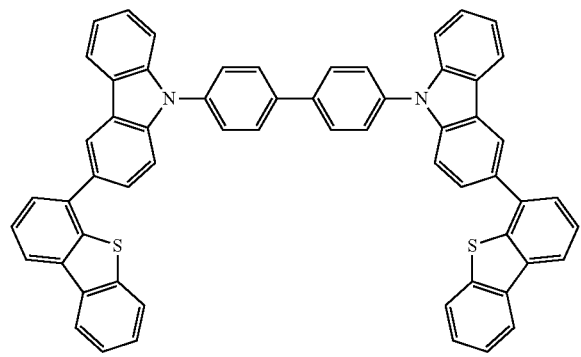
(105)
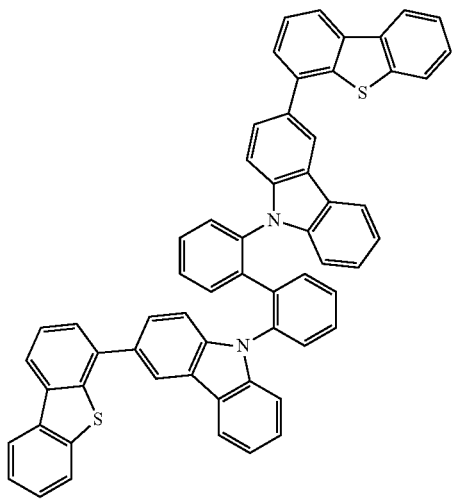

-continued
(106)
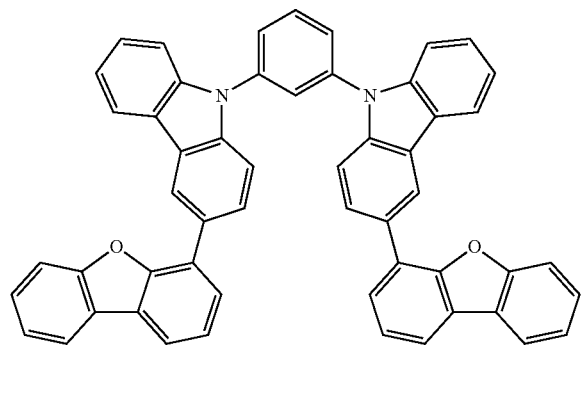
(107)
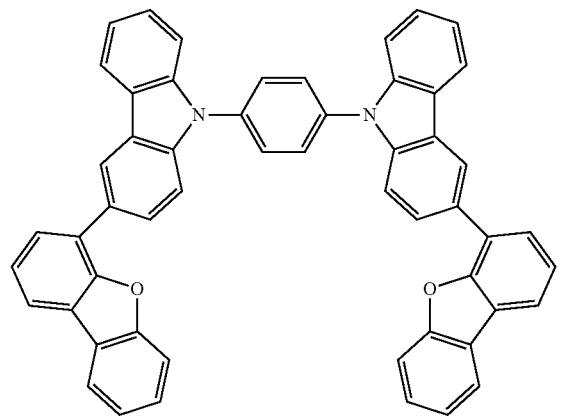
(108)
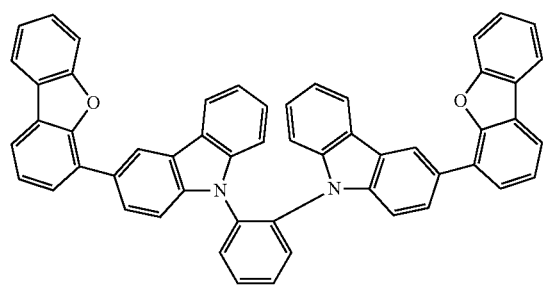
(109)
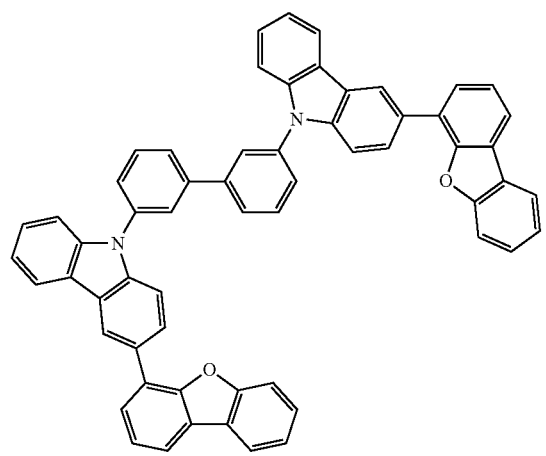
(110)
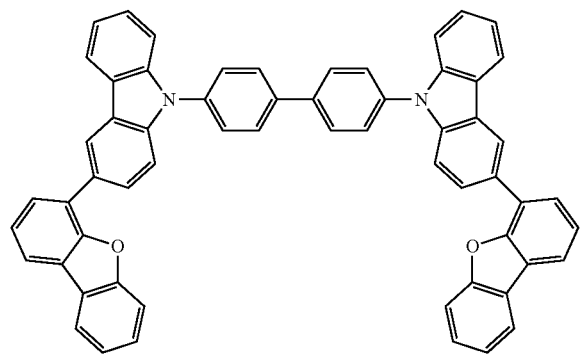
(111)
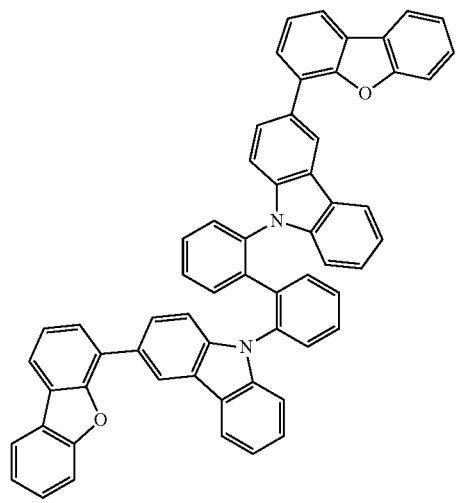

-continued
(112)
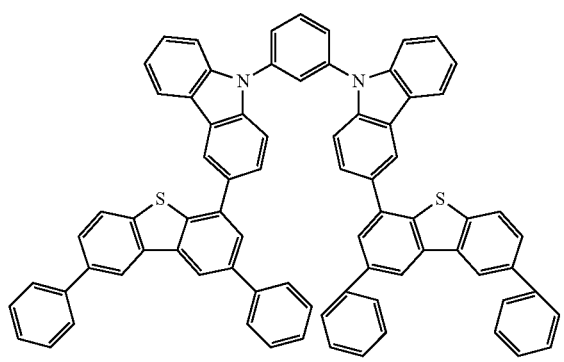
(113)
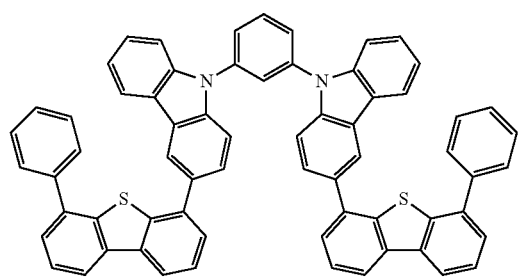
(114)
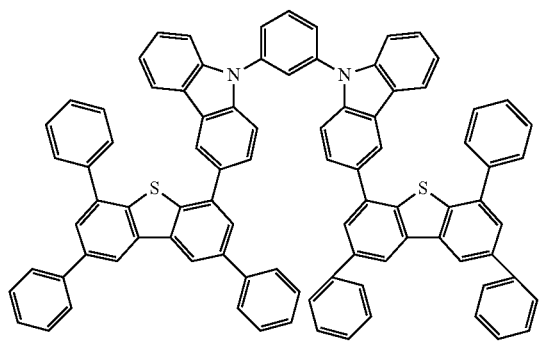
(115)
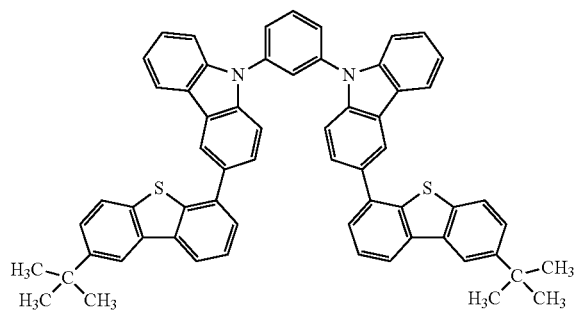
(116)
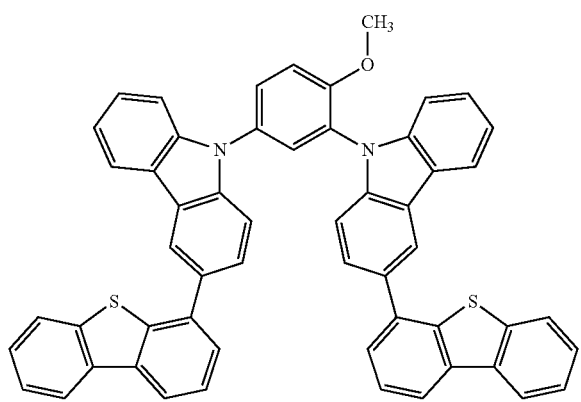
(117)
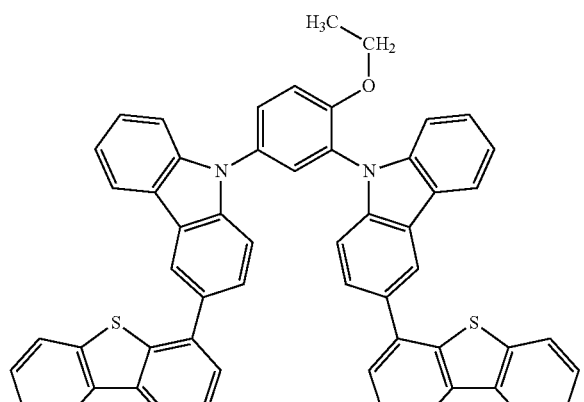

-continued
(118)
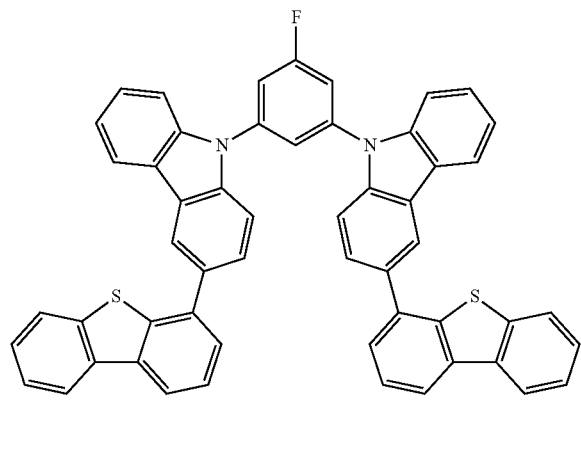
(119)
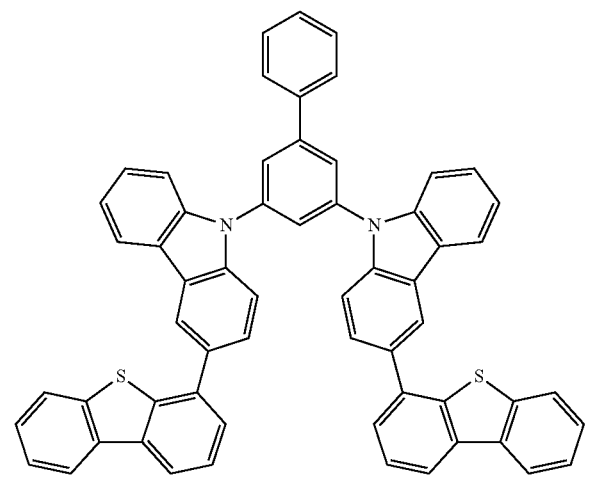
(120)
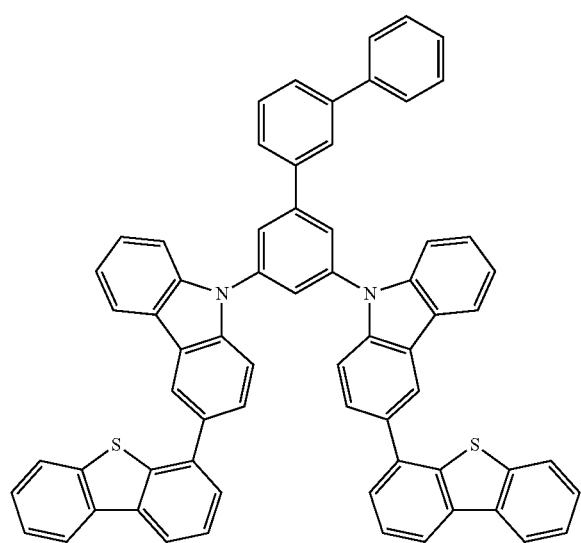
(121)
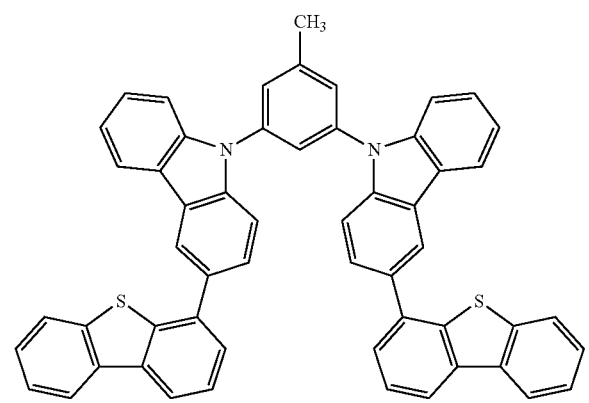
(122)
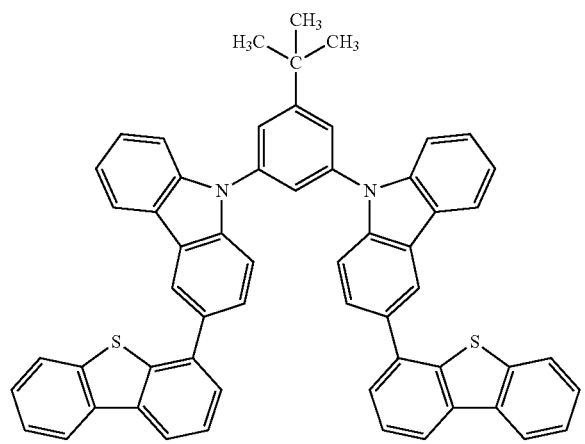
(123)
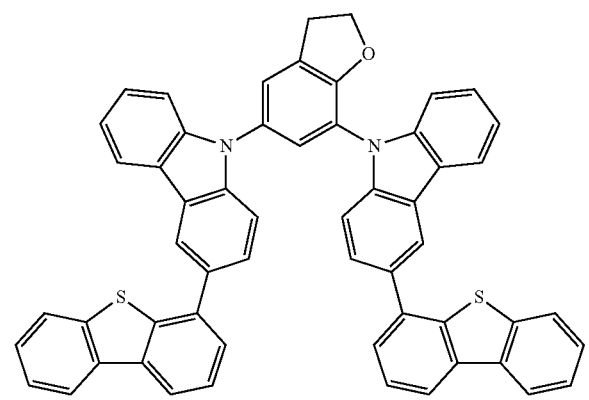

-continued
(124)
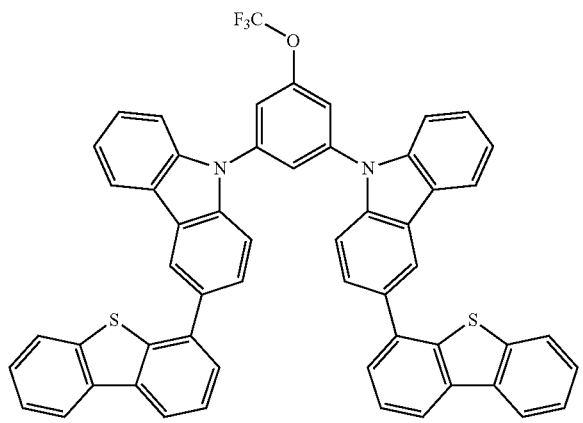
(125)
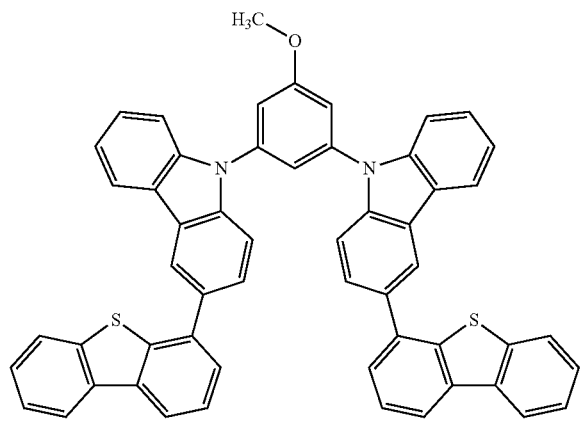
(126)
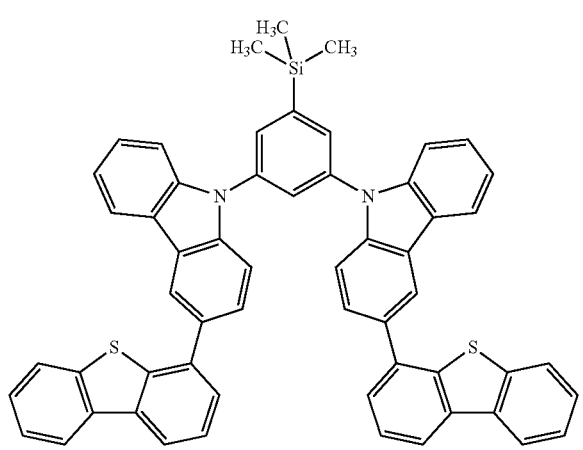
(127)
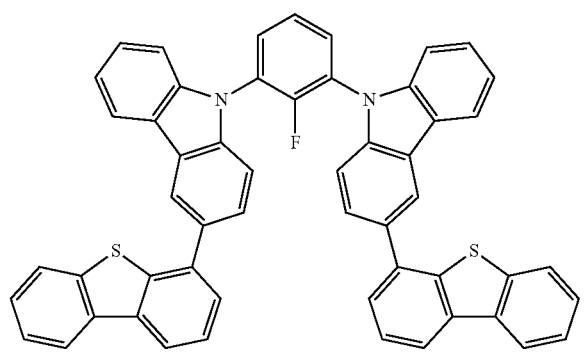
(128)
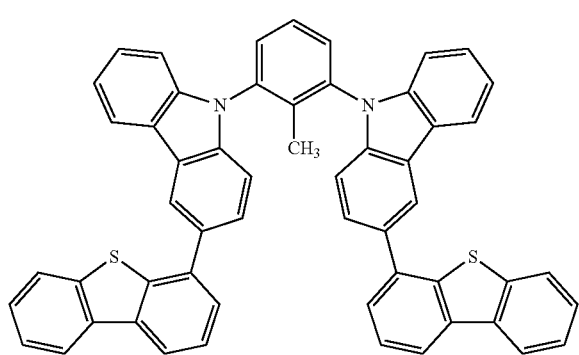
(129)
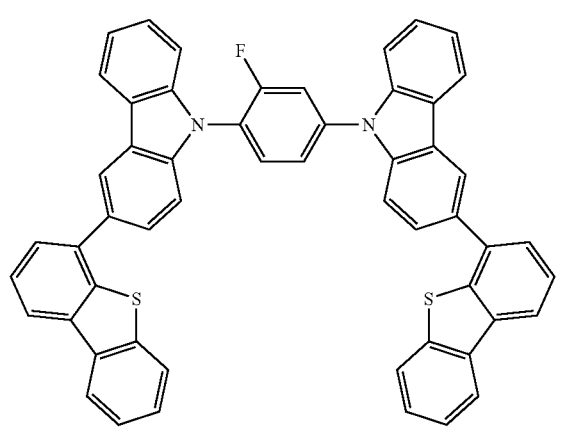

-continued
(130)
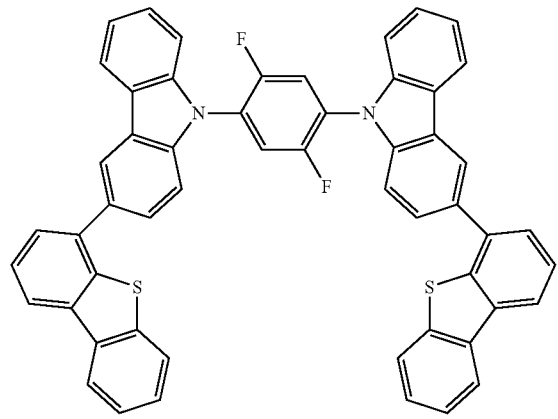
(131)
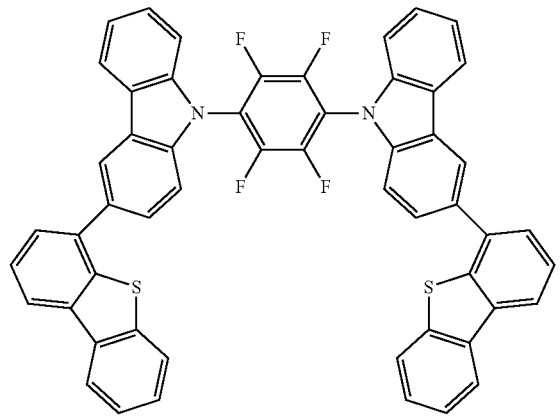
(132)
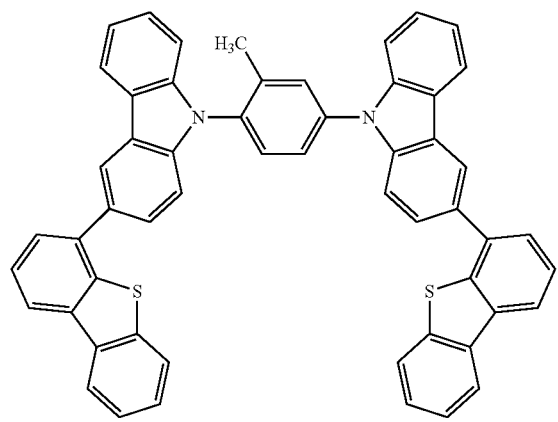
(133)
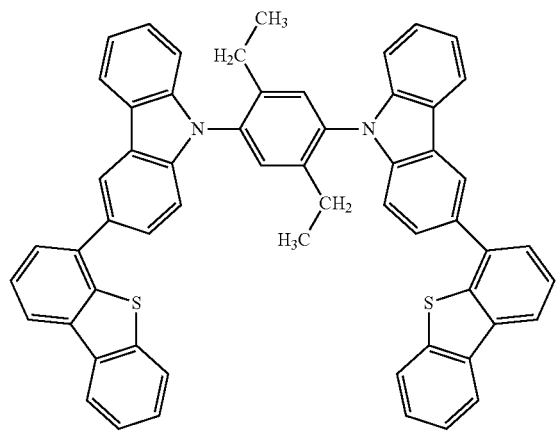
(134)
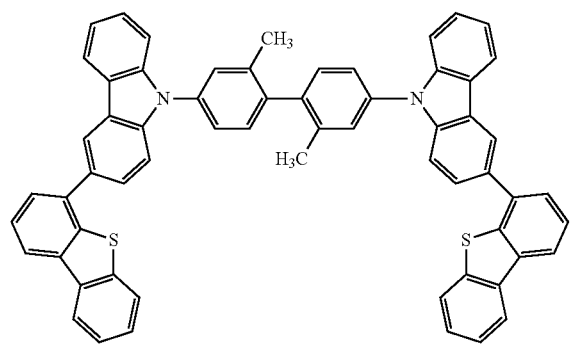
(135)
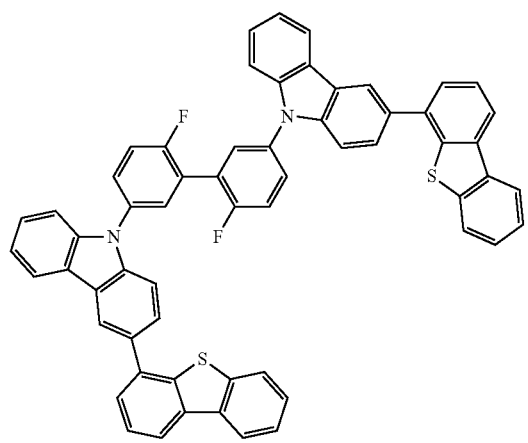

-continued
(136)
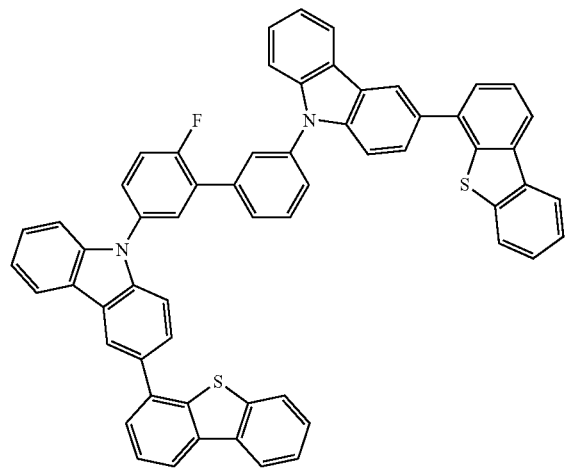
(137)
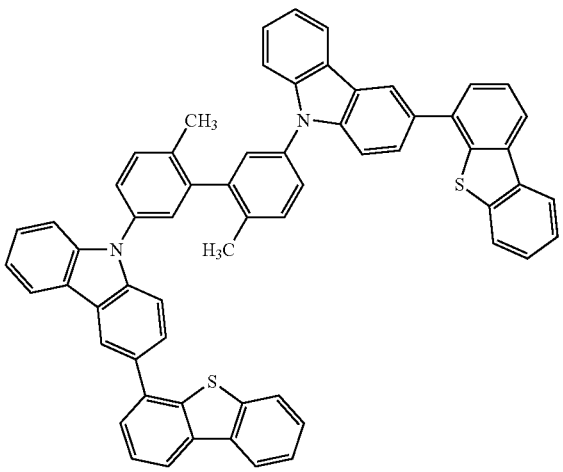
(138)
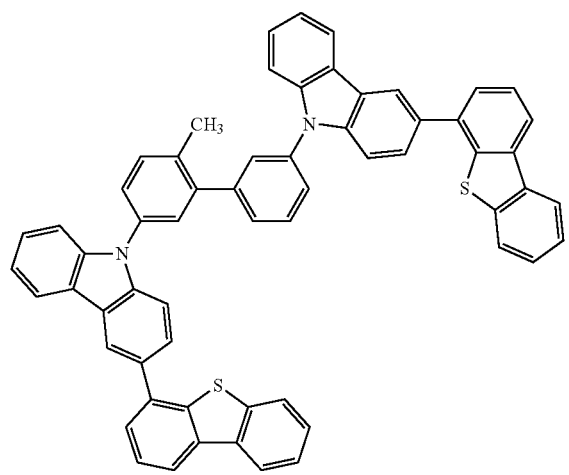
(139)
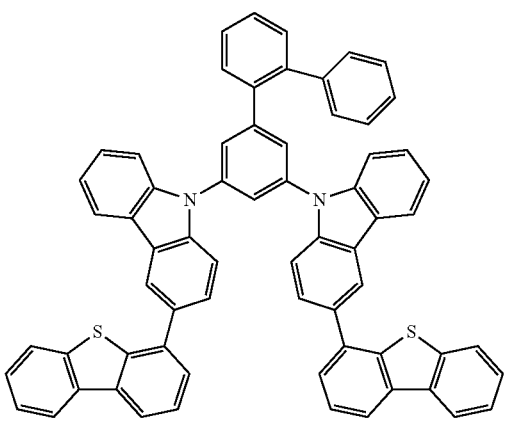
(140)
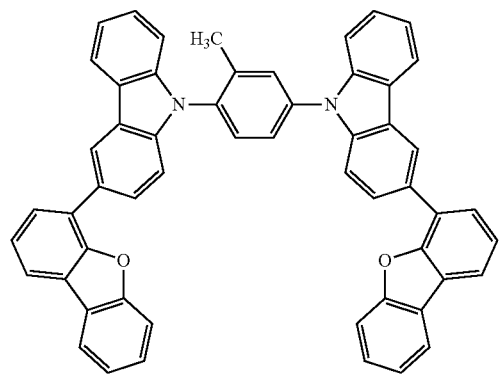
(141)
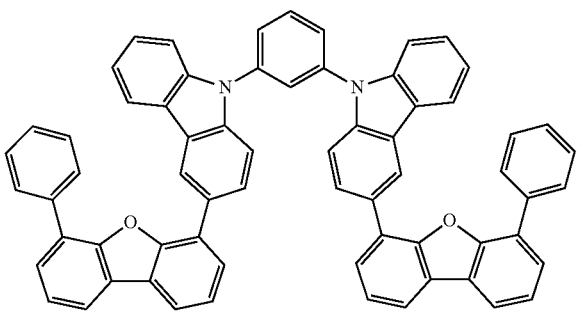

-continued
(142)
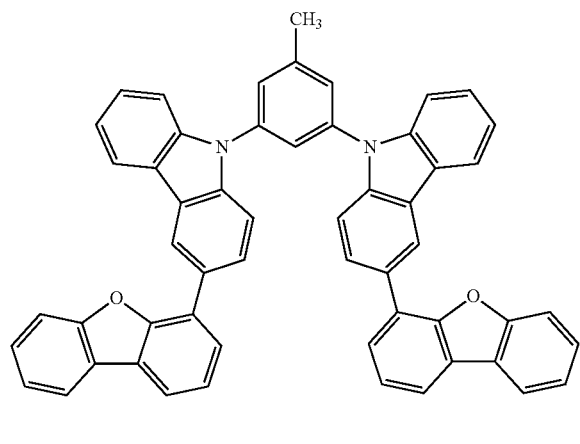
(143)
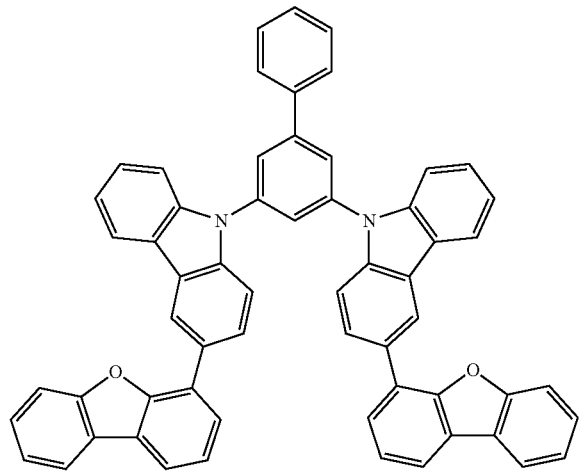
(144)
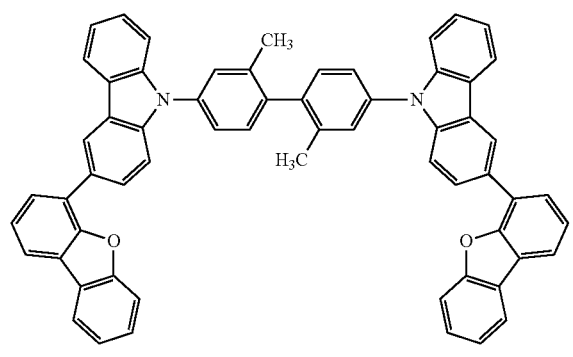
(145)
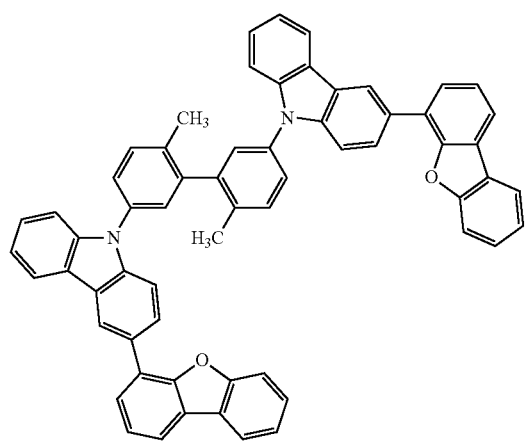
(146)
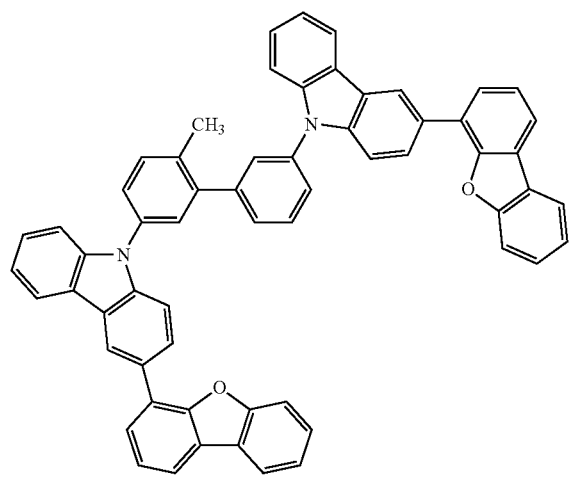
(147)
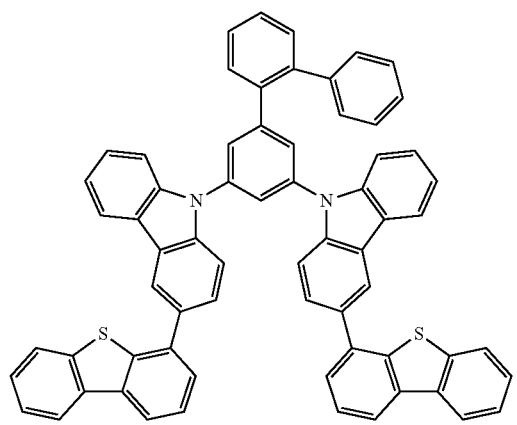

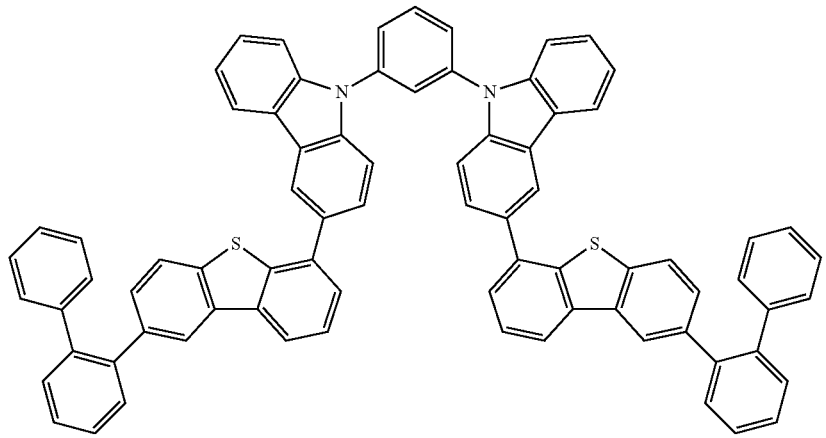

(148)

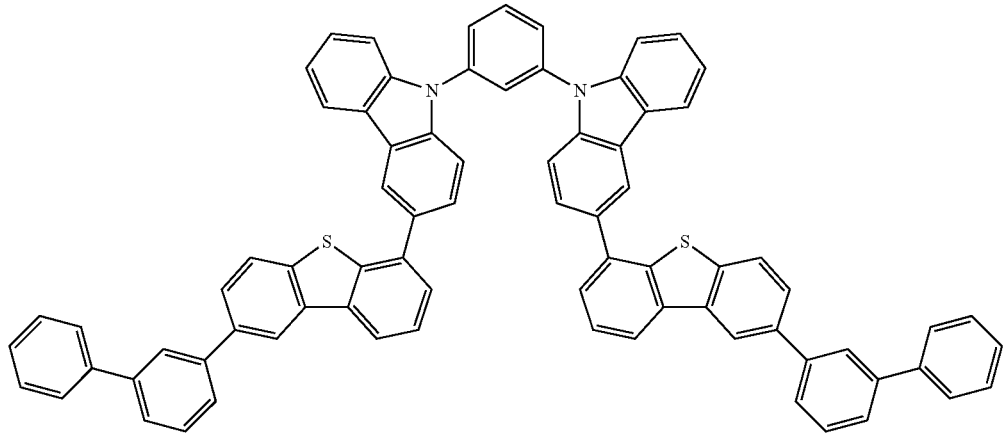

(149)

A carbazole compound described above has an excellent carrier-transport property and therefore is suitable for a carrier-transport material or a host material; thus, a light-emitting element having low driving voltage can also be provided. Further, the carbazole compound has high triplet excitation energy (a large energy difference between the triplet excited state and the ground state), and thus a phosphorescent light-emitting element having high emission efficiency can be obtained. In addition, since the carbazole compound has high triplet excitation energy indicates also having a wide energy gap, the carbazole compound enables even a light-emitting element for emitting blue fluorescence to efficiently emit light.

Furthermore, a carbazole compound in this embodiment has a rigid group such as dibenzothiophene or dibenzofuran, and therefore has excellent morphology, gives stable film quality, and also has an excellent thermophysical property. Thus, a light-emitting element using a carbazole compound in this embodiment can have a long lifetime which shows a small luminance decrease relative to driving time.

In addition, a carbazole compound in this embodiment can be used for a light-emitting material that emits blue to ultraviolet light.

Next, a method of synthesizing the carbazole compound represented by the general formula (G1) below is described.

A variety of reactions can be applied to the method of synthesizing the carbazole compound. For example, synthesis reactions described below enable the synthesis of the carbazole compound represented by the general formula (G1). In the general formula (G1), Ar represents a substituted or unsubstituted phenylene group or a substituted or unsubstituted biphenyldiyl group, and $R^{101}$ and $R^{102}$ each independently represent a substituent represented by the general formula (g1) below. In the general formula (g1), $X^1$ represents sulfur or oxygen, and $R^1$ to $R^7$ each independently represent hydrogen, an alkyl group having 1 to 4 carbon atoms, or an aryl group having 6 to 12 carbon atoms.

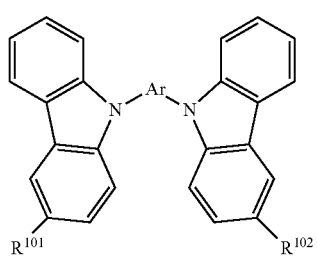

(G1)

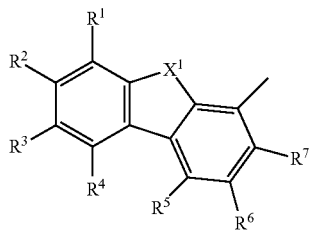

First, a compound 1 having a halogeno group or a triflate group at the 3-position of 9H-carbazole is coupled with a boronic acid compound (compound 2) of dibenzofuran (or dibenzothiophene), so that a 9H-carbazole compound having a structure in which the 3-position of 9H-carbazole is bonded to the 4-position of dibenzofuran (or dibenzothiophene) (compound 12) can be obtained (reaction formula (A-1)).

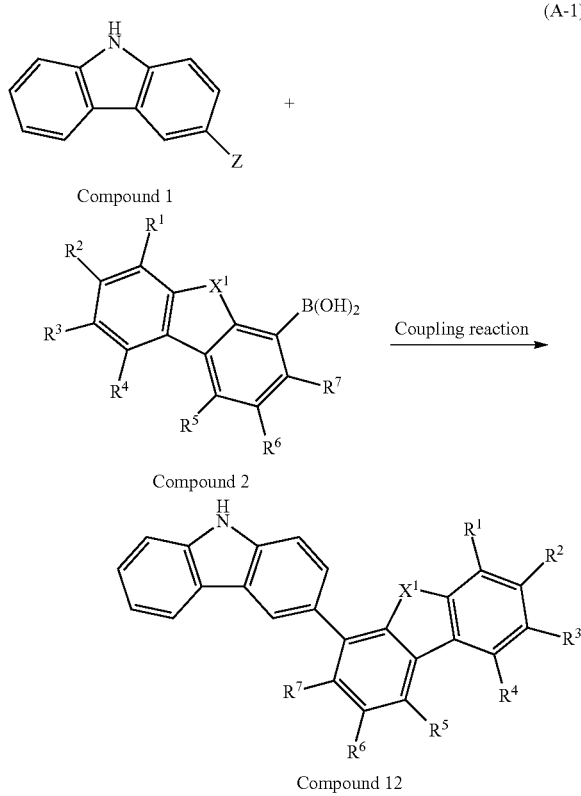

In the reaction formula (A-1), $X^1$ represents sulfur or oxygen, Z represents a halogeno group, a triflate group, or the like, and $R^1$ to $R^7$ each independently represent any of hydrogen, an alkyl group having 1 to 4 carbon atoms, and an aryl group having 6 to 12 carbon atoms. The aryl group may have a substituent. Further, the compound 2 may be a boron compound in which boronic acid is protected with ethylene glycol or the like. As the coupling reaction in the reaction formula (A-1), a Suzuki-Miyaura coupling reaction using a palladium catalyst can be used.

Alternatively, for example, a Kumada coupling reaction using a Grignard reagent as substitute for the boronic acid compound in the compound 2, a Negishi coupling reaction using an organozinc compound as substitute for the boronic acid compound, or a Migita-Kosugi-Stille coupling using an organotin compound as substitute for the boronic acid compound may be performed.

To synthesis a 9H-carbazole compound having a structure in which the 2-position of 9H-carbazole is bonded to the 4-position of dibenzofuran (or dibenzothiophene), the method as described above is employed with, instead of the compound 1, a compound having a halogeno group or a triflate group at the 2-position of 9H-carbazole. The dibenzothiophene skeleton or dibenzofuran skeleton in the compound 12 is hereinafter abbreviated as $R^{101}$ to $R^{103}$.

Then, the aryl compound (compound 11) and the carbazole compound (compound 12) undergo a coupling reaction, so that a carbazole compound (compound 13) can be obtained (reaction formula (A-2)). In the reaction formula (A-2), $X^{11}$ and $X^{12}$ each represent a halogeno group, and $R^{101}$ represents a substituent represented by the general formula (g1) below. In the following general formula (g1), $X^1$ represents sulfur or oxygen, and $R^1$ to $R^7$ each independently represent hydrogen, an alkyl group having 1 to 4 carbon atoms, or an aryl group having 6 to 12 carbon atoms.

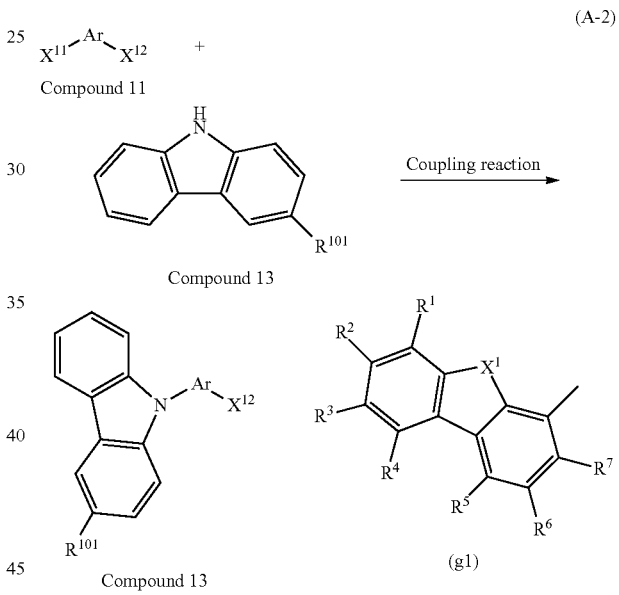

A variety of reaction conditions can be employed for the coupling reaction of the aryl compound having a halogen group (compound 11) and the 9-position of the carbazole compound (compound 12) in the reaction formula (A-2). For example, it is possible to use a coupling reaction using a metal catalyst in the presence of a base, such as a Hartwig-Buchwald reaction using a palladium catalyst in the presence of a base or an Ullmann reaction using copper or a copper compound in the presence of a base.

A case where a Hartwig-Buchwald reaction is performed is described. In this reaction, a palladium catalyst is used. As the palladium catalyst or its precursor, bis(dibenzylideneacetone)palladium(0), palladium(II) acetate, or the like can be used. As a substance which acts as a ligand of palladium and enables a catalytic cycle to proceed smoothly, tri(tert-butyl)phosphine, tri(n-hexyl)phosphine, tricyclohexylphosphine, or the like is preferred. As a substance which can be used for the base, an organic base such as sodium tert-butoxide, an inorganic base such as potassium carbonate, and the like are given. This reaction is preferably performed in a solution, and toluene, xylene, benzene, tetrahydrofuran, or the like can be used as the solvent. Note that the catalyst, ligand, base, and solvent which can be used are not limited to the above. This reaction is preferably performed under an inert atmosphere of nitrogen, argon, or the like.

A case where an Ullmann reaction is performed in the reaction formula (A-2) is described. As a substance which can be used as a copper catalyst, copper, copper(I) iodide, copper (II) acetate, and the like can be given. As a substance that can be used as the base, an inorganic base such as potassium carbonate can be given. This reaction is preferably performed in a solution, and 1,3-dimethyl-3,4,5,6-tetrahydro-2(1H)-pyrimidinone (abbreviation: DMPU), toluene, xylene, benzene, or the like can be used as the solvent. Note that the catalyst, ligand, base, and solvent which can be used are not limited to the above. In addition, this reaction is preferably performed under an inert atmosphere of nitrogen, argon, or the like. Note that DMPU or xylene, which has a high boiling point, is preferably used in an Ullmann reaction, in which case the object of the synthesis can be obtained in a shorter time and a higher yield at a reaction temperature of 100° C. or more. A reaction temperature of 150° C. or more is further preferred and accordingly DMPU is more preferably used.

Next is described a method of synthesizing a carbazole compound represented by the general formula (G1) in accordance with a reaction formula (A-3) given below.

The carbazole compound (compound 13) and a carbazole compound (compound 14) undergo a coupling reaction, so that the compound (G1) which is the object of the synthesis can be obtained (reaction formula (A-3)). In the reaction formula (A-3), $X^{12}$ represents a halogeno group, Ar represents a substituted or unsubstituted phenylene group or a substituted or unsubstituted biphenyldiyl group, and $R^{101}$ and $R^{102}$ each independently represent a substituent represented by the general formula (g1) below. In the following general formula (g1), $X^1$ represents sulfur or oxygen, and $R^1$ to $R^2$ each independently represent hydrogen, an alkyl group having 1 to 4 carbon atoms, or an aryl group having 6 to 12 carbon atoms.

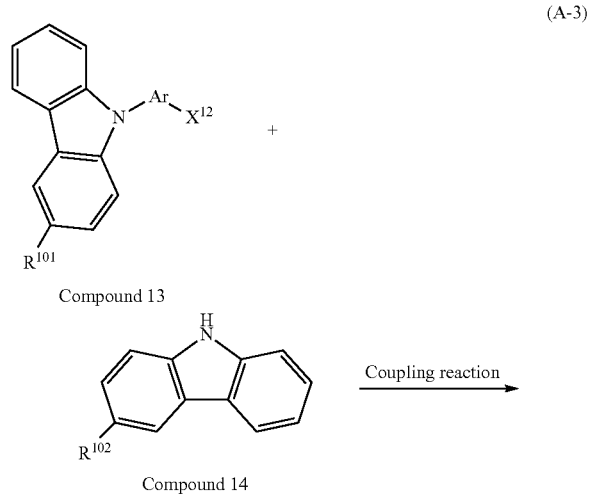

Compound 13

Compound 14

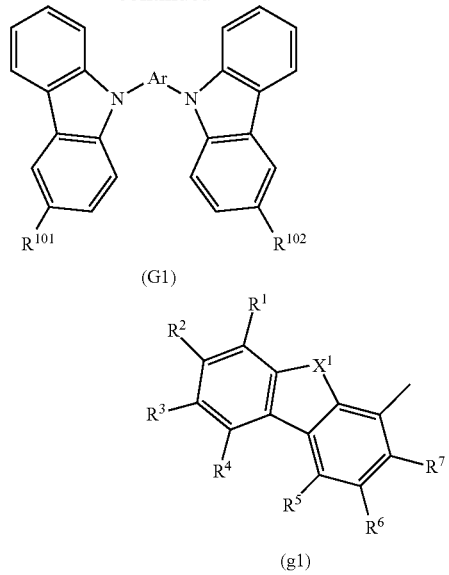

(G1)

(g1)

A variety of reaction conditions can be employed for the coupling reaction of the carbazole compound having a halogeno group (compound 13) and the 9-position of the carbazole compound (compound 14) in the reaction formula (A-3). For example, it is possible to use a coupling reaction using a metal catalyst in the presence of a base, such as a Hartwig-Buchwald reaction using a palladium catalyst in the presence of a base or an Ullmann reaction using copper or a copper compound as a catalyst in the presence of a base.

A case where a Hartwig-Buchwald reaction is performed is described. In this reaction, a palladium catalyst is used. As the palladium catalyst or its precursor, bis(dibenzylideneacetone)palladium(0), palladium(II) acetate, or the like can be used. As a substance which acts as a ligand of palladium and enables a catalytic cycle to proceed smoothly, tri(tert-butyl)phosphine, tri(n-hexyl)phosphine, tricyclohexylphosphine, or the like is preferred. As a substance which can be used for the base, an organic base such as sodium tert-butoxide, an inorganic base such as potassium carbonate, and the like are given. This reaction is preferably performed in a solution, and toluene, xylene, benzene, tetrahydrofuran, or the like can be used as the solvent. Note that the catalyst, ligand, base, and solvent which can be used are not limited to the above. This reaction is preferably performed under an inert atmosphere of nitrogen, argon, or the like.

A case where an Ullmann reaction is performed in the reaction formula (A-3) is described. As a substance which can be used as a copper catalyst, copper, copper(I) iodide, copper (II) acetate, and the like can be given. As a substance that can be used as the base, an inorganic base such as potassium carbonate can be given. This reaction is preferably performed in a solution, and 1,3-dimethyl-3,4,5,6-tetrahydro-2(1H)-pyrimidinone (abbreviation: DMPU), toluene, xylene, benzene, or the like can be used as the solvent. Note that the catalyst, ligand, base, and solvent which can be used are not limited to the above. In addition, this reaction is preferably performed under an inert atmosphere of nitrogen, argon, or the like. Note that DMPU or xylene, which has a high boiling point, is preferably used in an Ullmann reaction, in which case the object of the synthesis can be obtained in a shorter time and a higher yield at a reaction temperature of 100° C. or more. A reaction temperature of 150° C. or more is further preferred and accordingly DMPU is more preferably used.

Next is described a method of synthesizing a carbazole compound represented by the general formula (G1) in accordance with a reaction formula (B-1) given below. The object of the synthesis (G1') in the reaction formula (B-1) given below corresponds to a compound represented by the general formula (G1) in the reaction formula (A-1) in which $R^{101}=R^{102}$.

One equivalent of the aryl compound (compound 11) and two equivalents of the carbazole compound (compound 12) undergo a coupling reaction, so that the compound (G1) which is the object of the synthesis can be obtained (reaction formula (B-1)). In the reaction formula (B-1), $X^{11}$ and $X^{12}$ each represent a halogen group, and $R^{103}$ represents a substituent represented by the general formula (g1) below. In the following general formula (g1), $X^1$ represents sulfur or oxygen, and $R^1$ to $R^7$ each independently represent hydrogen, an alkyl group having 1 to 4 carbon atoms, or an aryl group having 6 to 12 carbon atoms.

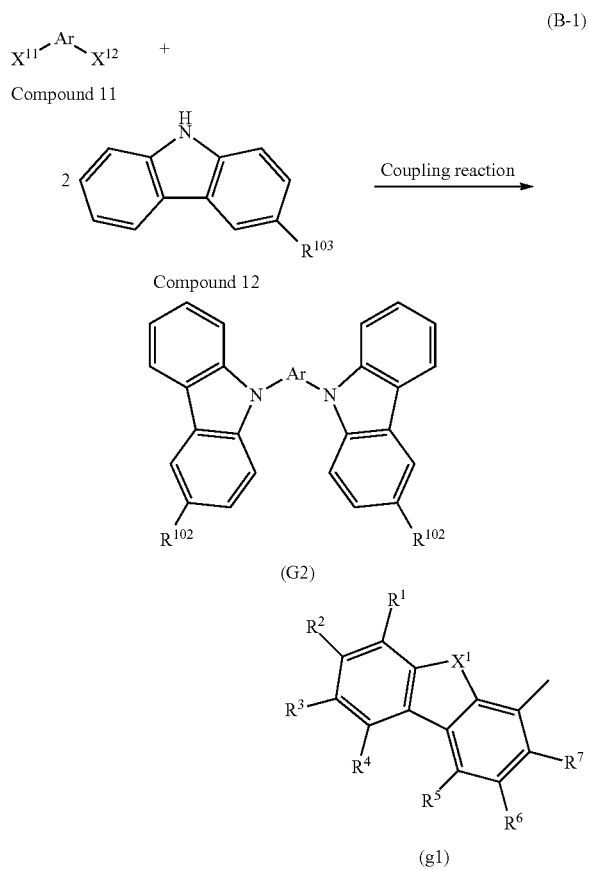

A variety of reaction conditions can be employed for the coupling reaction of the aryl compound having a halogen group (compound 11) and the 9-position of the carbazole compound (compound 12) in the reaction formula (B-1). For example, it is possible to use a coupling reaction using a metal catalyst in the presence of a base, such as a Hartwig-Buchwald reaction using a palladium catalyst or an Ullmann reaction using copper or a copper compound.

A case where a Hartwig-Buchwald reaction is performed is described. In this reaction, a palladium catalyst is used. As the palladium catalyst or its precursor, bis(dibenzylideneacetone)palladium(0), palladium(II) acetate, or the like can be used. As a substance which acts as a ligand of palladium and enables a catalytic cycle to proceed smoothly, tri(tert-butyl) phosphine, tri(n-hexyl)phosphine, tricyclohexylphosphine, or the like is preferred. As a substance which can be used for the base, an organic base such as sodium tert-butoxide, an inorganic base such as potassium carbonate, and the like are given. This reaction is preferably performed in a solution, and toluene, xylene, benzene, tetrahydrofuran, or the like can be used as the solvent. Note that the catalyst, ligand, base, and solvent which can be used are not limited to the above. This reaction is preferably performed under an inert atmosphere of nitrogen, argon, or the like.

A case where an Ullmann reaction is performed in the reaction formula (B-1) is described. As a substance which can be used as a copper catalyst, copper, copper(I) iodide, copper (II) acetate, and the like can be given. As a substance that can be used as the base, an inorganic base such as potassium carbonate can be given. This reaction is preferably performed in a solution, and 1,3-dimethyl-3,4,5,6-tetrahydro-2(1H)-pyrimidinone (abbreviation: DMPU), toluene, xylene, benzene, or the like can be used as the solvent. Note that the catalyst, ligand, base, and solvent which can be used are not limited to the above. In addition, this reaction is preferably performed under an inert atmosphere of nitrogen, argon, or the like. Note that DMPU or xylene, which has a high boiling point, is preferably used in an Ullmann reaction, in which case the object of the synthesis can be obtained in a shorter time and a higher yield at a reaction temperature of 100° C. or more. A reaction temperature of 150° C. or more is further preferred and accordingly DMPU is more preferably used.

As described above, a carbazole compound described in Embodiment 1 can be synthesized.

Embodiment 2

In this embodiment is described an example of the mode where a carbazole compound described in Embodiment 1 is used for an active layer of a vertical transistor (static induction transistor: SIT), which is a kind of an organic semiconductor element.

Figure 2:
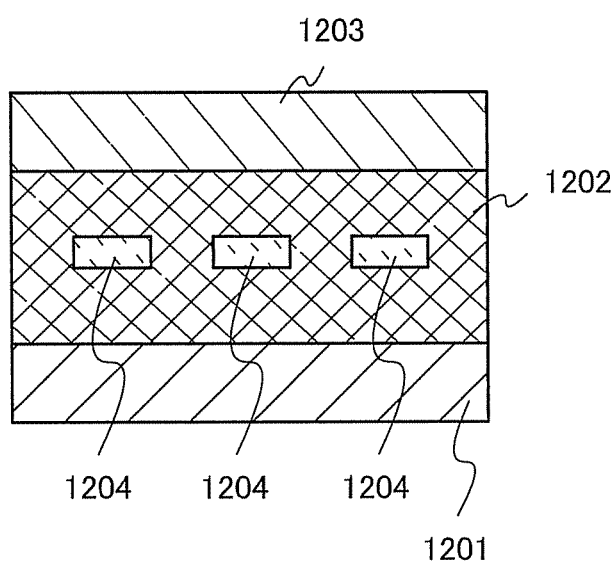
FIG. 2 is a conceptual diagram of an organic semiconductor element.

As illustrated in FIG. 2, the element has a structure in which a thin-film active layer 1202 containing a carbazole compound described in Embodiment 1 is provided between a source electrode 1201 and a drain electrode 1203, and a gate electrode 1204 is embedded in the active layer 1202. The gate electrode 1204 is electrically connected to a means for applying a gate voltage, and the source electrode 1201 and the drain electrode 1203 are electrically connected to a means for controlling a voltage between a source electrode and a drain electrode.

In such an element structure, when a voltage is applied between the source electrode and the drain electrode without applying a voltage to the gate electrode, current flows (on state). Then, by application of a voltage to the gate electrode in that state, a depletion layer is formed in the periphery of the gate electrode 1204, and the current ceases flowing (off state). With such a mechanism, the element operates as a transistor.

Like a light-emitting element, a vertical transistor should contain a material that can achieve both a high carrier-transport property and high quality film for an active layer; a carbazole compound described in Embodiment 1 meets such a requirement and therefore can be suitably used.

Embodiment 3

In this embodiment, one mode of a light-emitting element using a carbazole compound described in Embodiment 1 is described below with reference to FIG. 1A.

The light-emitting element of this embodiment includes a plurality of layers between a pair of electrodes. In this embodiment, the light-emitting element includes a first electrode 102, a second electrode 104, and a layer 103 containing an organic compound, which is provided between the first electrode 102 and the second electrode 104. Note that in this embodiment, the first electrode 102 functions as an anode and the second electrode 104 functions as a cathode. In other words, when a voltage is applied between the first electrode 102 and the second electrode 104 so that the voltage of the first electrode 102 is higher than that of the second electrode 104, light emission can be obtained.

The substrate 101 is used as a support of the light-emitting element. As the substrate 101, glass, plastic or the like can be used, for example. Note that a material other than glass or plastic can be used as far as it can function as a support of the light-emitting element.

For the first electrode 102, any of metals, alloys, electrically conductive compounds, and mixtures thereof which have a high work function (specifically, a work function of 4.0 eV or more) or the like is preferably used. Specifically, for example, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide (IWZO), and the like can be given. Films of these electrically conductive metal oxides are usually fanned by sputtering but may be formed by application of a sol-gel method or the like. For example, indium oxide-zinc oxide can be formed by a sputtering method using a target in which zinc oxide is added to indium oxide at 1 wt % to 20 wt %. Moreover, indium oxide containing tungsten oxide and zinc oxide (IWZO) can be formed by a sputtering method using a target in which tungsten oxide is added to indium oxide at 0.5 wt % to 5 wt % and zinc oxide is added to indium oxide at 0.1 wt % to 1 wt %. Besides, gold (Au), platinum (Pt), nickel (Ni), tungsten (W), chromium (Cr), molybdenum (Mo), iron (Fe), cobalt (Co), copper (Cu), palladium (Pd), nitrides of metal materials (e.g., titanium nitride), and the like can be given. Graphene may also be used.

There is no particular limitation on a stacked structure of the layer 103 containing an organic compound. The layer 103 containing an organic compound can be formed by combining a layer that contains a substance having a high electron-transport property, a layer that contains a substance having a high hole-transport property, a layer that contains a substance having a high electron-injection property, a layer that contains a substance having a high hole-injection property, a layer that contains a bipolar substance (a substance having a high electron-transport and hole-transport property), and the like as appropriate. For example, the layer 103 containing an organic compound can be formed by combining a hole-injection layer, a hole-transport layer, a light-emitting layer, an electron-transport layer, an electron-injection layer, and the like as appropriate. In this embodiment, the layer 103 containing an organic compound has a structure in which a hole-injection layer 111, a hole-transport layer 112, a light-emitting layer 113, and an electron-transport layer 114 are stacked in this order over the first electrode 102 functioning as an anode. Note that in the case where the second electrode 104 is an electrode functioning as an anode, in a layer containing an organic compound having a structure similar to the above, the hole-injection layer 111, the hole-transport layer 112, the light-emitting layer 113, and the electron-transport layer 114 are stacked in order from the second electrode 104. Materials included in the layers are specifically given below.

The hole-injection layer 111 is a layer containing a substance having a high hole-injection property. Molybdenum oxide, vanadium oxide, ruthenium oxide, tungsten oxide, manganese oxide, or the like can be used. Alternatively, the hole-injection layer 111 can be formed with a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis[4-[bis(3-methylphenyl)amino]phenyl]-N,N'-diphenyl-[1,1-biphenyl]-4,4'-diamine (abbreviation: DNTPD), a high molecular compound such as poly(ethylenedioxythiophene)/poly(styrenesulfonic acid) (PEDOT/PSS), or the like.

Alternatively, a composite material in which a substance having a high hole-transport property contains a substance having an acceptor property can be used for the hole-injection layer 111. In this specification, the composite material refers to not a material in which two materials are simply mixed but a material in the state where charge transfer between the materials can be caused by a mixture of a plurality of materials. This charge transfer includes the charge transfer that is realized only when an electric field exists.

Note that the use of such a substance having a high hole-transport property which contains a substance having an acceptor property enables selection of a material used to form an electrode regardless of its work function. In other words, besides a material having a high work function, a material having a low work function can also be used for the first electrode 102. As the substance having an acceptor property, 7,7,8,8-tetracyano-2,3,5,6-tetrafluoroquinodimethane (abbreviation: $F_4$-TCNQ), chloranil, and the like can be given. In addition, transition metal oxides can be given. Oxides of the metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable in that their electron-accepting property is high. Among these, molybdenum oxide is especially preferable in that it is stable in the air, has a low hygroscopic property, and is easily treated.

As the substance having a high hole-transport property used for the composite material, any of a variety of compounds such as aromatic amine compounds, carbazole compounds, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $10^{-6}$ cm$^2$/Vs or more is preferably used. Further, other than these substances, any substance that has a property of transporting more holes than electrons may be used. Organic compounds that can be used as the substance having a high hole-transport property in the composite material are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis[4-[bis(3-methylphenyl)amino]phenyl]-N,N'-diphenyl-[1,1-biphenyl]-4,4'-diamine (abbreviation: DNTPD), 1,3,5-tris[N-(4-diphenylaminophenyl)-N-phenylamino]benzene (abbreviation: DPA3B), and the like.

Specific examples of the carbazole compounds that can be used for the composite material are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenyl-carbazole (abbreviation: PCzPCN1), and the like.

Other examples of the carbazole compounds that can be used for the composite material are 4,4'-di(N-carbazolyl)bi-phenyl (abbreviation: CBP), 1,3,5-tris[4-(N-carbazolyl)phe-nyl]benzene (abbreviation: TCPB), 9-[4-(10-phenyl-9-an-thryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbons that can be used for the composite material are 2-tert-butyl-9,10-di(2-naph-thyl)anthracene (abbreviation: t-BuDNA), 2-tert-butyl-9,10-di(1-naphthyl)anthracene, 9,10-bis(3,5-diphenylphenyl)an-thracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetram-ethyl-9,10-di(1-naphthyl)anthracene, 2,3,6,7-tetramethyl-9,10-di(2-naphthyl)anthracene, 9,9'-bianthryl, 10,10'-diphe-nyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. Thus, an aromatic hydrocarbon having 14 to 42 carbon atoms or more and having a hole mobility of $1\times10^{-6}$ cm$^2$/Vs is more preferably used.

Note that the aromatic hydrocarbons that can be used for the composite material may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

A high molecular compound such as poly(N-vinylcarba-zole) (abbreviation: PVK), poly(4-vinyltriphenylamine) (ab-breviation: PVTPA), poly[N-(4-{N'-[4-(4-diphenylamino) phenyl]phenyl-N-phenylamino}phenyl)methacrylamide] (abbreviation: PTPDMA), or poly[N,N-bis(4-butylphenyl)-N,N-bis(phenyl)benzidine] (abbreviation: poly-TPD) can also be used.

A carbazole compound described in Embodiment 1 is also the aromatic hydrocarbon that can be used for the composite material.

The hole-transport layer 112 is a layer that contains a substance having a high hole-transport property. As the sub-stance having a high hole-transport property, the substances given as the substances having a high hole-transport property which can be used for the above composite material can also be used. Note that a detailed explanation is omitted to avoid repetition. Refer to the explanation of the composite material.

The carbazole compound represented by the general for-mula (G1) described in Embodiment 1 has an excellent hole-transport property and accordingly can be suitably used for the hole-transport layer 112. The carbazole compound having a wide energy gap can also be suitably used for a material contained in a carrier-transport layer adjacent to a light-emit-ting layer containing an emission center substance that emits blue fluorescence or green phosphorescence, without deacti-vating excitation energy of the emission center substance. Thus, a light-emitting element with high emission efficiency can be fabricated. It is needless to say that the carbazole compound can be used for a material included in a carrier-transport layer adjacent to a light-emitting layer containing an emission center substance that emits fluorescence having a longer wavelength than that of blue light or phosphorescence having a longer wavelength than that of green light or an emission center substance that emits fluorescence having a shorter wavelength than that of blue light or phosphorescence having a shorter wavelength than that of green light.

The light-emitting layer 113 is a layer containing a light-emitting substance. The light-emitting layer 113 may be formed with a film containing only a light-emitting substance or a film in which an emission center substance is dispersed into a host material.

There is no particular limitation on a material that can be used as the light-emitting substance or the emission center substance in the light-emitting layer 113, and light emitted from the material may be either fluorescence or phosphores-cence. Examples of the above light-emitting substance or emission center substance are the following substances: fluo-rescent substances such as N,N'-bis[4-(9-phenyl-9H-fluoren-9-yl)phenyl]-N,N-diphenyl-pyrene-1,6-diamine (abbrevia-tion: 1,6-FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)tripheny-lamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phe-nyl]-9H-carbazol-3-amine (abbreviation: PCAPA), perylene, 2,5,8,11: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis [N,N',N'-triphenyl-1,4-phenylenediamine] (abbreviation: DPABPA), N,9-diphenyl-N-[4-(9,10-diphenyl-2-anthryl) phenyl]-9H-carbazol-3-amine (abbreviation: 2PCAPPA), N-[4-(9,10-diphenyl-2-anthryl)phenyl]-N,N',N'-triphenyl-1, 4-phenylenediamine (abbreviation: 2DPAPPA), N,N,N',N', N",N",N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triph-enyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1, 1'-biphenyl-2-yl)-N-[4-(9H-carbazol-9-yl)phenyl]-N-phenylanthracen-2-amine (abbreviation: 2YGABPhA), N,N, 9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphe-nyltetracene (abbreviation: BPT), 2-(2-{2-[4-(dimethy-lamino)phenyl]ethenyl}-6-methyl-4H-pyran-4-ylidene)pro-panedinitrile (abbreviation: DCM1), 2-{2-methyl-6-[2-(2,3, 6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N', N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij] quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2, 6-bis[2-(8-methoxy-1,1,7,7-tetramethyl-2,3,6,7-tetrahydro- 1H,5H-benzo[ij]quinolizin-9-yl)ethenyl]-4H-pyran-4-ylidene}propanedinitrile (abbreviation: BisDCJTM); and phosphorescent substances such as bis[2-(3',5'-bistrifluoromethylphenyl)pyridinato-N,$C^{2'}$]iridium(III) picolinate (abbreviation: Ir($CF_3$ppy)$_2$(pic)), bis[2-(4',6'-difluorophenyl)pyridinato-N,$C^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato)(monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,$C^{2'}$)iridium(III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2-phenylbenzothiazolato-N,$C^{2'}$)iridium(III) acetylacetonate (abbreviation: Ir(bt)$_2$(acac)), bis[2-(2'-benzo[4,5-α]thienyl)pyridinato-N,$C^{3'}$]iridium(III) (acetylacetonate) (abbreviation: Ir(btp)$_2$(acac)), bis(1-phenylisoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(II) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphine platinum(II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)). Note that a carbazole compound in accordance with the present invention, a typical example of which is the carbazole compound represented by the general formula (G1) described in Embodiment 1, emits light in the blue to ultraviolet region, and therefore can also be used as an emission center substance.

Since the carbazole compound represented by the general formula (G1) described in Embodiment 1 has a wide energy gap and has high triplet excitation energy (a large energy difference between the triplet excited state and the ground state), the carbazole compound can be suitably used for a host material, into which an emission center substance that emits blue fluorescence or green phosphorescence is dispersed. It is needless to say that the carbazole compound can be used for a host material, into which an emission center substance that emits fluorescence having a longer wavelength than that of blue light or phosphorescence having a longer wavelength than that of green light or an emission center substance that emits fluorescence having a shorter wavelength than that of blue light or phosphorescence having a shorter wavelength than that of green light is dispersed. Since the carbazole compound has a wide energy gap and thus high triplet excitation energy, the energy of carriers that recombine in the host material can be effectively transferred to the emission center substance. Thus, a light-emitting element with high emission efficiency can be fabricated. Note that in the case where the carbazole compound represented by the general formula (G1) described in Embodiment 1 is used for a host, an emission center substance is preferably selected from, but not limited to, substances having a narrower energy gap or lower triplet excitation energy than the carbazole compound.

When the carbazole compound represented by the general formula (G1) is not used as the host material described above, any of the following substances can be used for the host material: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo[g,p]chrysene derivatives can be given, and specific examples are 9,10-diphenylanthracene (abbreviation: DPAnth), N,N-diphenyl-9-[4-(10-phenyl-9-anthryl)phenyl]-9H-carbazol-3-amine (abbreviation: CzAlPA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N'',N''',N'''-octaphenyldibenzo[g,p]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), and the like. Other than these, known materials can be given.

Note that the light-emitting layer 113 can also be a stack of two or more layers. For example, in the case where the light-emitting layer 113 is formed by stacking a first light-emitting layer and a second light-emitting layer in that order over the hole-transport layer, a substance having a hole-transport property is used for the host material of the first light-emitting layer and a substance having an electron-transport property is used for the host material of the second light-emitting layer.

In the case where the light-emitting layer having the above-described structure includes a plurality of materials, co-evaporation by a vacuum evaporation method can be used, or alternatively an inkjet method, a spin coating method, a dip coating method, or the like with a solution of the materials can be used.

The electron-transport layer 114 is a layer containing a substance having a high electron-transport property. For example, a layer containing a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10- hydroxybenzo[h]quinolinato)beryllium (abbreviation: BeBq$_2$), or bis(2-methyl-8-quinolinolato)(4-phenylphenolato)aluminum (abbreviation: BAlq). Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here mainly have an electron mobility of $10^{-6}$ cm$^2$/Vs or more. Note that other than these substances, any substance that has a property of transporting more electrons than holes may be used.

Furthermore, the electron-transport layer is not limited to a single layer and may be a stack of two or more layers containing any of the above substances.

Between the electron-transport layer and the light-emitting layer, a layer that controls transport of electron carriers may be provided. This is a layer formed by addition of a small amount of a substance having a high electron-trapping property to a material having a high electron-transport property as described above, and the layer is capable of adjusting carrier balance by suppressing transport of electron carriers. Such a structure is very effective in preventing a problem (such as a reduction in element lifetime) caused when electrons pass through the light-emitting layer.

In addition, an electron-injection layer may be provided in contact with the second electrode 104 between the electron-transport layer and the second electrode 104. For the electron-injection layer, an alkali metal, an alkaline earth metal, or a compound thereof such as lithium fluoride (LiF), cesium fluoride (CsF), or calcium fluoride (CaF$_2$) can be used. For example, a layer that is formed with a substance having an electron-transport property and contains an alkali metal, an alkaline earth metal, or a compound thereof can be used. For example, an Alq layer containing magnesium (Mg) can be used. Note that electron injection from the second electrode 104 is efficiently performed with the use of a layer that is formed with a substance having an electron-transport property and contains an alkali metal or an alkaline earth metal as the electron-injection layer, which is preferable.

For the second electrode 104, any of metals, alloys, electrically conductive compounds, and mixtures thereof which have a low work function (specifically, a work function of 3.8 eV or less) or the like can be used. Specific examples of such a cathode material include elements that belong to Groups 1 and 2 in the periodic table such as lithium (Li), cesium (Cs), magnesium (Mg), calcium (Ca), and strontium (Sr), alloys thereof (e.g., MgAg or AlLi), rare earth metals such as europium (Eu) and ytterbium (Yb), alloys thereof, and the like. However, when the electron-injection layer is provided between the second electrode 104 and the electron-transport layer, for the second electrode 104, any of a variety of conductive materials such as Al, Ag, ITO, or indium oxide-tin oxide containing silicon or silicon oxide can be used regardless of the work function. Films of these electrically conductive materials can be formed by a sputtering method, an inkjet method, a spin coating method, or the like.

Further, any of a variety of methods can be used to form the layer 103 containing an organic compound regardless whether it is a dry process or a wet process. For example, a vacuum evaporation method, an inkjet method, a spin coating method or the like may be used. Different formation methods may be used for the electrodes or the layers.

In addition, the electrode may be formed by a wet method using a sol-gel method, or by a wet method using paste of a metal material. Alternatively, the electrode may be formed by a dry method such as a sputtering method or a vacuum evaporation method.

In the light-emitting element having the above-described structure, current flows due to a potential difference between the first electrode 102 and the second electrode 104, and holes and electrons recombine in the light-emitting layer 113 which contains a substance having a high light-emitting property, so that light is emitted. That is, a light-emitting region is formed in the light-emitting layer 113.

Light emission is extracted out through one or both of the first electrode 102 and the second electrode 104. Therefore, one or both of the first electrode 102 and the second electrode 104 are light-transmitting electrodes. In the case where only the first electrode 102 is a light-transmitting electrode, light emission is extracted from the substrate side through the first electrode 102. In the case where only the second electrode 104 is a light-transmitting electrode, light emission is extracted from the side opposite to the substrate side through the second electrode 104. In the case where both the first electrode 102 and the second electrode 104 are light-transmitting electrodes, light emission is extracted from both the substrate side and the side opposite to the substrate through the first electrode 102 and the second electrode 104.

The structure of the layers provided between the first electrode 102 and the second electrode 104 is not limited to the above-described structure. Preferably, a light-emitting region where holes and electrons recombine is positioned away from the first electrode 102 and the second electrode 104 so that quenching due to the proximity of the light-emitting region and a metal used for electrodes and carrier-injection layers can be prevented. The order of stacking the layers is not limited to that in the above structure and may be the following order obtained by reversing the order shown in FIG. 1A: the second electrode, the electron-injection layer, the electron-transport layer, the light-emitting layer, the hole-transport layer, the hole-injection layer, and the first electrode from the substrate side.

Further, in order that transfer of energy from an exciton generated in the light-emitting layer can be suppressed, preferably, the hole-transport layer and the electron-transport layer which are in direct contact with the light-emitting layer, particularly a carrier-transport layer in contact with a side closer to the light-emitting region in the light-emitting layer 113 is formed with a substance having a larger energy gap than the light-emitting substance of the light-emitting layer or the emission center substance included in the light-emitting layer.

In the light-emitting element of this embodiment, since a carbazole compound described in Embodiment 1 having a large energy gap is used for the host material and/or for the electron-transport layer, efficient light emission is possible even with the emission center substance that has a large energy gap and emits blue fluorescence; accordingly, the light-emitting element can have high emission efficiency. Thus, a light-emitting element having lower power consumption can be provided. In addition, the host material or a material included in the carrier-transport layer does not easily emit light; thus, a light-emitting element capable of light emission with high color purity can be provided. Further, a carbazole compound described in Embodiment 1 has an excellent carrier-transport property; thus, a light-emitting element having low driving voltage can be provided.

In this embodiment, the light-emitting element is formed over a substrate formed of glass, plastic, or the like. With a plurality of such light-emitting elements over one substrate, a passive matrix light-emitting device can be fabricated. In addition, for example, a light-emitting element may be formed over an electrode electrically connected to a transistor which is formed over a substrate formed of glass, plastic, or the like; thus, an active matrix light-emitting device in which the transistor controls the drive of the light-emitting element can be fabricated. Note that there is no particular limitation on the structure of the transistor, which may be a staggered TFT or an inverted staggered TFT. In addition, crystallinity of a semiconductor used for the TFT is not particularly limited either; an amorphous semiconductor or a crystalline semiconductor may be used. In addition, a driver circuit formed in a TFT substrate may be formed with an n-type TFT and a p-type TFT, or with either an n-type TFT or a p-type TFT.

Embodiment 4

In this embodiment is described one mode of a light-emitting element having a structure in which a plurality of light-emitting units is stacked (hereinafter, also referred to as a stacked-type element), with reference to FIG. 1B. This light-emitting element is a light-emitting element including a plurality of light-emitting units between a first electrode and a second electrode. Each light-emitting unit can have the same structure as the layer 103 containing an organic compound which is described in Embodiment 3. In other words, the light-emitting element described in Embodiment 3 is a light-emitting element having one light-emitting unit while the light-emitting element in described Embodiment 4 is a light-emitting element having a plurality of light-emitting units.

Figure 1B:
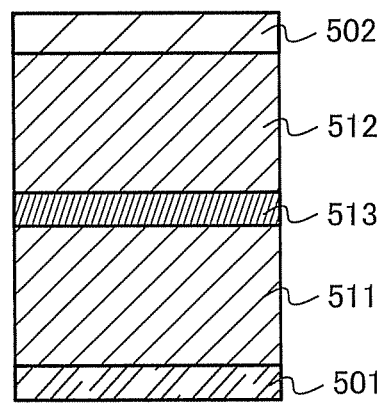

In FIG. 1B, a first light-emitting unit 511 and, a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond, respectively, to the first electrode 102 and the second electrode 104 in Embodiment 3, and materials described in Embodiment 3 can be used. Further, the structures of the first light-emitting unit 511 and the second light-emitting unit 512 may be the same or different.

The charge generation layer 513 contains a composite material of an organic compound and a metal oxide. This composite material of an organic compound and a metal oxide is the composite material described in Embodiment 3, and contains an organic compound and a metal oxide such as vanadium oxide, molybdenum oxide, or tungsten oxide. As the organic compound, any of a variety of compounds such as aromatic amine compounds, carbazole compounds, aromatic hydrocarbons, and high molecular compounds (oligomers, dendrimers, polymers, or the like) can be used. Note that as the organic compound, the one having a hole mobility of $10^{-6}$ $cm^2/Vs$ or more as an organic compound having a hole-transport property is preferably used. Further, other than these substances, any substance that has a property of transporting more holes than electrons may be used. Since a composite of an organic compound and a metal oxide is excellent in carrier-injection property and carrier-transport property, low voltage driving and low current driving can be realized.

The charge generation layer 513 may be formed in such a way that a layer containing the composite material of an organic compound and a metal oxide is combined with a layer containing another material, for example, with a layer that contains a compound selected from substances having an electron-donating property and a compound having a high electron-transport property. The charge generation layer 513 may be formed in such a way that a layer containing the composite material of an organic compound and a metal oxide is combined with a transparent conductive film.

The charge generation layer 513 provided between the first light-emitting unit 511 and the second light-emitting unit 512 may have any structure as far as electrons can be injected to a light-emitting unit on one side and holes can be injected to a light-emitting unit on the other side when a voltage is applied between the first electrode 501 and the second electrode 502. For example, in FIG. 1B, any layer can be used as the charge generation layer 513 as far as the layer injects electrons into the first light-emitting unit 511 and holes into the second light-emitting unit 512 when a voltage is applied such that the voltage of the first electrode is higher than that of the second electrode.

Although the light-emitting element having two light-emitting units is described in this embodiment, the present invention can be similarly applied to a light-emitting element in which three or more light-emitting units are stacked. By arrangement of a plurality of light-emitting units, which are partitioned by the charge-generation layer between a pair of electrodes, as in the light-emitting element of this embodiment, light emission in a high luminance region can be realized with current density kept low, thus a light-emitting element having a long lifetime can be realized. Further, in application to lighting devices, a voltage drop due to resistance of an electrode material can be reduced and accordingly light emission in a large area is possible. Moreover, a light-emitting device having low driving voltage and lower power consumption can be realized.

By making emission colors of the light-emitting units different from each other, light emission with a desired color can be obtained from the light-emitting element as a whole. For example, in a light-emitting element including two light-emitting units, the emission colors of the first light-emitting unit and the second light-emitting unit are made complementary, so that the light-emitting element which emits white light as the whole element can be obtained. Note that the term "complementary" means color relationship in which an achromatic color is obtained when colors are mixed. That is, a mixture of light emissions with complementary colors gives white light emission. The same can be applied to a light-emitting element including three light-emitting units. For example, a light-emitting element as a whole can emit white light when the emission color of the first light-emitting unit is red, the emission color of the second light-emitting unit is green, and the emission color of the third light-emitting unit is blue.

Since the light-emitting element of this embodiment includes a carbazole compound described in Embodiment 1, the light-emitting element can have high emission efficiency and low driving voltage. In addition, since light emission with high color purity which originates from the emission center substance can be obtained from the light-emitting unit including the carbazole compound, color adjustment of the light-emitting element as a whole is easy.

Note that this embodiment can be combined with any of the other embodiments as appropriate.

Embodiment 5

In this embodiment is described a light-emitting device using a light-emitting element including a carbazole compound described in Embodiment 1.

In this embodiment, an example of the light-emitting device fabricated using a light-emitting element including a carbazole compound described in Embodiment 1 is described with reference to FIGS. 3A and 3B. Note that FIG. 3A is a top view illustrating the light-emitting device and FIG. 3B is a cross-sectional view of FIG. 3A taken along the lines A-A' and B-B'. This light-emitting device includes a driver circuit portion (source driver circuit) 601, a pixel portion 602, and a driver circuit portion (gate driver circuit) 603, which are to control light emission of the light-emitting element and illustrated with dotted lines. Moreover, a reference numeral 604 denotes a sealing substrate; 625, a desiccant; 605, a sealing material; and 607, a space surrounded by the sealing material 605.

Reference numeral 608 denotes a wiring for transmitting signals to be inputted into the source driver circuit 601 and the gate driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is described with reference to FIG. 3B. The driver circuit portion and the pixel portion are formed over an element substrate 610; the source driver circuit 601, which is a driver circuit portion, and one of the pixels in the pixel portion 602 are illustrated here As the source driver circuit 601, a CMOS circuit in which an n-channel TFT 623 and a p-channel TFT 624 are combined is formed. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit may not necessarily be formed over the substrate, and the driver circuit can be formed outside, not over the substrate.

The pixel portion 602 includes a plurality of pixels including a switching II-T 611, a current controlling TFT 612, and a first electrode 613 electrically connected to a drain of the current controlling TFT 612. Note that to cover an end portion of the first electrode 613, an insulator 614 is formed, for which a positive type photosensitive acrylic resin film is used here.

In order to improve coverage, the insulator 614 is formed to have a curved surface with curvature at its upper or lower end portion. For example, in the case where positive photosensitive acrylic is used for a material of the insulator 614, only the upper end portion of the insulator 614 preferably has a curved surface with a curvature radius (0.2 μm to 3 μm). As the insulator 614, either a negative type that becomes insoluble in an etchant by irradiation with light or a positive type that becomes soluble in an etchant by irradiation with light can be used.

A layer 616 containing an organic compound and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. Note that when the stacked structure is used, the first electrode 613 has low resistance as a wiring, forms a favorable ohmic contact, and can function as an anode.

In addition, the layer 616 containing an organic compound is formed by any of a variety of methods such as an evaporation method using a shadow mask, an inkjet method, and a spin coating method. The layer 616 containing an organic compound includes a carbazole compound described in Embodiment 1. Further, another material included in the layer 616 containing an organic compound may be a low molecular compound or a high molecular compound (which may be an oligomer and a dendrimer).

As a material used for the second electrode 617, which is formed over the layer 616 containing an organic compound and functions as a cathode, a material having a low work function (e.g., Al, Mg, Li, Ca, or an alloy or compound thereof, such as MgAg, MgIn, or AlLi) is preferably used. In the case where light generated in the layer 616 containing an organic compound passes through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting element is formed with the first electrode 613, the layer 616 containing an organic compound, and the second electrode 617. The light-emitting element has the structure described in Embodiment 3 or 4. In the light-emitting device of this embodiment, the pixel portion, which includes a plurality of light-emitting elements, may include both the light-emitting element with the structure described in Embodiment 3 or 4 and a light-emitting element with a structure other than those.

Further, the sealing substrate 604 is attached to the element substrate 610 with the sealing material 605, so that a light-emitting element 618 is provided in the space 607 surrounded by the element substrate 610, the sealing substrate 604, and the sealing material 605. The space 607 may be filled with filler, and may be filled with an inert gas (such as nitrogen or argon), or the sealing material 605.

Note that an epoxy based resin is preferably used for the sealing material 605. It is desirable that such a material do not transmit moisture or oxygen as much as possible. As a material for the sealing substrate 604, a plastic substrate formed of fiberglass-reinforced plastics (FRP), polyvinyl fluoride (PVF), polyester, acrylic, or the like can be used besides a glass substrate or a quartz substrate.

As described above, the light-emitting device fabricated using the light-emitting element including a carbazole compound described in Embodiment 1 can be obtained.

The light-emitting element including a carbazole compound described in Embodiment 1 is used in the light-emitting device in this embodiment, and thus a light-emitting device having favorable characteristics can be obtained. Specifically, since a carbazole compound described in Embodiment 1 has a large energy gap and high triplet excitation energy and can suppress energy transfer from a light-emitting substance, a light-emitting element having high emission efficiency can be provided, and hence a light-emitting device having reduced power consumption can be provided. In addition, a light-emitting element having low driving voltage can be provided, and hence a light-emitting device having low driving voltage can be provided.

Figure 4A:
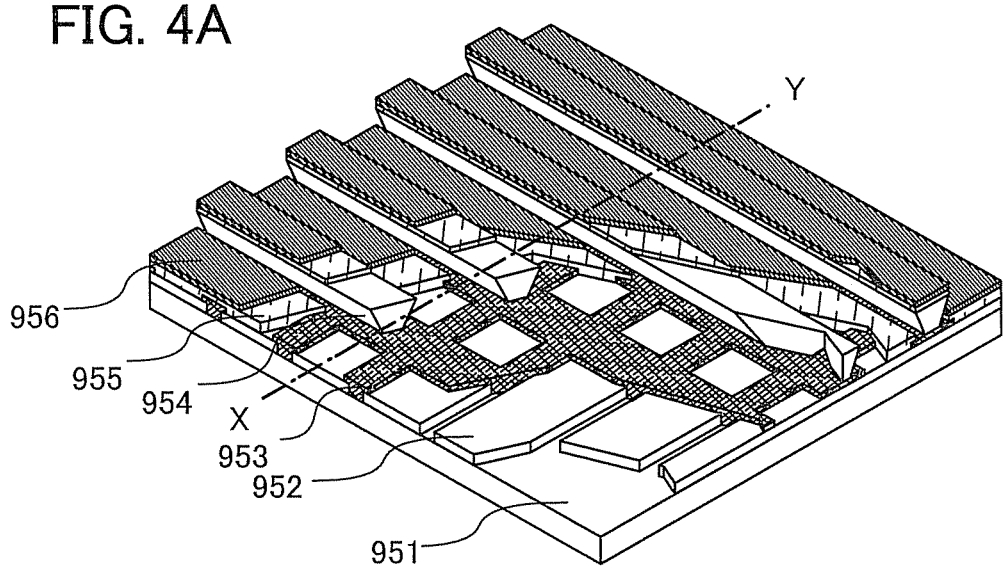
FIGS. 4A and 4B are conceptual diagrams of a passive matrix light-emitting device.
Figure 4B:
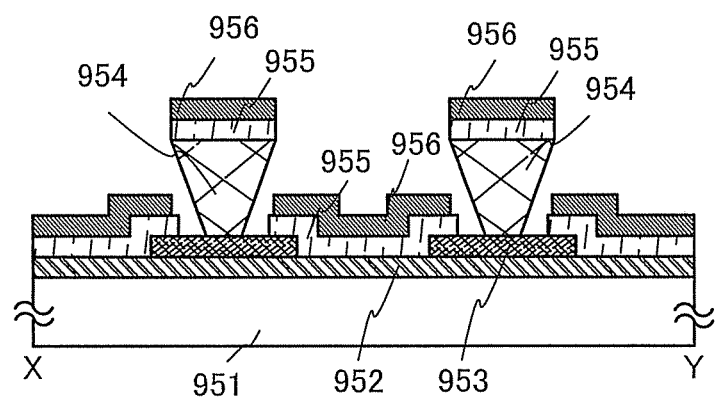

Although an active matrix light-emitting device is thus described above, a passive matrix light-emitting device is described below. FIGS. 4A and 4B illustrate a passive matrix light-emitting device fabricated in accordance with the present invention. FIG. 4A is a perspective view of the light-emitting device, and FIG. 4B is a cross-sectional view taken along line X-Y in FIG. 4A. In FIGS. 4A and 4B, over a substrate 951, a layer 955 containing an organic compound is provided between an electrode 952 and an electrode 956. An end portion of the electrode 952 is covered with an insulating layer 953. In addition, a partition layer 954 is provided over the insulating layer 953. The sidewalls of the partition layer 954 are a slope such that the distance between both sidewalls is gradually narrowed toward the surface of the substrate. In other words, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). The partition layer 954 thus provided can prevent a defect in the light-emitting element due to static charge or the like. The passive matrix light-emitting device can also be driven while power consumption is kept low, by including the light-emitting element described in Embodiment 3 or 4 which includes a carbazole compound described in Embodiment 1 and is capable of operating at low voltage. In addition, the light-emitting device can be driven while power consumption is kept low, by including the light-emitting element described in Embodiment 3 or 4 which includes a carbazole compound described in Embodiment 1 and therefore has high emission efficiency.

Since many minute light-emitting elements arranged in a matrix in the light-emitting device described above can each be controlled, the light-emitting device can be suitably used as a display device for displaying images.

Embodiment 6

In this embodiment, electronic devices each including the light-emitting element described in Embodiment 3 or 4 are described. The light-emitting element described in Embodiment 3 or 4 has reduced power consumption since it includes a carbazole compound described in Embodiment 1; accordingly, the electronic devices described in this embodiment can each include a display portion having reduced power consumption. In addition, they can have low driving voltage since the light-emitting element described in Embodiment 3 or 4 has low driving voltage.

Examples of the electronic devices to which the above light-emitting element is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pachinko machines, and the like. Specific examples of these electronic devices are described below.

Figure 5A:
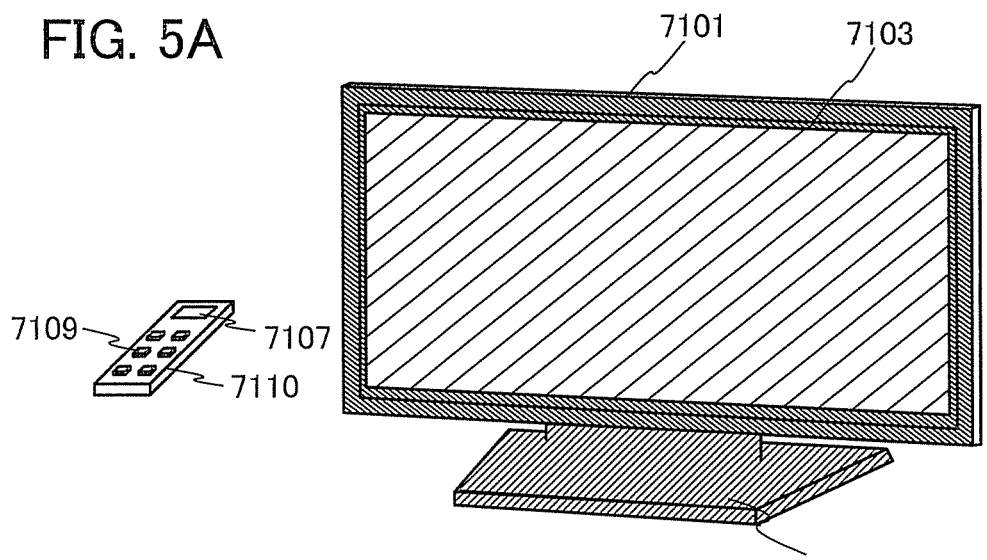
FIGS. 5A to 5D each illustrate an electronic device.

FIG. 5A illustrates an example of a television device. In the television device, a display portion 7103 is incorporated in a housing 7101. In addition, here, the housing 7101 is supported by a stand 7105. The display portion 7103 enables display of images and includes light-emitting elements which are the same as that described in Embodiment 3 or 4 and arranged in a matrix. Since each light-emitting element includes a carbazole compound described in Embodiment 1, the light-emitting elements can have high emission efficiency or have low driving voltage. Accordingly, the television device that has the display portion 7103 including the light-emitting elements can be a television device having reduced power consumption or can be a television device having low driving voltage.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the receiver, general television broadcasting can be received. Furthermore, when the television device is connected to a communication network by wired or wireless connection via the modem, one-way (from a transmitter to a receiver) or two-way (between a transmitter and a receiver, between receivers, or the like) data communication can be performed.

Figure 5B:
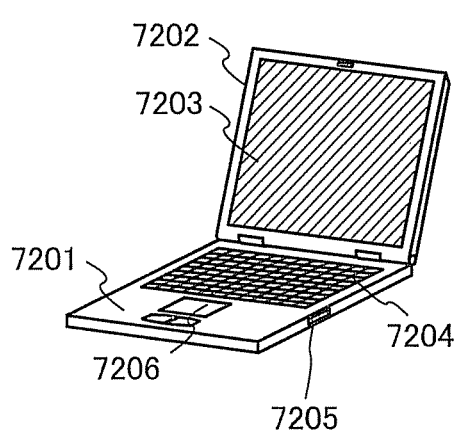

FIG. 5B illustrates a computer having a main body 7201, a housing 7202, a display portion 7203, a keyboard 7204, an external connecting port 7205, a pointing device 7206, and the like. Note that this computer is manufactured by using light-emitting elements arranged in a matrix in the display portion 7203, which are the same as that described in Embodiment 3 or 4. Since each light-emitting element includes a carbazole compound described in Embodiment 1, the light-emitting elements can have high emission efficiency or have low driving voltage. Accordingly, the computer that has the display portion 7203 including the light-emitting elements can be a computer having reduced power consumption or can be a computer having low driving voltage.

Figure 5C:
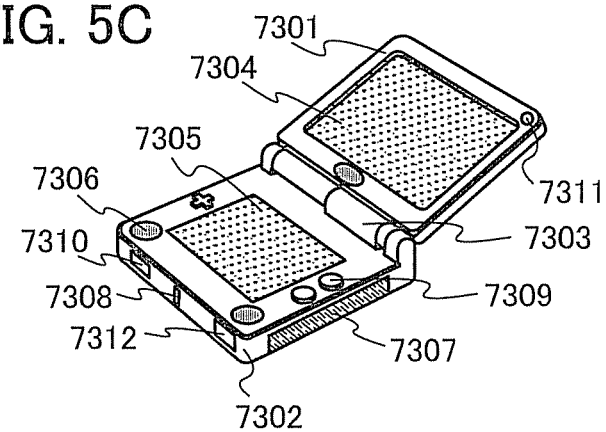

FIG. 5C illustrates a portable game machine having two housings, a housing 7301 and a housing 7302, which are connected with a joint portion 7303 so that the portable game machine can be opened or folded. A display portion 7304 including light-emitting elements which are the same as that described in Embodiment 3 or 4 and arranged in a matrix is incorporated in the housing 7301, and a display portion 7305 is incorporated in the housing 7302. In addition, the portable game machine illustrated in FIG. 5C includes a speaker portion 7306, a recording medium insertion portion 7307, an LED lamp 7308, an input unit (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable game machine is not limited to the above as far as the display portion including light-emitting elements which are the same as that described in Embodiment 3 or 4 and arranged in a matrix is used as at least either the display portion 7304 or the display portion 7305, or both, and the structure can include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above. Since the light-emitting elements used in the display portion 7304 have high emission efficiency by including a carbazole compound described in Embodiment 1, the portable game machine including the above-described display portion 7304 can be a portable game machine having reduced power consumption. Since the light-emitting elements used in the display portion 7304 has low driving voltage by including a carbazole compound described in Embodiment 1, the portable game machine can also be a portable game machine having low driving voltage.

Figure 5D:
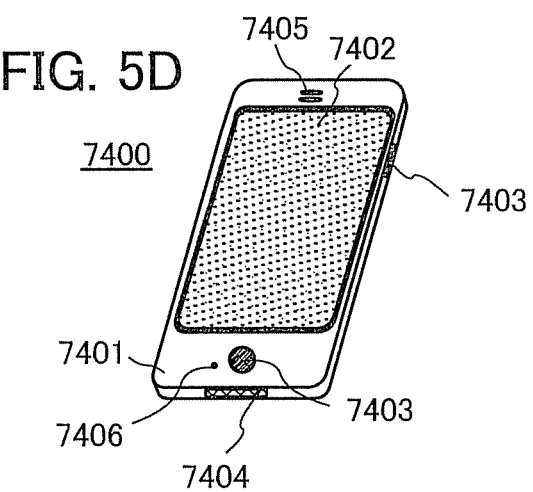

FIG. 5D illustrates an example of a cellular phone. The cellular phone 7400 is provided with operation buttons 7403, an external connection port 7404, a speaker 7405, a microphone 7406, and the like, in addition to a display portion 7402 incorporated in a housing 7401. Note that the cellular phone 7400 has the display portion 7402 including light-emitting elements which are the same as that described in Embodiment 3 or 4 and arranged in a matrix. Since each light-emitting element includes a carbazole compound described in Embodiment 1, the light-emitting elements can have high emission efficiency or have low driving voltage. Accordingly, the cellular phone that has the display portion 7402 including the light-emitting elements can be a cellular phone having reduced power consumption or can be a cellular phone having low driving voltage.

When the display portion 7402 of the cellular phone illustrated in FIG. 5D is touched with a finger or the like, data can be input into the cellular phone. In this case, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a character input mode mainly for inputting characters is selected for the display portion 7402 so that characters displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone, display on the screen of the display portion 7402 can be automatically changed by determining the orientation of the cellular phone (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on the kinds of images displayed on the display portion 7402. For example, when a signal for an image to be displayed on the display portion is for moving images, the screen mode is switched to the display mode; when the signal is for text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, so that personal authentication can be performed. Furthermore, by use of a backlight or a sensing light source that emits a near-infrared light for the display portion, an image of a finger vein, a palm vein, or the like can also be taken.

Note that the structure described in this embodiment can be combined with any of the structures described in Embodiments 1 to 5 as appropriate.

As described above, the application range of the light-emitting device having the light-emitting element described in Embodiment 3 or 4 which includes a carbazole compound described in Embodiment 1 is wide so that this light-emitting device can be applied to electronic devices in a variety of fields. By use of a carbazole compound described in Embodiment 1, an electronic device having reduced power consumption or an electronic device having low driving voltage can be obtained.

The light-emitting element including a carbazole compound described in Embodiment 1 can also be used for a lighting device. One mode of application of the light-emitting element including a carbazole compound described in Embodiment 1 to a lighting device is described with reference to FIG. 6. Note that the lighting device includes the light-emitting element including a carbazole compound described in Embodiment 1 as a light irradiation unit and at least includes an input-output terminal portion that supplies a current to the light-emitting element. Further, the light-emitting element is preferably shielded from the outside atmosphere (especially water and oxygen) by sealing.

Figure 6:
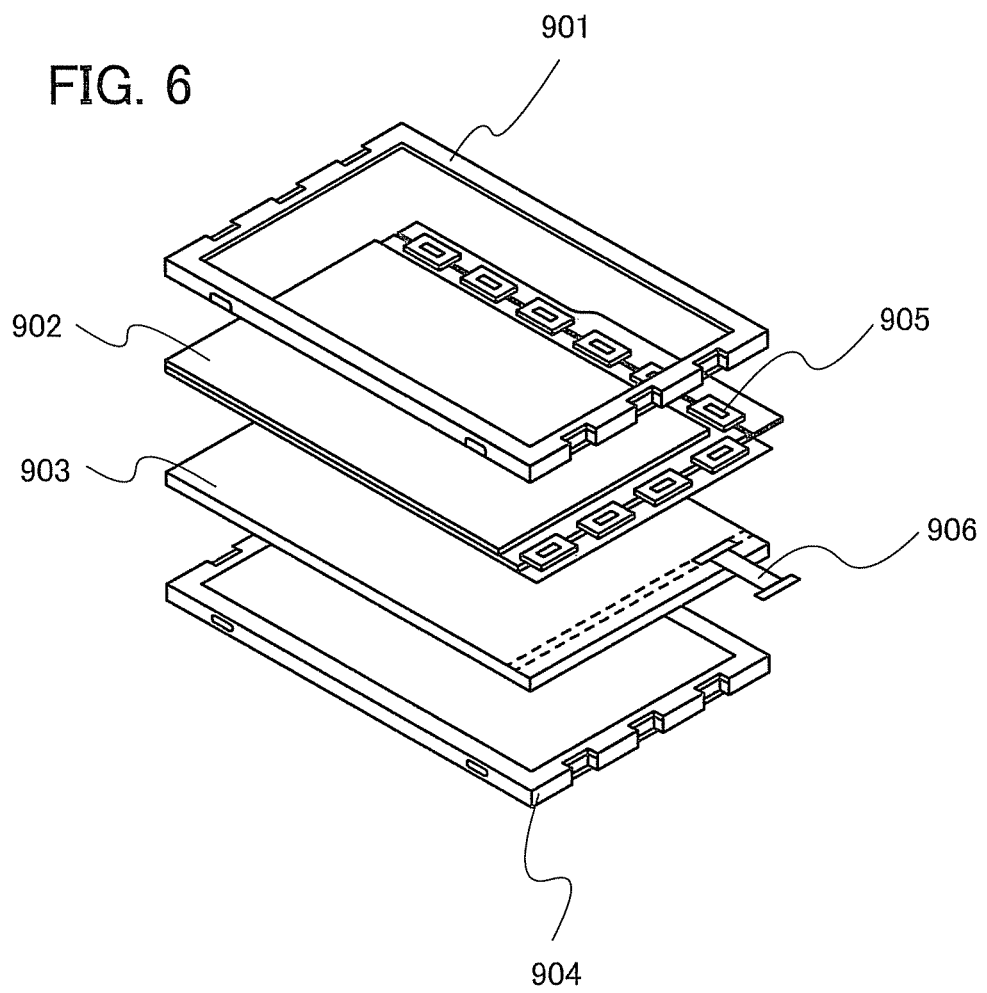
FIG. 6 illustrates a light source device.

FIG. 6 illustrates an example of a liquid crystal display device using the light-emitting element including a carbazole compound described in Embodiment 1 for a backlight. The liquid crystal display device illustrated in FIG. 6 includes a housing 901, a liquid crystal layer 902, a backlight 903, and a housing 904. The liquid crystal layer 902 is connected to a driver IC 905. The light-emitting element including a carbazole compound described in Embodiment 1 is used in the backlight 903, to which a current is supplied through a terminal 906.

The light-emitting element including a carbazole compound described in Embodiment 1 is used for the backlight of the liquid crystal display device, and thus a backlight having reduced power consumption can be obtained. In addition, use of the light-emitting element including a carbazole compound described in Embodiment 1 enables manufacture of a planar-emission lighting device and further a larger-area planar-emission lighting device; therefore, the backlight can be a larger-area backlight, and the liquid crystal display device can also be a larger-area device. Furthermore, the backlight using the light-emitting element including a carbazole compound described in Embodiment 1 can be thinner than a conventional one; accordingly, the display device can also be thinner.

Figure 7:
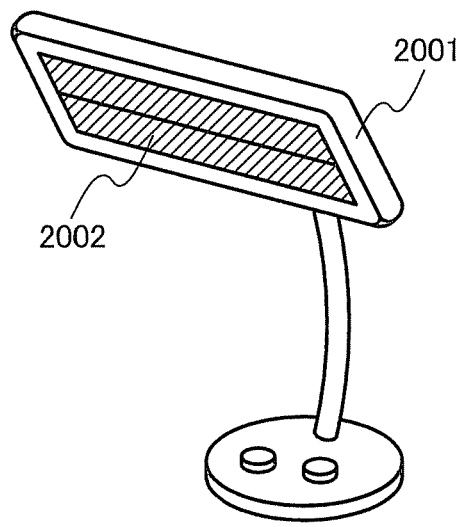
FIG. 7 illustrates a lighting device.

FIG. 7 illustrates an example in which the light-emitting element including a carbazole compound described in Embodiment 1 is used for a table lamp which is a lighting device. The table lamp illustrated in FIG. 7 includes a housing 2001 and a light source 2002, and the light-emitting element including a carbazole compound described in Embodiment 1 is used for the light source 2002.

Figure 8:
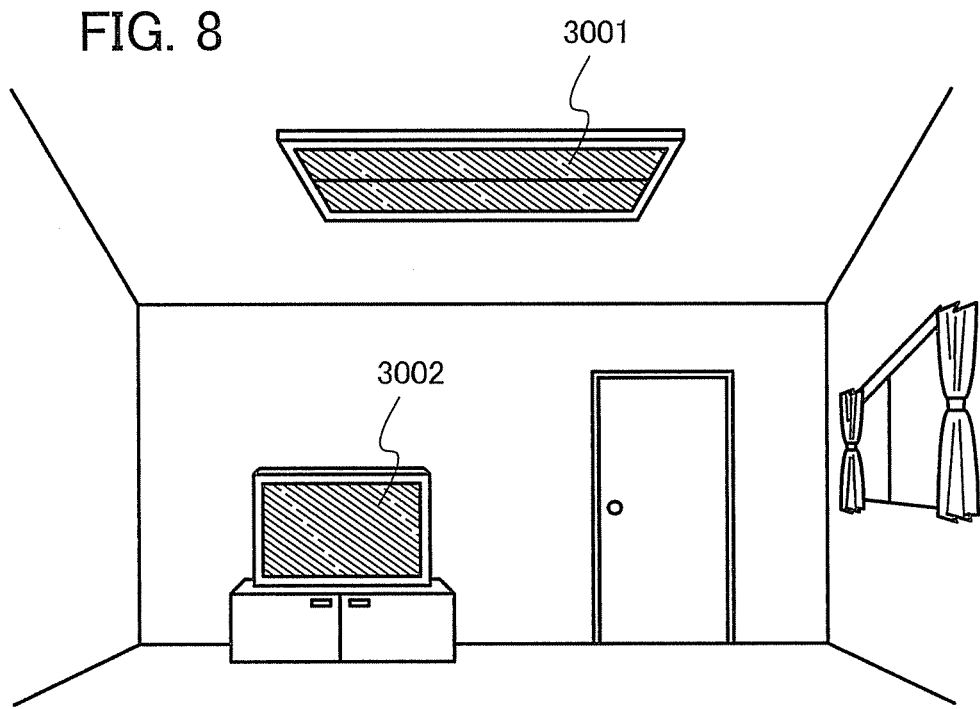
FIG. 8 illustrates lighting devices.

FIG. 8 illustrates an example in which the light-emitting element including a carbazole compound described in Embodiment 1 is used for indoor lighting devices 3001 and 3002. Since the light-emitting element including a carbazole compound described in Embodiment 1 has reduced power consumption, a lighting device that has reduced power consumption can be obtained. Further, since the light-emitting element including a carbazole compound described in Embodiment 1 can have a large area, the light-emitting element can be used for a large-area lighting device. Furthermore, since the light-emitting element including a carbazole compound described in Embodiment 1 is thin, a lighting device having a reduced thickness can be fabricated.

The light-emitting element including a carbazole compound described in Embodiment 1 can also be used for an automobile windshield or dashboard. One mode in which the light-emitting elements described in Embodiment 1 are used for an automobile windshield and an automobile dashboard is illustrated in FIG. 9. Light-emitting devices 5000 to 5005 each include the light-emitting element including a carbazole compound described in Embodiment 1.

The light-emitting device 5000 and the light-emitting device 5001 are display devices which are provided in the automobile windshield and in which the light-emitting elements described in Embodiment 1 are incorporated. The light-emitting elements described in Embodiment 1 can be formed into so-called see-through display devices, through which the opposite side can be seen, by including a first electrode and a second electrode formed with electrodes having a light-transmitting property. Such see-through display devices can be provided even in the automobile windshield, without hindering the vision. Note in the case where a transistor for driving the light-emitting element is provided, a transistor having a light-transmitting property, such as an organic transistor using an organic semiconductor material or a transistor using an oxide semiconductor, is preferably used.

The light-emitting device 5002 is a display device which is provided in a pillar portion and in which the light-emitting element including a carbazole compound described in Embodiment 1 is incorporated. The light-emitting device 5002 can compensate for the view hindered by the pillar portion by showing an image taken by an imaging element provided in the automobile body. Similarly, the light-emitting device 5003 provided in the dashboard can compensate for the view hindered by the automobile body by showing an image taken by an imaging element provided in the outside of the automobile body, which leads to elimination of blind areas and enhancement of safety. Showing an image so as to compensate for the area which a driver cannot see, makes it possible for the driver to confirm safety easily and comfortably.

The light-emitting device 5004 and the light-emitting device 5005 can provide a variety of kinds of information such as information of navigation, speedometer, tachometer, mileage (travel distance), fuel meter, gearshift indicator, and air condition. The content or layout of the display can be changed freely by a user as appropriate. Further, such information can also be shown in the light-emitting devices 5000 to 5003. Note that the light-emitting devices 5000 to 5005 can also be used as lighting devices.

By including a carbazole compound described in Embodiment 1, the light-emitting element including the carbazole compound has low driving voltage and lower power consumption. When a number of large screens are provided, load on a battery can be reduced, which provides comfortable use.

The light-emitting device and the lighting device each using a light-emitting element including a carbazole compound described in Embodiment 1 can be suitably used as an in-vehicle light-emitting device or lighting device.

Example 1

Synthesis Example 1

In this example is specifically described a method of synthesizing 3,3'-bis(dibenzothiophen-4-yl)-N,N'-(1,3-phenylene)bicarbazole (abbreviation: mDBTCz2P-II), which is represented by the structural formula (100) in Embodiment 1, and characteristics of this compound. A structural formula of mDBTCz2P-II is shown below.

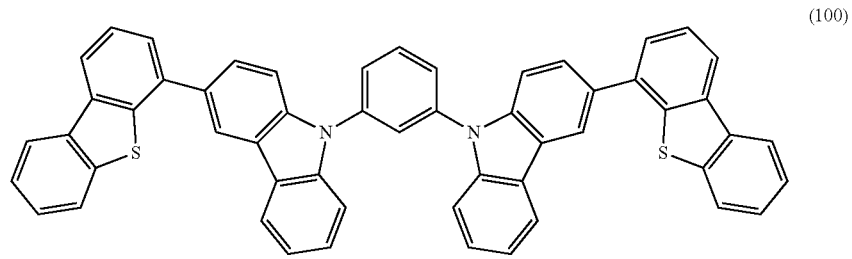 [SMILES: c1cc(-n2c3ccccc3c3cc(-c4cccc5c4sc4ccccc45)ccc32)cc(-n2c3ccccc3c3cc(-c4cccc5c4sc4ccccc45)ccc32)c1]

(100)

Step 1: Synthesis of
3-(Dibenzothiophen-4-yl)-9H-carbazole

Into a 200 mL three-neck flask were placed 3.0 g (12 mmol) of 3-bromocarbazole, 2.8 g (12 mmol) of dibenzothiophene-4-boronic acid, and 0.15 g (0.5 mol) of tri(ortho-tolyl)phosphine, and the air in the flask was replaced with nitrogen. To this mixture were added 40 mL of toluene, 40 mL of ethanol, and 15 mL (2.0 mol/L) of an aqueous solution of potassium carbonate. In the flask, the mixture was degassed by being stirred under reduced pressure. After the degassing, the air in the system was replaced with nitrogen, and 23 mg (0.10 mmol) of palladium(II) acetate was added to this mixture, and then the mixture was refluxed at 80° C. for 4 hours. After the reflux, the mixture was cooled to room temperature, whereby a solid was precipitated. About 100 mL of toluene was added to the mixture in which the solid was precipitated, and the resulting mixture was heated and stirred, so that the precipitated solid was dissolved. While kept hot, the obtained suspension was filtered through Celite (produced by Wako Pure Chemical Industries, Ltd., Catalog No. 531-16855), Florisil (produced by Wako Pure Chemical Industries, Ltd., Catalog No. 540-00135), and alumina. The solid obtained by concentration of the obtained filtrate was recrystallized from toluene, so that 3.4 g of a white solid which was the object of the synthesis was obtained in 79% yield. The reaction scheme of Step 1 is illustrated in the following scheme (a-1).

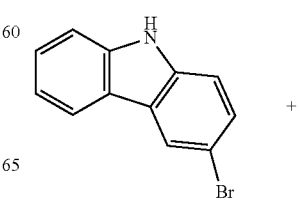

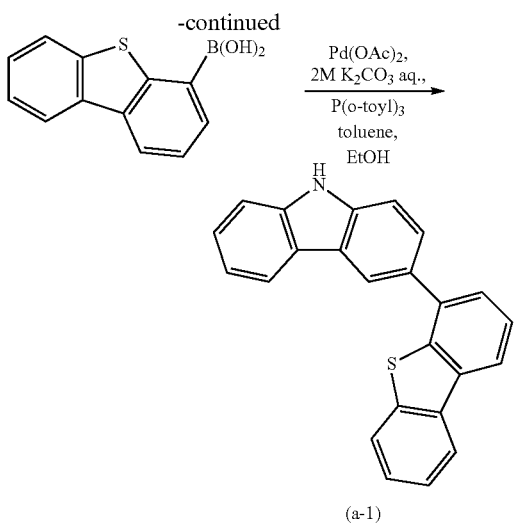

(a-1)

Step 2: Synthesis of 3,3'-Bis(dibenzothiophen-4-yl)-N,N-(1,3-phenylene)bicarbazole (abbreviation: mDBTCz2P-II)

Into a 200 mL three-neck flask were placed 1.2 g (5.0 mmol) of 1,3-dibromobenzene and 3.5 g (10 mmol) of 3-(dibenzothiophen-4-yl)-9H-carbazole (abbreviation: DBTCz), and the air in the flask was replaced with nitrogen. To this mixture were added 40 mL of toluene, 0.10 mL of tri(tert-butyl)phosphine (a 10 wt % hexane solution), and 0.98 g (10 mmol) of sodium tert-butoxide. This mixture was degassed while being stirred under reduced pressure. After this mixture was stirred at 80° C. and dissolution of materials was confirmed, 61 mg (0.11 mmol) of bis(dibenzylideneacetone)palladium(0) was added thereto. This mixture was refluxed at 110° C. for 55 hours. After the reflux, the mixture was cooled to room temperature, and the precipitated white solid was collected by suction filtration. The obtained solid was washed with water and toluene to give 1.2 g of a white solid which was the object of the synthesis in 70% yield. The synthesis scheme of Step 2 is illustrated in the following scheme (a-2).

Using a train sublimation method, 1.1 g of the obtained white solid was purified by sublimation. In the purification by sublimation, the white solid was heated at 350° C. under a pressure of 2.8 Pa with a flow rate of argon gas of 10 mL/min. After the purification by sublimation, 0.89 g of a colorless transparent solid was obtained in a yield of 83%.

Figure 10A:
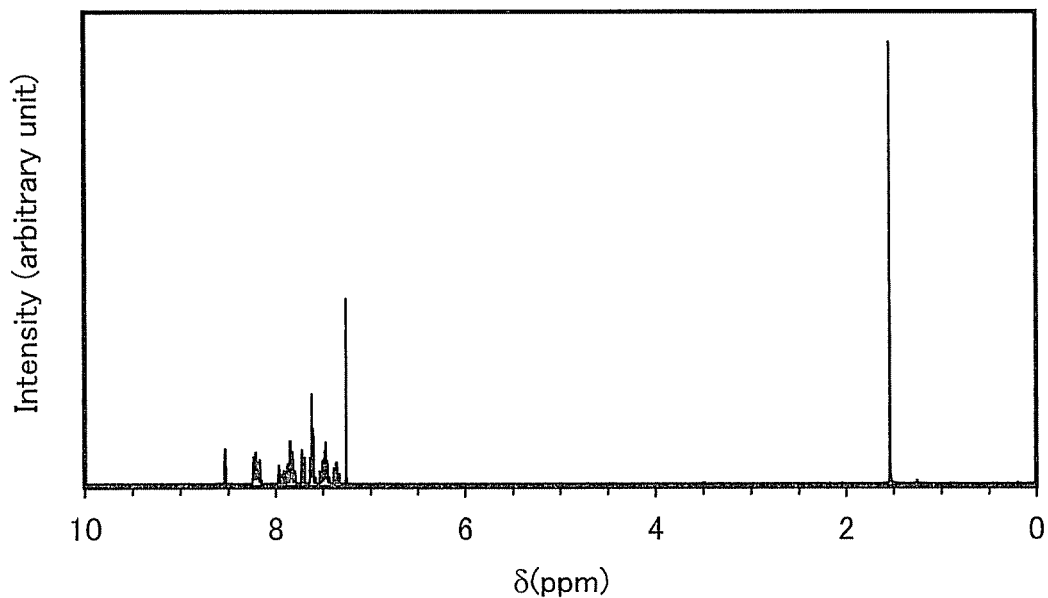
FIGS. 10A and 10B are NMR charts of mDBTCz2P-II.
Figure 10B:
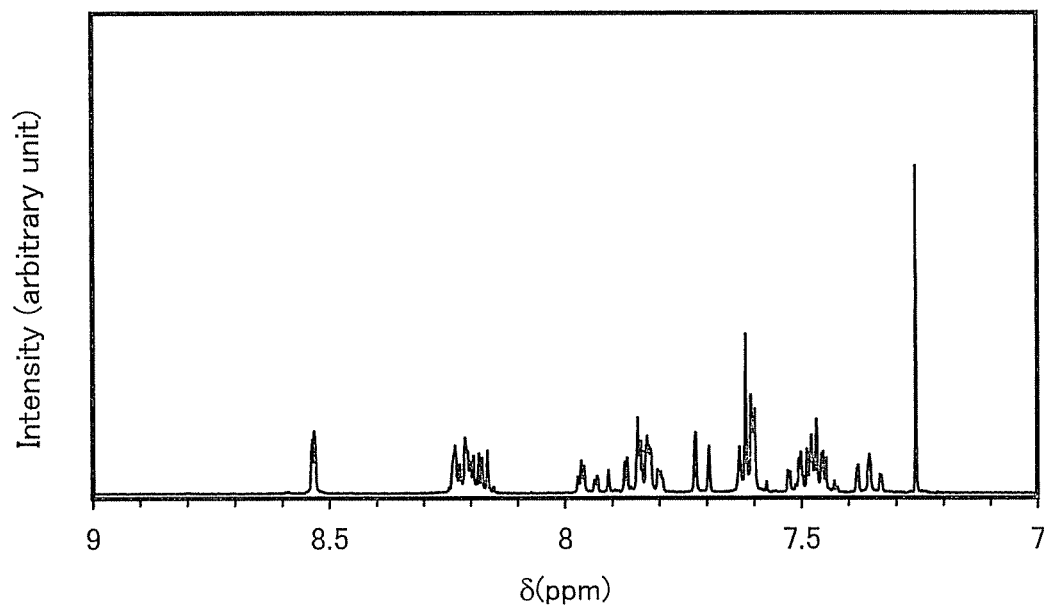

This compound was subjected to nuclear magnetic resonance (NMR) spectroscopy. The obtained NMR charts are shown in FIGS. 10A and 10B. Note that FIG. 10B is a chart where the range of from 7 ppm to 9 ppm in FIG. 10A is enlarged. In addition, $^1$H NMR data of the obtained compound is shown below.

$^1$H NMR (CDCl$_3$, 300 MHz): δ (ppm)=7.36 (td, $J_1$=0.9 Hz, $J_2$=7.8 Hz, 2H), 7.43-7.53 (m, 6H), 7.58-7.63 (m, 6H), 7.71 (d, J=8.7 Hz, 2H), 7.80-7.97 (m, 8H), 8.15-8.24 (m, 6H), 8.53 (d, J=1.5 Hz, 2H)

Thus, the solid obtained in this synthesis example was confirmed to be 3,3'-bis(dibenzothiophen-4-yl)-N,N'-(1,3-phenylene)bicarbazole (abbreviation: mDBTCz2P-II).

Physical Properties of mDBTCz2P-II

Figure 11A:
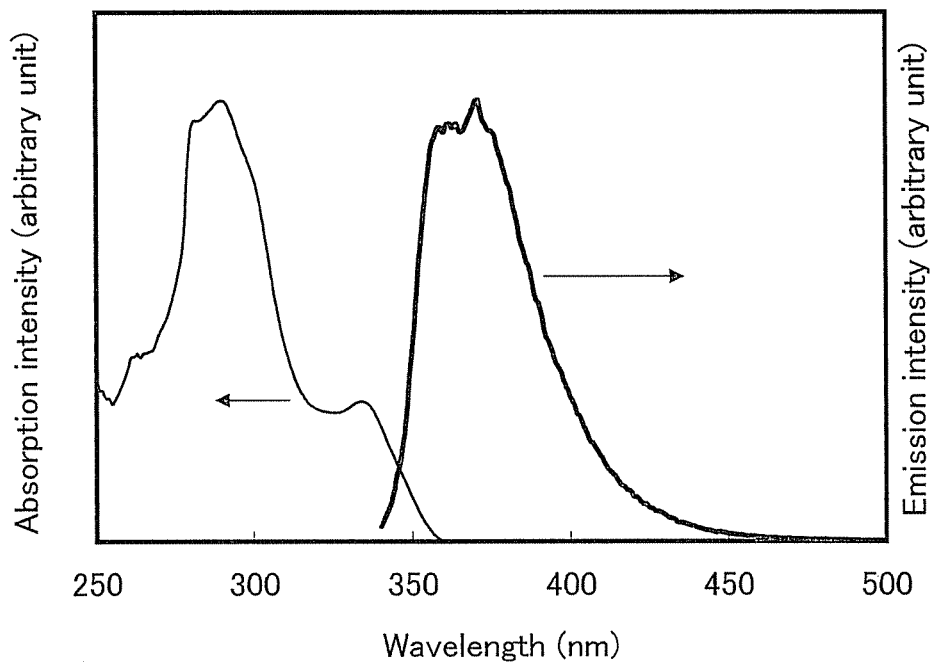
FIGS. 11A and 11B each show an absorption and emission spectra of mDBTCz2P-II.
Figure 11B:
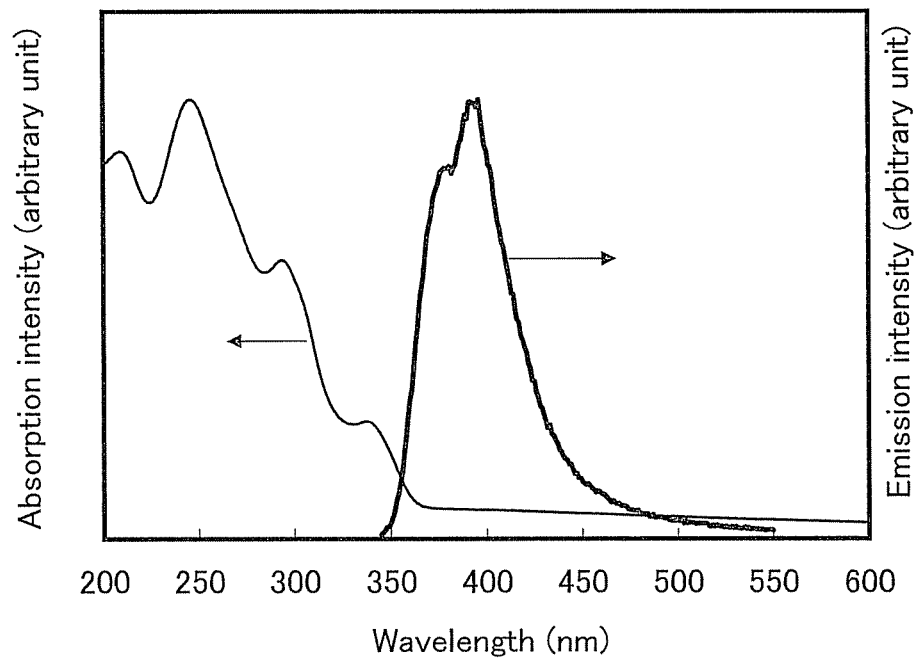

Further, an absorption and emission spectra of mDBTCz2P-II in a toluene solution of mDBTCz2P-II are shown in FIG. 11A, and an absorption and emission spectra of a thin film of mDBTCz2P-II are shown in FIG. 11B. An ultraviolet-visible spectrophotometer (V-550, produced by JASCO Corporation) was used for the measurements of the spectra. The spectra of the toluene solution were measured with a toluene solution of mDBTCz2P-II put in a quartz cell. The spectra of the thin film were measured with a sample prepared by evaporation of mDBTCz2P-II over a quartz substrate. Note that in the case of the absorption spectrum of the toluene solution, the spectrum obtained by subtraction of the absorption spectra of quartz and toluene from the measured spectra is shown in the drawing, and in the case of the absorption spectrum of the thin film, the spectrum obtained by subtraction of that of the quartz substrate from the measured spectra is shown in the drawing.

FIG. 11A shows that the absorption peak wavelengths of mDBTCz2P-II in the toluene solution of mDBTCz2P-II were around 332 nm, 288 inn and 281 nm, and the emission peak

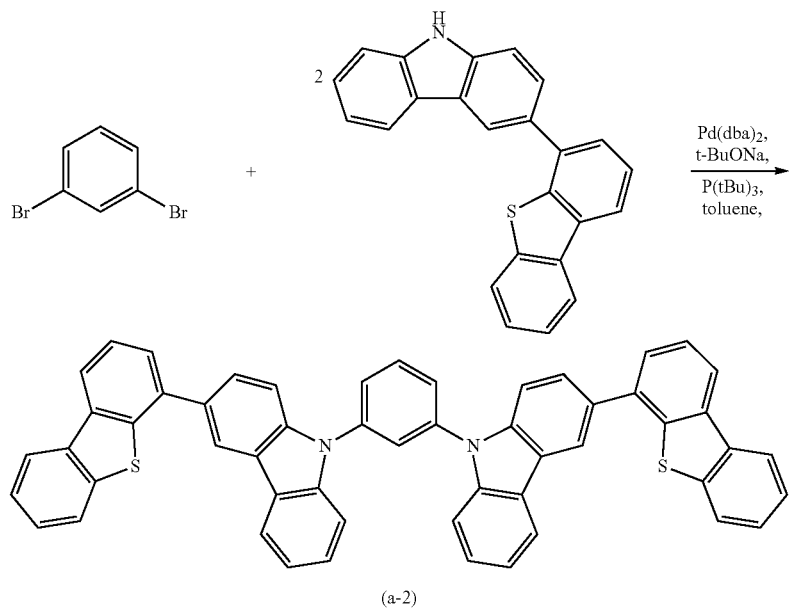

(a-2)

wavelength thereof was around 370 nm (at an excitation wavelength of 334 nm). Further, FIG. 11B shows that the absorption peak wavelengths of the thin film of mDBTCz2P-II were around 337 nm, 294 nm, 246 nm and 209 nm, and the emission peak wavelengths thereof were around 393 nm and 380 nm (at an excitation wavelength of 342 nm).

Further, the ionization potential of a thin film of mDBTCz2P-II was measured by a photoelectron spectrometer (AC-2, produced by Riken Keiki, Co., Ltd.) in the air. The obtained value of the ionization potential was converted to a negative value, so that the HOMO level of mDBTCz2P-II was −5.93 eV. From the data of the absorption spectra of the thin film in FIG. 11B, the absorption edge of mDBTCz2P-II, which was obtained from a Tauc plot with an assumption of direct transition, was 3.45 eV. Therefore, the optical energy gap of mDBTCz2P-II in the solid state was estimated at 3.45 eV; from the values of the HOMO level obtained above and this energy gap, the LUMO level of mDBTCz2P-II was able to be estimated at −2.48 eV. It was thus found that mDBTCz2P-II had a wide energy gap of 3.45 eV in the solid state.

Example 2

In this example is described a light-emitting element in which 3,3'-bis(dibenzothiophen-4-yl)-N,N'-(1,3-phenylene)bicarbazole (abbreviation: mDBTCz2P-II) (abbreviation: mDBTCz2P-II, structural formula (100)), which is a carbazole compound described in Embodiment 1, was used for a material of a hole-transport layer adjacent to a light-emitting layer using an emission center substance that emits blue fluorescence. Note that in this example, mDBTCz2P-II was also used for a composite material with molybdenum oxide in a hole-injection layer.

The molecular structures of organic compounds used in this example are represented by structural formulae (i) to (iv) and (100) below. In the element structure in FIG. 1A, an electron-injection layer is provided between an electron-transport layer 114 and a second electrode 104.

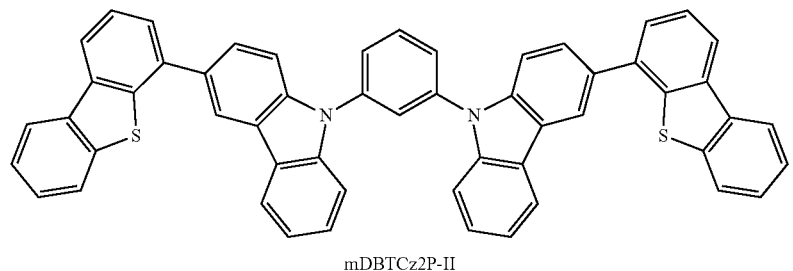

mDBTCz2P-II (100)

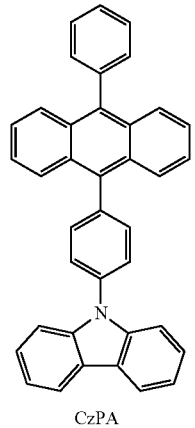

CzPA (i)

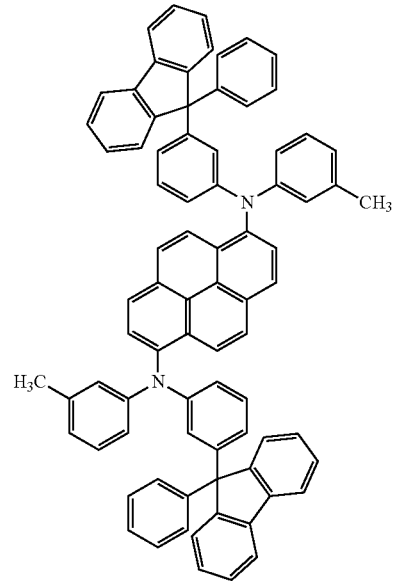

1,6mMemFLPAPrn (ii)

(iii)

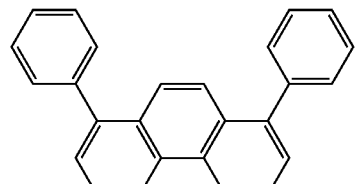

BPhen

Fabrication of Light-Emitting Element 1

First, a glass substrate 101, over which a film of indium tin oxide containing silicon (ITSO) was formed to a thickness of 110 nm as the first electrode 102, was prepared. A surface of the ITSO film is covered with an insulating film, and a 2 mm square portion of the surface is exposed in order that a light-emitting area be set to 2 mm×2 mm. As pretreatment for forming the light-emitting elements over the substrate, the surface of the substrate was washed with water and baked at 200° C. for one hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed to a holder provided in the vacuum evaporation apparatus such that the surface of the substrate 101 over which the ITSO film was formed faced downward.

After the pressure in the vacuum evaporation apparatus was reduced to $10^{-4}$ Pa, 3,3'-bis(dibenzothiophen-4-yl)-N,N'-(1,3-phenylene)bicarbazole (abbreviation: mDBTCz2P-II), which is a carbazole compound described in Embodiment 1 and represented by the above structural formula (100), and molybdenum(VI) oxide were co-evaporated so that the weight ratio of mDBTCz2P-II to molybdenum oxide was 2:1; thus, a hole-injection layer 111 was formed. The thickness thereof was set to 50 nm. Note that the co-evaporation is an evaporation method in which a plurality of different substances is concurrently vaporized from the respective different evaporation sources.

Next, a film of mDBTCz2P-II was evaporated to a thickness of 10 nm, thereby forming a hole-transport layer 112.

Further, over the hole-transport layer 112, 9-[4-(10-phenyl-9-anthryl)phenyl]-9H-carbazole (abbreviation: CzPA) represented by the above structural formula (I) and N,N'-bis (3-methylphenyl)-N,N'-bis[3-(9-phenyl-9H-fluoren-9-yl) phenyl]-pyrene-1,6-diamine (abbreviation: 1,6-MemFLPA-Prn) represented by the above structural formula (ii) were evaporated to a thickness of 30 nm so that the weight ratio of CzPA to 1,6mMemFLPAPrn were 1:0.04. Thus, a light-emitting layer 113 was fainted.

Next, CzPA was evaporated to a thickness of 10 nm, and then bathophenanthroline (abbreviation: BPhen) represented by the above structural formula (iii) was evaporated to a thickness of 15 nm, thereby fanning the electron-transport layer 114.

Further, lithium fluoride was evaporated to a thickness of 1 nm on over the electron-transport layer 114, thereby fowling the electron-injection layer. Lastly, an aluminum film was formed to a thickness of 200 nm as the second electrode 104 functioning as a cathode. Thus, the light-emitting element 1 was completed. Note that in the above evaporation processes, evaporation was all performed by a resistance heating method.

Operation Characteristics of Light-Emitting Element 1

The light-emitting element 1 thus obtained was sealed in a glove box under a nitrogen atmosphere without being exposed to the air. Then, the operation characteristics of this light-emitting element were measured. Note that the measurements were carried out at room temperature (in an atmosphere kept at 25° C.).

Figure 12:
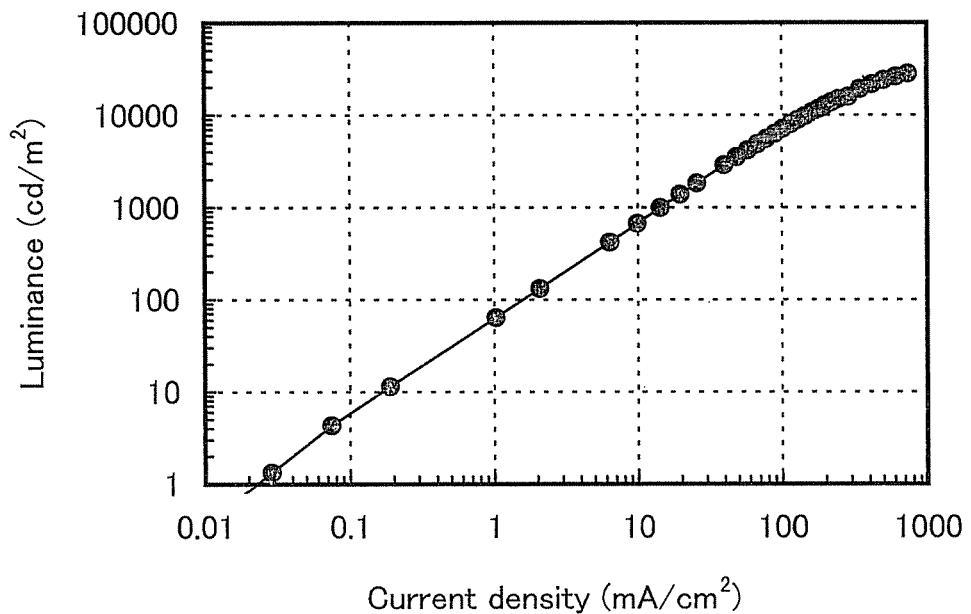
FIG. 12 shows luminance versus current density characteristics of a light-emitting element 1.
Figure 13:
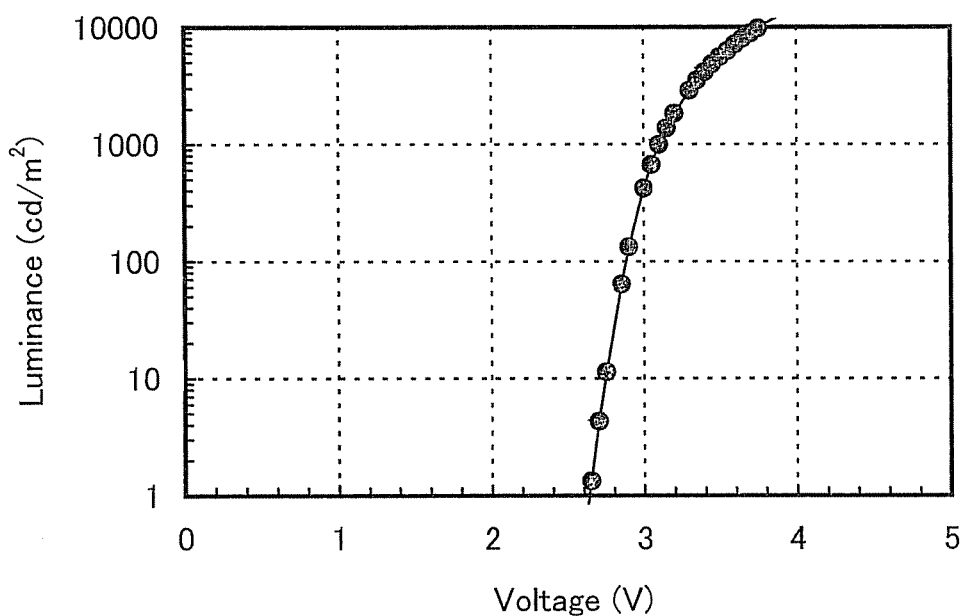
FIG. 13 shows luminance versus voltage characteristics of the light-emitting element 1.
Figure 14:
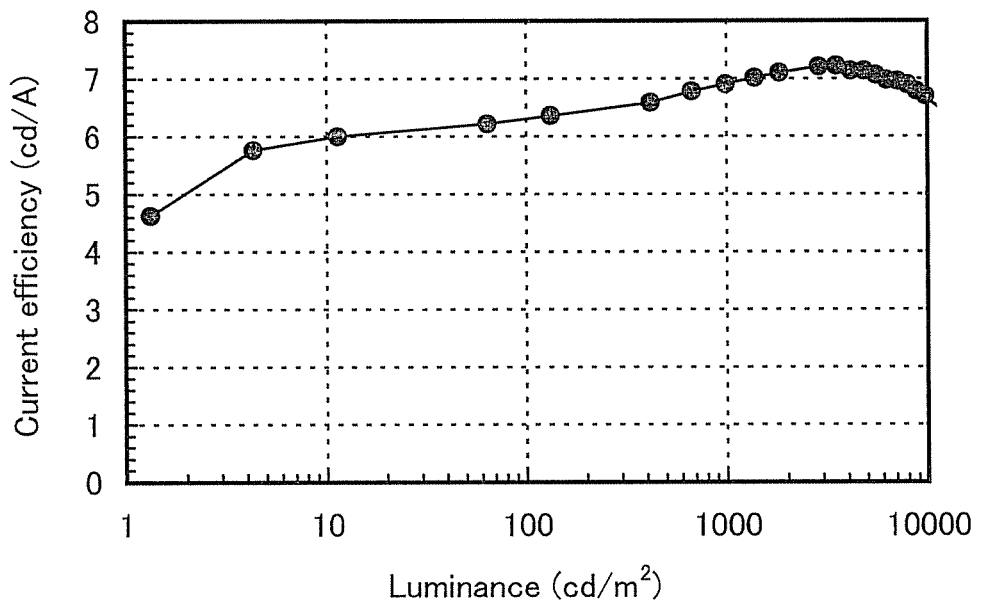
FIG. 14 shows current efficiency versus luminance characteristics of the light-emitting element 1.
Figure 15:
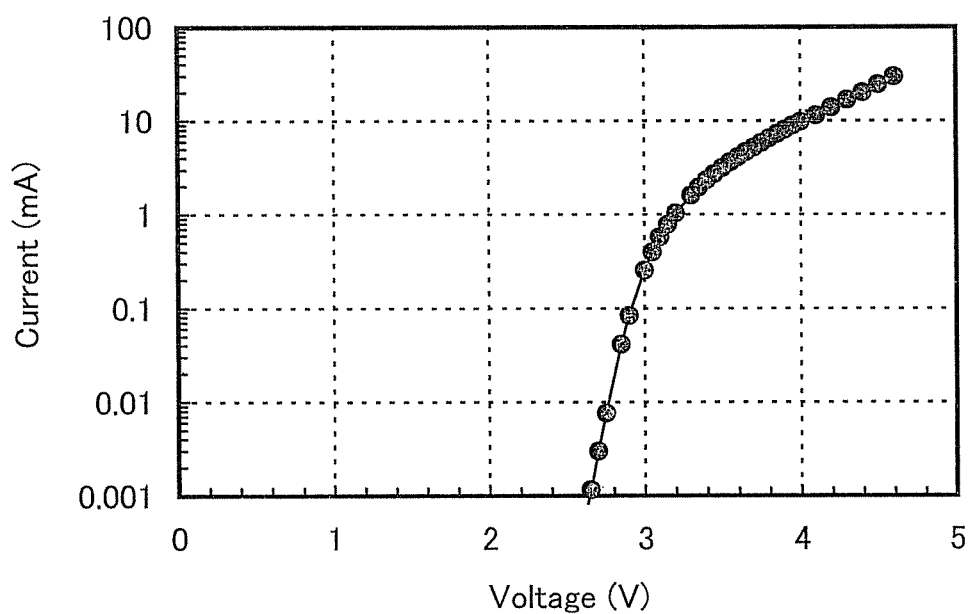
FIG. 15 shows current versus voltage characteristic of the light-emitting element 1.

FIG. 12 shows luminance versus current density characteristics of the light-emitting element 1, FIG. 13 shows its luminance versus voltage characteristics, FIG. 14 shows its current efficiency versus luminance characteristics, and FIG. 15 shows its current versus voltage characteristics. In FIG. 12, the vertical axis represents luminance ($cd/m^2$) and the horizontal axis represents current density ($mA/cm^2$). In FIG. 13, the vertical axis represents luminance ($cd/m^2$) and the horizontal axis represents voltage (V). In FIG. 14, the vertical axis represents current efficiency (cd/A) and the horizontal axis represents luminance ($cd/m^2$). In FIG. 15, the vertical axis represents current (mA) and the horizontal axis represents voltage (V).

FIG. 12 shows the favorable luminance versus current efficiency characteristics of the light-emitting element, in which the carbazole compound represented by the general formula (G1) was used for a hole-transport material adjacent to a light-emitting layer exhibiting blue fluorescence and for a hole-injection layer (as a composite material with molybdenum oxide). Thus, the element is found to have high emission efficiency. Since CzPA as the host material of the light-emitting layer in the light-emitting element 1 is a material having a relatively high electron-transport property, a light-emitting region in the light-emitting layer is probably localized on the hole-transport layer side. The high emission efficiency of the light-emitting element despite such a state results from the wide energy gap of the carbazole compound represented by the general formula (G1). In other words, since mDBTCz2P-II, which is a carbazole compound described in Embodiment 1, has a wide energy gap, even when it is used for the hole-transport layer adjacent to the emission center substance that emits blue fluorescence, a reduction in emission efficiency is suppressed without transfer of excitation energy to the hole-transport layer.

In addition, FIG. 13 shows the favorable luminance versus voltage characteristics of the light-emitting element, in which the carbazole compound represented by the general formula (G1) was used for the host material for the light-emitting layer exhibiting blue fluorescence. Thus, the element is found to have low driving voltage. This indicates that the carbazole compound represented by the general formula (G1) has an excellent carrier-transport property and the composite material including the carbazole compound represented by the general formula (G1) has an excellent carrier-injection property.

Figure 16:
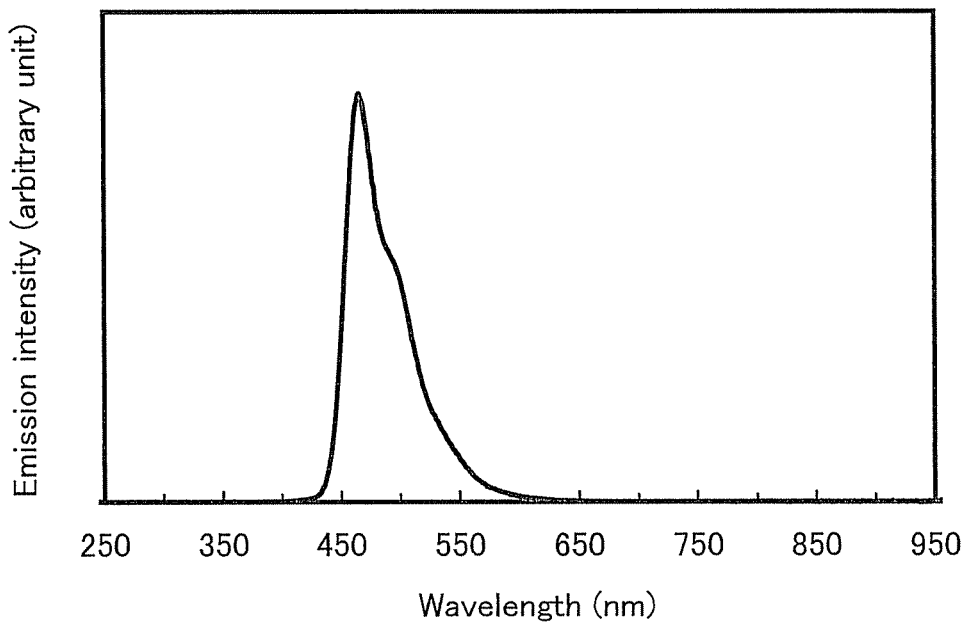
FIG. 16 shows an emission spectrum of the light-emitting element 1.

FIG. 16 shows an emission spectrum obtained when a current of 1 mA was made to flow in the light-emitting element 1. In FIG. 16, the vertical axis represents emission intensity (arbitrary unit) and the horizontal axis represents wavelength (nm). The emission intensity is shown as a value relative to the greatest emission intensity assumed to be 1. FIG. 16 indicates that the light-emitting element 1 emits blue light that originates from 1,6mMemFLPAPrn, which was the emission center substance.

Figure 17:
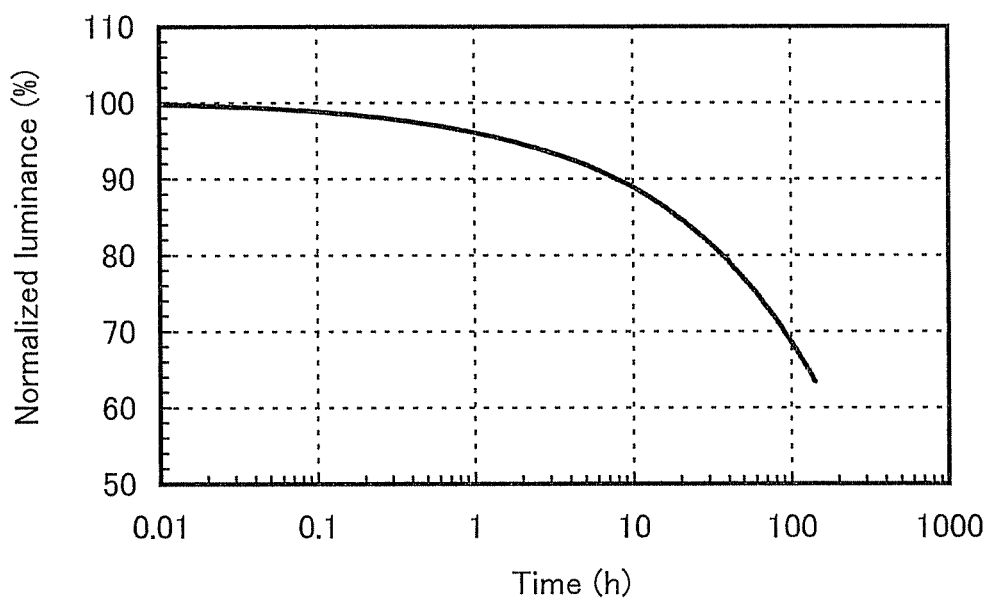
FIG. 17 shows normalized luminance versus time characteristics of the light-emitting element 1.

Next, with an initial luminance set to 1000 $cd/m^2$, the light-emitting element 1 was driven under a condition where the current density was constant, and changes in luminance relative to driving time were examined. FIG. 17 shows the normalized luminance versus time characteristics. FIG. 17 shows the favorable characteristics of the light-emitting element 1, and thus the element is found to have high reliability.

Example 3

In this example is described a light-emitting element in which 3,3'-bis(dibenzothiophen-4-yl)-N,N'-(1,3-phenylene)bicarbazole (abbreviation: mDBTCz2P-II, structural formula (100)), which is a carbazole compound described in Embodiment 1, was used for a host material of a light-emitting layer using an emission center substance that emits green phosphorescence.

The molecular structures of organic compounds used in this example are represented by structural formulae (iii) to (viii) and (100) below. In the element structure in FIG. 1A, an electron-injection layer is provided between an electron-transport layer 114 and a second electrode 104.

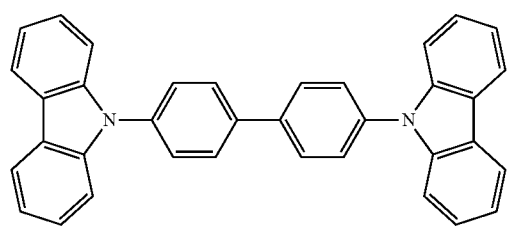

(iv) CBP

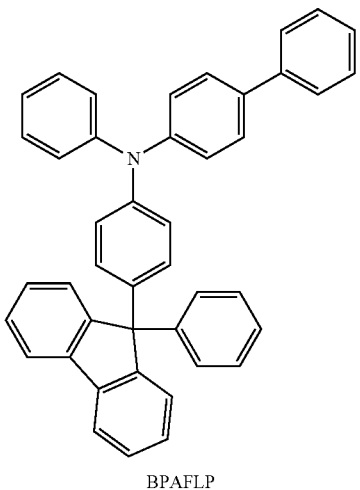

(v) BPAFLP

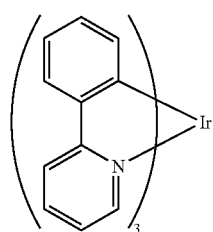

(vi) Ir(ppy)₃

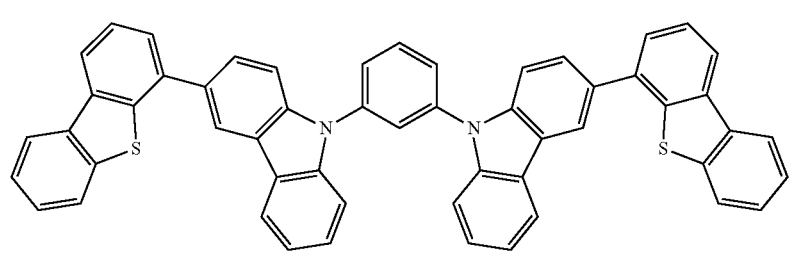

(100) mDBTCz2P-II

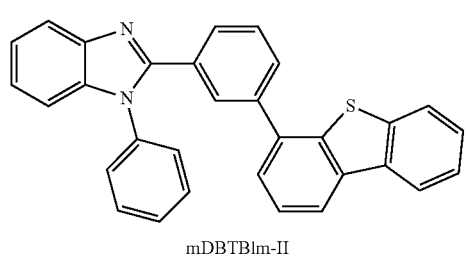

(vii) mDBTBIm-II

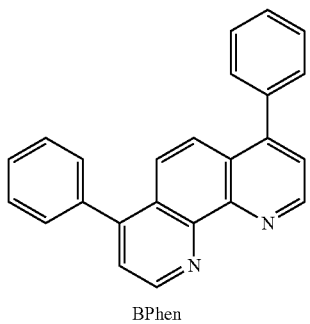

(iii) BPhen

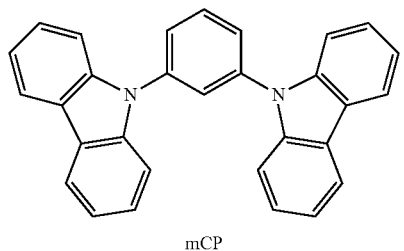

mCP (viii)

Fabrication of Light-Emitting Element 2 and Comparison Light-Emitting Element 2

First, the glass substrate 101, over which a film of iridium tin oxide containing silicon (ITSO) was formed to a thickness of 110 nm as the first electrode 102, was prepared. A surface of the ITSO film is covered with an insulating film, and a 2 mm square portion of the surface is exposed in order that a light-emitting area be set to 2 mm×2 mm. As pretreatment for forming the light-emitting elements over the substrate, the surface of the substrate was washed with water and baked at 200° C. for one hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed to a holder provided in the vacuum evaporation apparatus such that the surface of the substrate 101 over which the ITSO film was formed faced downward.

After the pressure in the vacuum evaporation apparatus was reduced to $10^{-4}$ Pa, 4,4'-bis(N-carbazolyl)biphenyl (abbreviation: CBP) represented by the above structural formula (iv) and molybdenum(VI) oxide were co-evaporated so that the weight ratio of CBP:molybdenum oxide was 2:1; thus, a hole-injection layer 111 was formed. The thickness thereof was set to 60 nm. Note that the co-evaporation is an evaporation method in which a plurality of different substances is concurrently vaporized from the respective different evaporation sources.

Next, 4-phenyl-4'-(9-phenylfluoren-9-yl)triphenylamine (abbreviation: BPAFLP) represented by the above structural formula (v) was evaporated a thickness of 20 nm, thereby fowling a hole-transport layer 112.

Further, over the hole-transport layer 112, 3,3'-bis(dibenzothiophen-4-yl)-N,N'-(1,3-phenylene)bicarbazole (abbreviation: mDBTCz2P-II), which is a carbazole compound described in Embodiment 1 and represented by the above structural formula (100), and tris(2-phenylpyridine)iridium (III) (abbreviation: Ir(ppy)₃) represented by the above structural formula (vi) were evaporated to a thickness of 30 nm so that the weight ratio of mDBTCz2P-II to Ir(ppy)₃ were 1:0.08. Thus, a light-emitting layer 113 was formed.

Next, 2-[3-(dibenzothiophen-4-yl)phenyl]-1-phenyl-1H-benzimidazole (abbreviation: mDBTBIm-II) represented by the above structural formula (vii) was evaporated to a thickness of 15 nm, and then bathophenanthroline (abbreviation: BPhen) represented by the above structural formula (iii) was evaporated to a thickness of 15 nm, thereby forming the electron-transport layer 114.

Further, lithium fluoride was evaporated to a thickness of 1 nm on over the electron-transport layer 114, thereby forming the electron-injection layer. Lastly, an aluminum film was formed to a thickness of 200 nm as the second electrode 104 functioning as a cathode. Thus, the light-emitting element 2 was completed. Note that in the above evaporation processes, evaporation was all performed by a resistance heating method.

In fabrication of the comparison light-emitting element 2, 1,3-bis(N-carbazolyl)benzene (abbreviation: mCP) represented by the above structural formula (viii) was replaced with mDBTCz2P-II in the light-emitting layer 113 of the light-emitting element 2.

Operation Characteristics of Light-Emitting Element 2 and Comparison Light-Emitting Element 2

The light-emitting element 2 and the comparison light-emitting element 2 thus obtained were sealed in a glove box under a nitrogen atmosphere without being exposed to the air. Then, the operation characteristics of these light-emitting elements were measured. Note that the measurements were carried out at room temperature (in an atmosphere kept at 25° C.).

Figure 18:
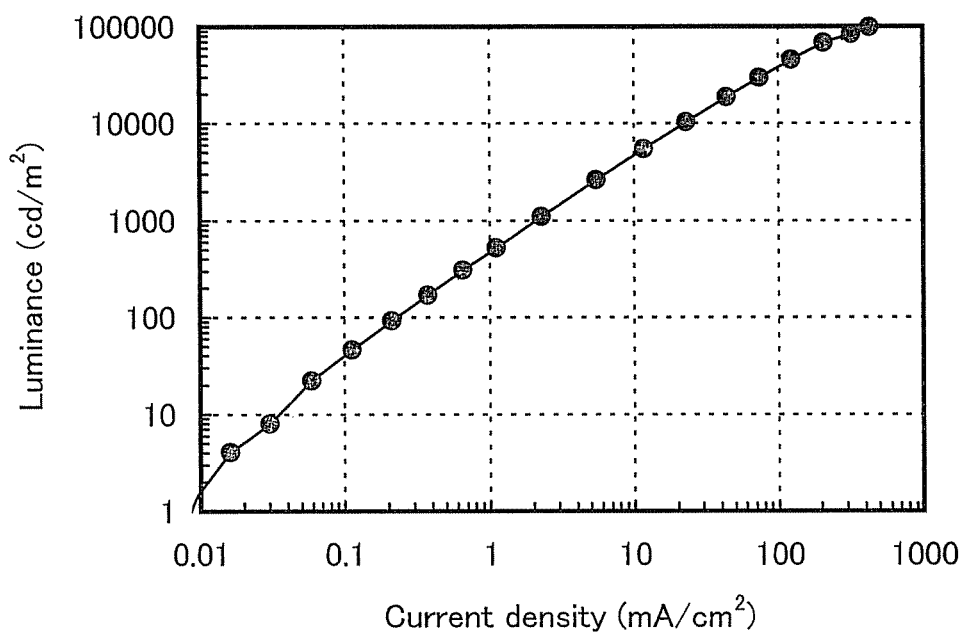
FIG. 18 shows luminance versus current density characteristics of a light-emitting element 2.
Figure 19:
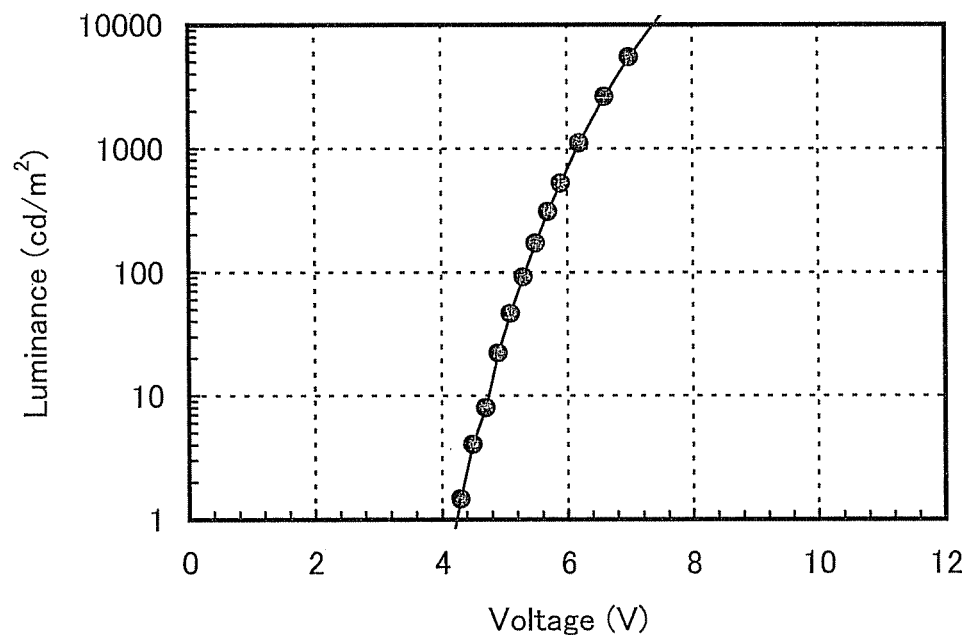
FIG. 19 shows luminance versus voltage characteristics of the light-emitting element 2.
Figure 20:
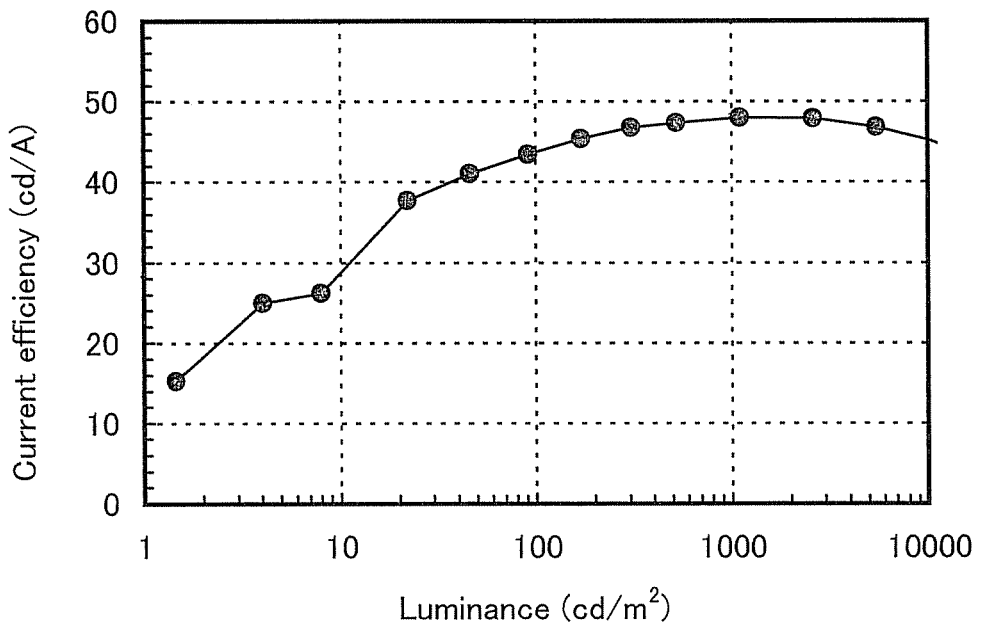
FIG. 20 shows current efficiency versus luminance characteristics of the light-emitting element 2.
Figure 21:
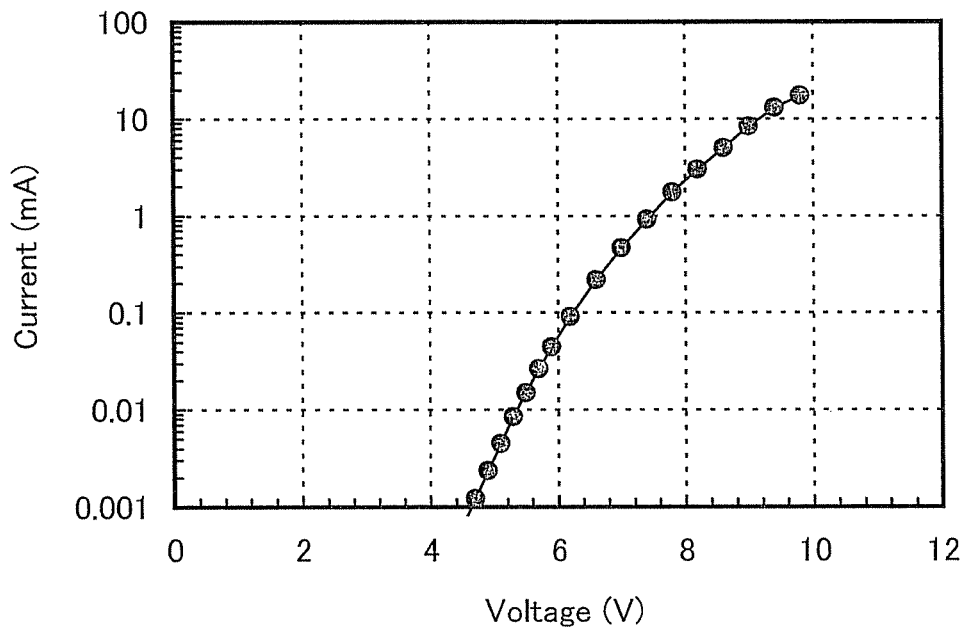
FIG. 21 shows current versus voltage characteristic of the light-emitting element 2.
Figure 22:
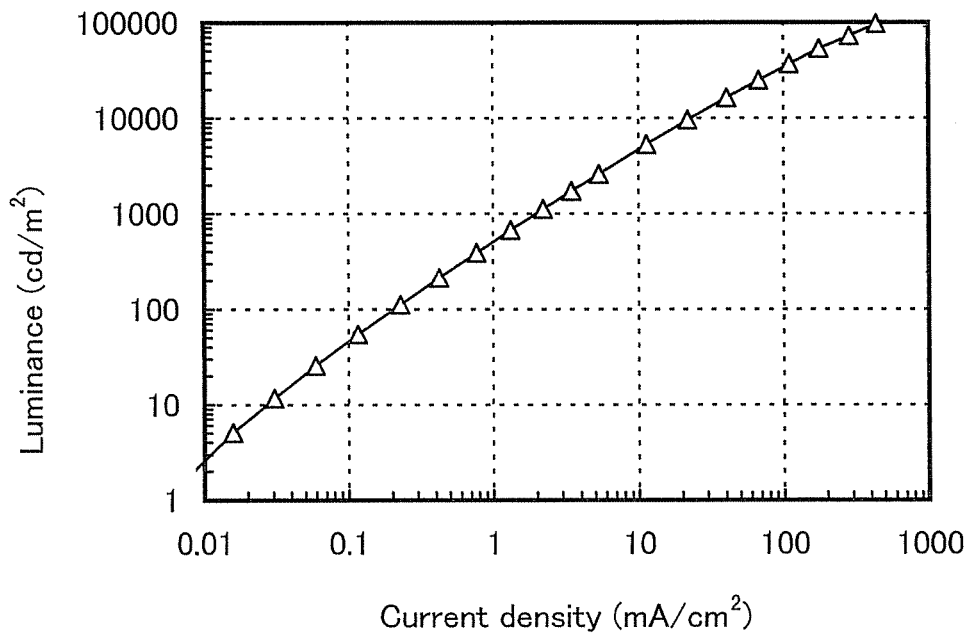
FIG. 22 shows luminance versus current density characteristics of a comparison light-emitting element 2.
Figure 23:
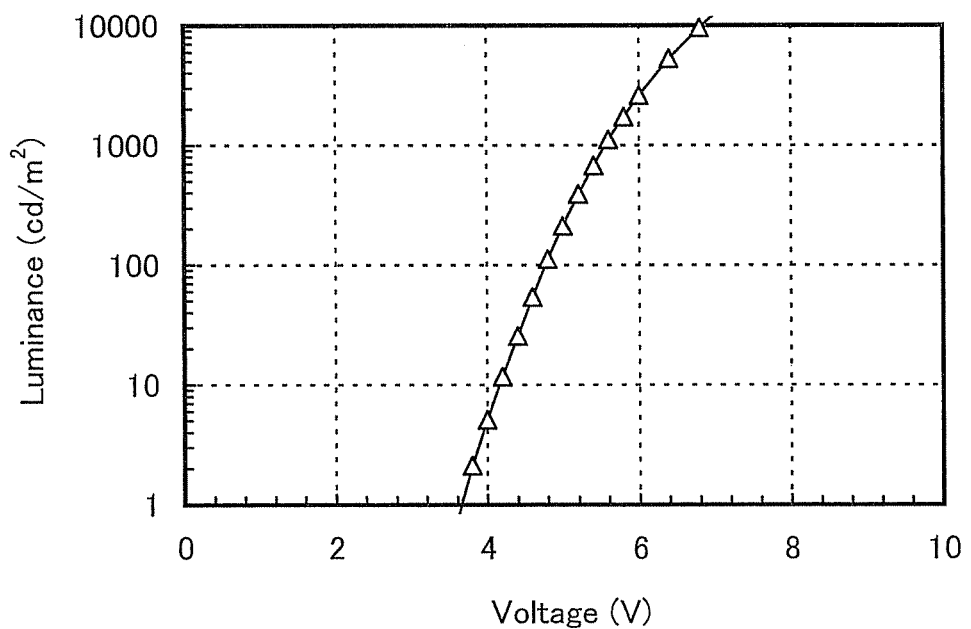
FIG. 23 shows luminance versus voltage characteristics of the comparison light-emitting element 2.
Figure 24:
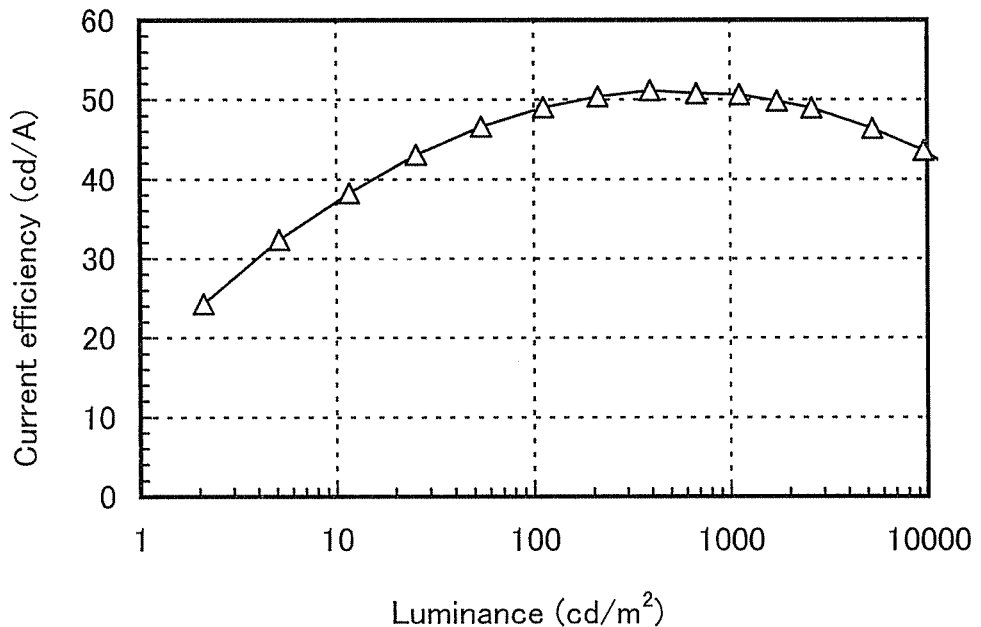
FIG. 24 shows current efficiency versus luminance characteristics of the comparison light-emitting element 2.
Figure 25:
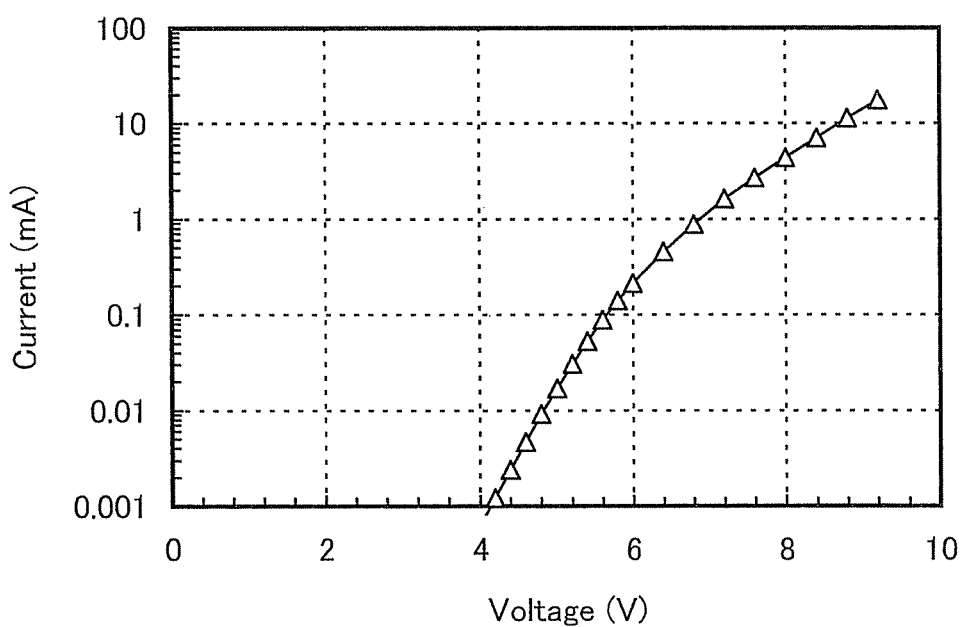
FIG. 25 shows current versus voltage characteristic of the comparison light-emitting element 2.

FIG. 18 shows luminance versus current density characteristics of the light-emitting element 2, FIG. 19 shows its luminance versus voltage characteristics, FIG. 20 shows its current efficiency versus luminance characteristics, and FIG. 21 shows its current versus voltage characteristics. FIG. 22 shows luminance versus current density characteristics of the comparison light-emitting element 2, FIG. 23 shows its luminance versus voltage characteristics, FIG. 24 shows its current efficiency versus luminance characteristics, and FIG. 25 shows its current versus voltage characteristics. In FIG. 18 and FIG. 22, the vertical axis represents luminance (cd/m²) and the horizontal axis represents current density (mA/cm²). In FIG. 19 and FIG. 23, the vertical axis represents luminance (cd/m²) and the horizontal axis represents voltage (V). In FIG. 20 and FIG. 24, the vertical axis represents current efficiency (cd/A) and the horizontal axis represents luminance (cd/m²). In FIG. 21 and FIG. 25, the vertical axis represents current (mA) and the horizontal axis represents voltage (V).

FIG. 20 and FIG. 24 indicate that the light-emitting element 2, in which the carbazole compound represented by the general formula (G1) was used for the host material of the light-emitting layer exhibiting green phosphorescence, exhibits as good current efficiency versus luminance characteristics as the characteristics of the comparison light-emitting element 2, in which mPC was used for the host material in the same way. Thus, the light-emitting element 2 is found to have high emission efficiency. This is because the carbazole compound represented by the general formula (G1) has as high triplet excitation energy and as a wide energy gap as those of mCP such that even a light-emitting substance that emits green phosphorescence can be effectively excited. In addition, FIG. 19 shows the favorable luminance versus voltage characteristics of the light-emitting element in which the carbazole compound represented by the general formula (G1) was used for the host material of the light-emitting layer exhibiting green phosphorescence. Thus, the element is found to have low driving voltage. This means that the carbazole compound represented by the general formula (G1) has an excellent carrier-transport property.

Figure 26:
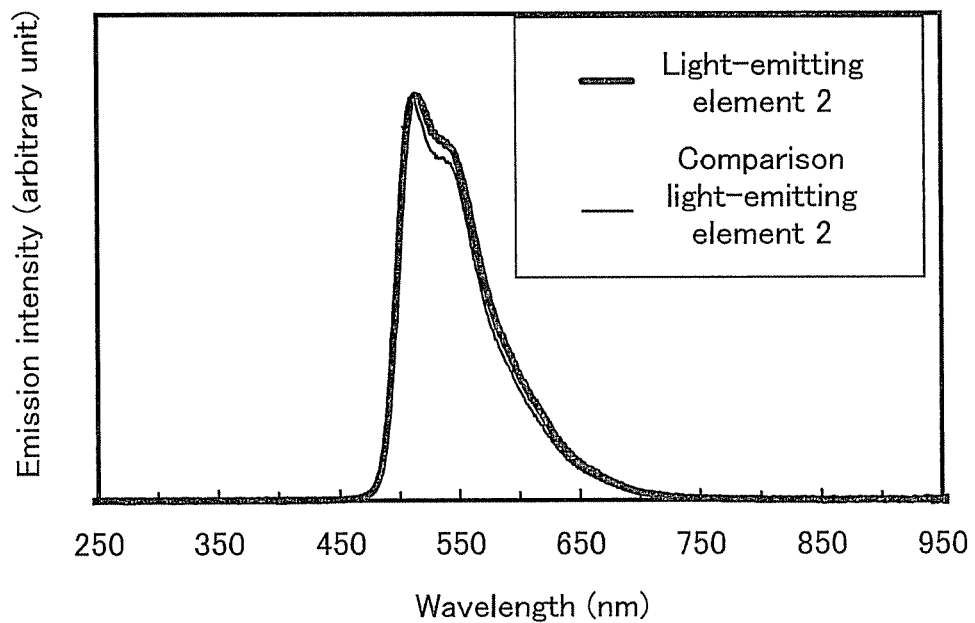
FIG. 26 shows emission spectra of the light-emitting element 2 and the comparison light-emitting element 2.

FIG. 26 shows emission spectra obtained when a current of 1 mA was made to flow in each of the light-emitting element 2 and the comparison light-emitting element 2. In FIG. 26, the vertical axis represents emission intensity (arbitrary unit) and the horizontal axis represents wavelength (nm). The emission intensity is shown as a value relative to the greatest emission intensity assumed to be 1. FIG. 26 indicates that the emission spectra of the light-emitting element 2 and the comparison light-emitting element 2 almost overlap and each element exhibit green light emission that originates from Ir(ppy)$_3$, which was the emission center substance.

Figure 27:
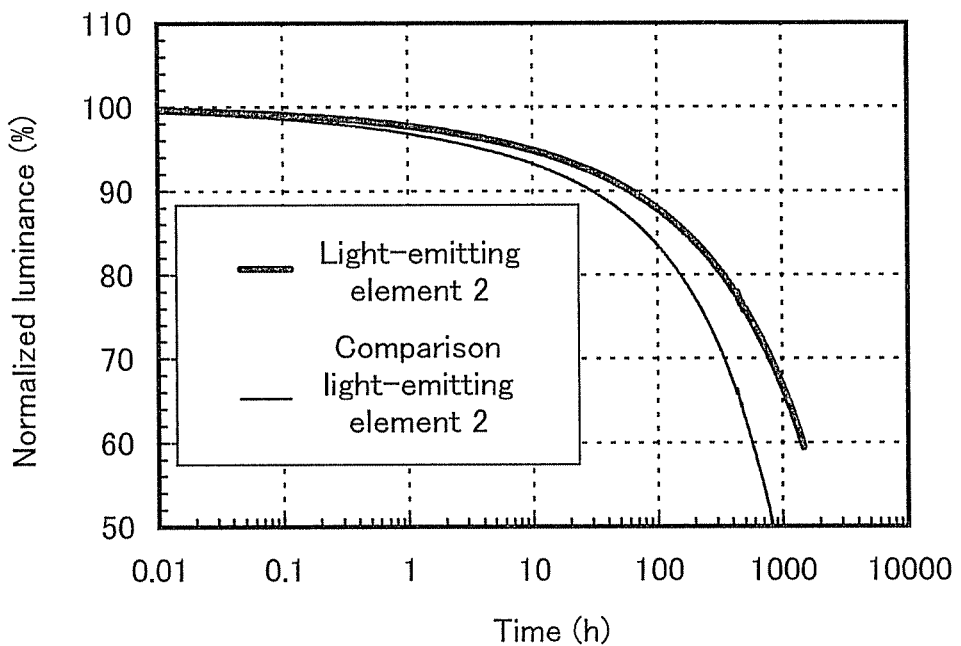
FIG. 27 shows normalized luminance versus time characteristics of the light-emitting element 2 and the comparison light-emitting element 2.

Next, with an initial luminance set to 1000 cd/m$^2$, these elements were driven under a condition where the current density was constant, and changes in luminance relative to driving time were examined. FIG. 27 shows that the decrease in the luminance of the light-emitting element 2 relative to driving time is small than that of the luminance of the comparison light-emitting element 2. Thus, the light-emitting element 2 is found to have high reliability. Since mCP has a large energy gap and high triplet excitation energy, the substance has been often used for a host material in an element to emit short-wavelength phosphorescence, thereby manufacturing a phosphorescent light-emitting element having favorable emission efficiency. However, a light-emitting element using mCP decreases in luminance greatly relative to driving time, that is, has a short lifetime, which has been problematic. Having as a large energy gap and as high triplet energy as those of an element using mCP, the light-emitting element 2 using a carbazole compound described in Embodiment 1 as the host material was able to achieve an improved lifetime while exhibiting as high emission efficiency as that of the element using mCP.

Example 4

In this example are described a light-emitting element (light-emitting element 3) in which 3,3'-bis(dibenzothiophen-4-yl)-N,N-(1,3-phenylene)bicarbazole (abbreviation: mDBTCz2P-II, structural formula (100)), which is a carbazole compound described in Embodiment 1, was used for a host material of a light-emitting layer using an emission center substance that emits blue green phosphorescence, and a light-emitting element (light-emitting element 4) in which mDBTCz2P-II was used for a material of a hole-transport layer adjacent to a light-emitting layer using an emission center substance that emits blue green phosphorescence.

The molecular structures of organic compounds used in this example are represented by structural formulae (iii), (iv), (vii) to (ix) and (100) below. In the element structure in FIG. 1A, an electron-injection layer is provided between an electron-transport layer 114 and a second electrode 104.

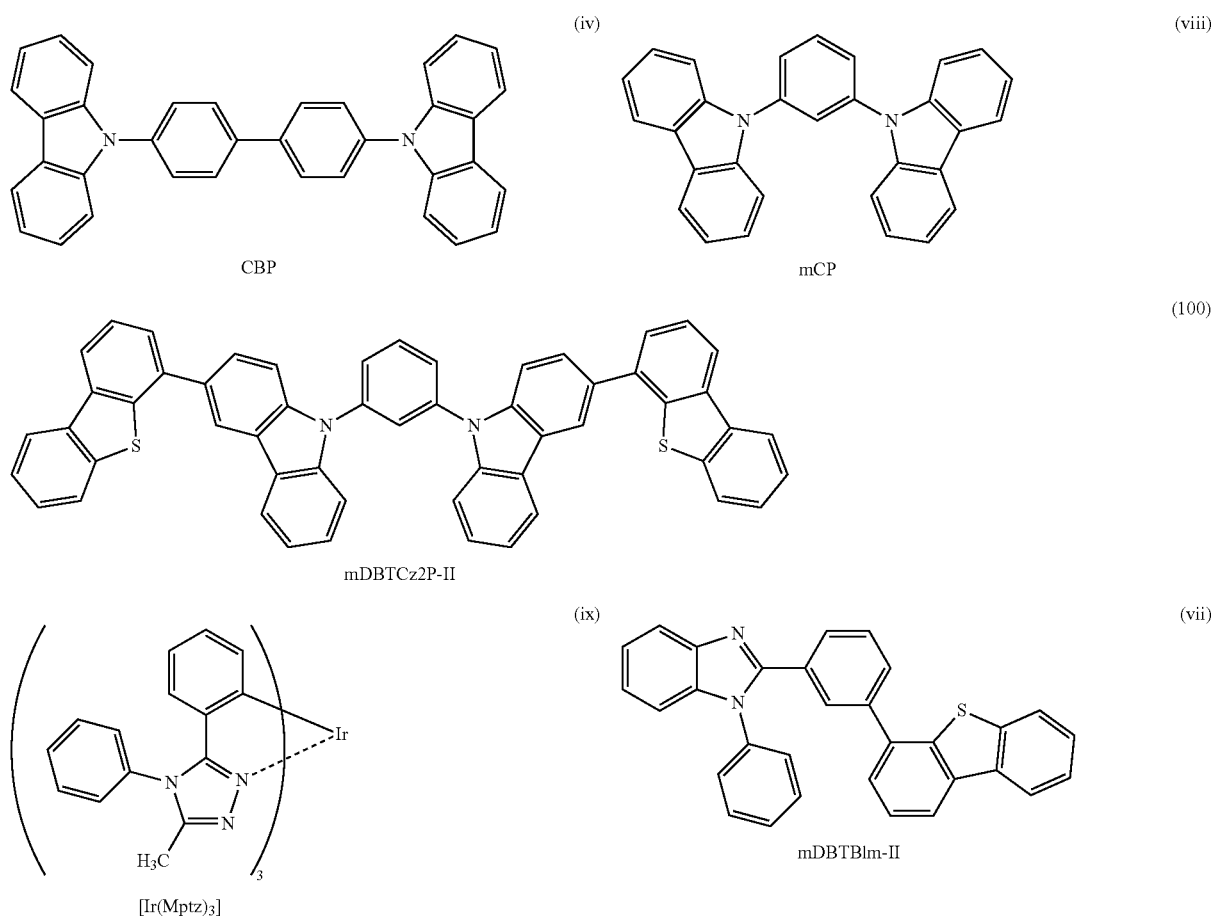

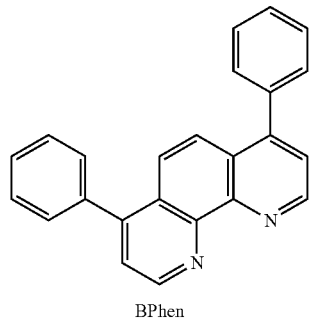

(iii)

BPhen

Fabrication of Light-Emitting Element 3 and Light-Emitting Element 4

First, the glass substrate 101, over which a film of indium tin oxide containing silicon (ITSO) was formed to a thickness of 110 nm as the first electrode 102, was prepared. A surface of the ITSO film is covered with an insulating film, and a 2 mm square portion of the surface is exposed in order that a light-emitting area be set to 2 mm×2 mm. As pretreatment for forming the light-emitting elements over the substrate, the surface of the substrate was washed with water and baked at 200° C. for one hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed to a holder provided in the vacuum evaporation apparatus such that the surface of the substrate 101 over which the ITSO film was formed faced downward.

After the pressure in the vacuum evaporation apparatus was reduced to $10^{-4}$ Pa, or represented by the above structural formula (Iv) 4,4'-bis(N-carbazolyl)biphenyl (abbreviation: CBP) and molybdenum(VI) oxide were co-evaporated so that the weight ratio of CBP:molybdenum oxide was 2:1; thus, the hole-injection layer 111 was formed. The thickness thereof was set to 60 nm. Note that the co-evaporation is an evaporation method in which a plurality of different substances is concurrently vaporized from the respective different evaporation sources.

Next, for the light-emitting element 3, 1,3-bis(N-carbazolyl)benzene (abbreviation: mCP) represented by the above structural formula (viii) was evaporated a thickness of 20 nm, thereby forming a hole-transport layer 112. For the light-emitting element 4, 3,3'-bis(dibenzothiophen-4-yl)-N,N'-(1,3-phenylene)bicarbazole (abbreviation: mDBTCz2P-II), which is a carbazole compound described in Embodiment 1 and represented by the above structural formula (100), was evaporated a thickness of 20 nm, thereby forming the hole-transport layer 112.

Further, for the light-emitting element 3, a light-emitting layer 113 was formed over the hole-transport layer 112 by forming a stacked layer in such a way that mDBTCz2P-II and tris(5-methyl-3,4-diphenyl-4H-1,2,4-triazolato)iridium(III) (abbreviation: [Ir(Mptz)$_3$]) represented by the above structural formula (ix) were evaporated to a thickness of 30 nm so that the weight ratio of mDBTCz2P-II to [Ir(Mptz)$_3$] was 1:0.08, and thereover, 2-[3-(dibenzothiophen-4-yl)phenyl]-1-phenyl-1H-benzimidazole (abbreviation: mDBTBIm-II) represented by the above structural formula (vii) and [Ir(Mptz)$_3$] were evaporated to a thickness of 10 nm so that the weight ratio of mDBTBIm-II to [Ir(Mptz)$_3$] was 1:0.08.

For the light-emitting element 4, a light-emitting layer 113 was formed by forming a stacked layer in such a way that mCP and tris(5-methyl-3,4-diphenyl-4H-1,2,4-triazolato)iridium(III) (abbreviation: [Ir(Mptz)$_3$]) represented by the above structural formula (ix) were evaporated to a thickness of 30 nm so that the weight ratio of mCP to [Ir(Mptz)$_3$] was 1:0.08, and thereover, 2-[3-(dibenzothiophen-4-yl)phenyl]-1-phenyl-1H-benzimidazole (abbreviation: mDBTBIm-II) represented by the above structural formula (vii) and [Ir(Mptz)$_3$] were evaporated to a thickness of 10 nm so that the weight ratio of mDBTBIm-II to [Ir(Mptz)$_3$] was 1:0.08.

Next, bathophenanthroline (abbreviation: BPhen) represented by the above structural formula (iii) was evaporated to a thickness of 15 nm, thereby forming the electron-transport layer 114.

Further, lithium fluoride was evaporated to a thickness of 1 nm on over the electron-transport layer 114, thereby forming the electron-injection layer. Lastly, an aluminum film was formed to a thickness of 200 nm as the second electrode 104 functioning as a cathode. Thus, the light-emitting elements 3 and 4 were completed. Note that in the above evaporation processes, evaporation was all performed by a resistance heating method.

Operation Characteristics of Light-Emitting Element 3 and Light-Emitting Element 4

The light-emitting elements 3 and 4 thus obtained were sealed in a glove box under a nitrogen atmosphere without being exposed to the air. Then, the operation characteristics of these light-emitting elements were measured. Note that the measurements were carried out at room temperature (in an atmosphere kept at 25° C.).

Figure 28:
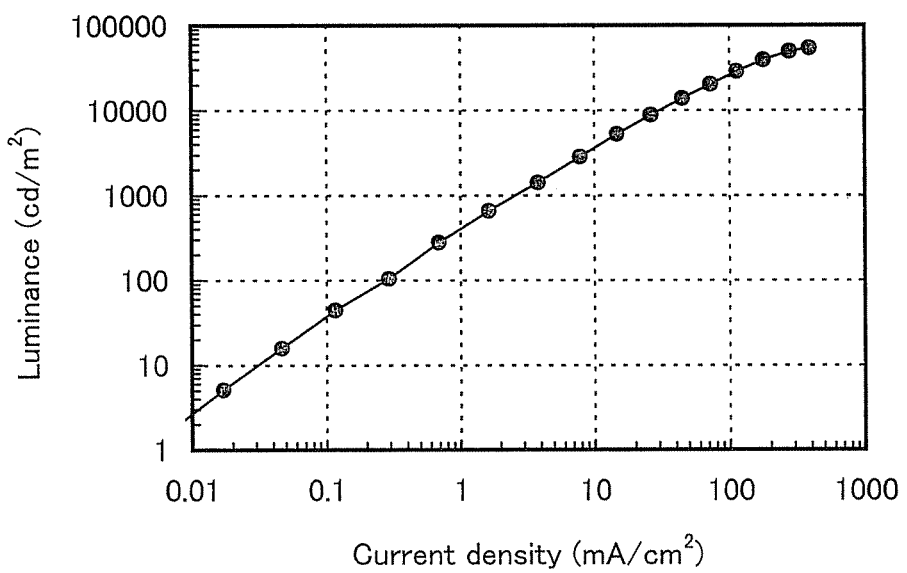
FIG. 28 shows luminance versus current density characteristics of a light-emitting element 3.
Figure 29:
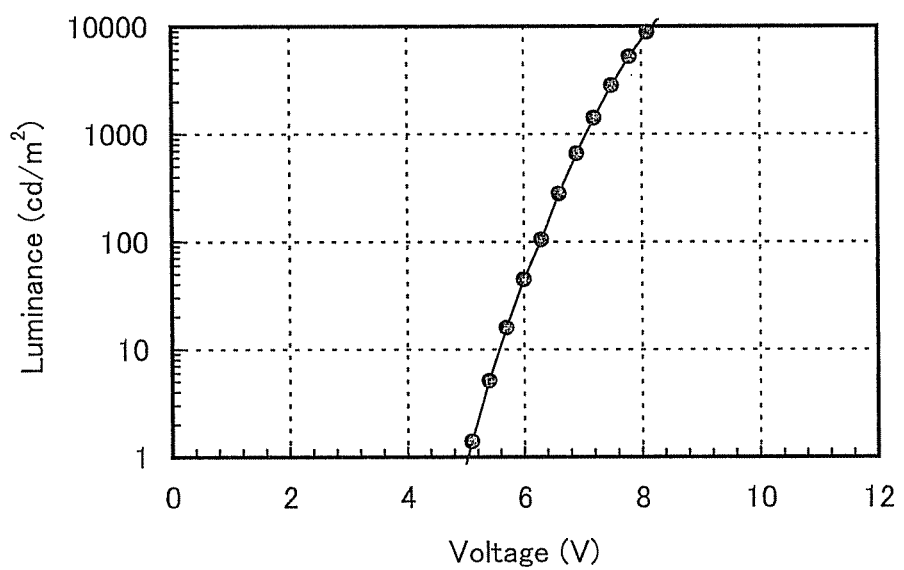
FIG. 29 shows luminance versus voltage characteristics of the light-emitting element 3.
Figure 30:
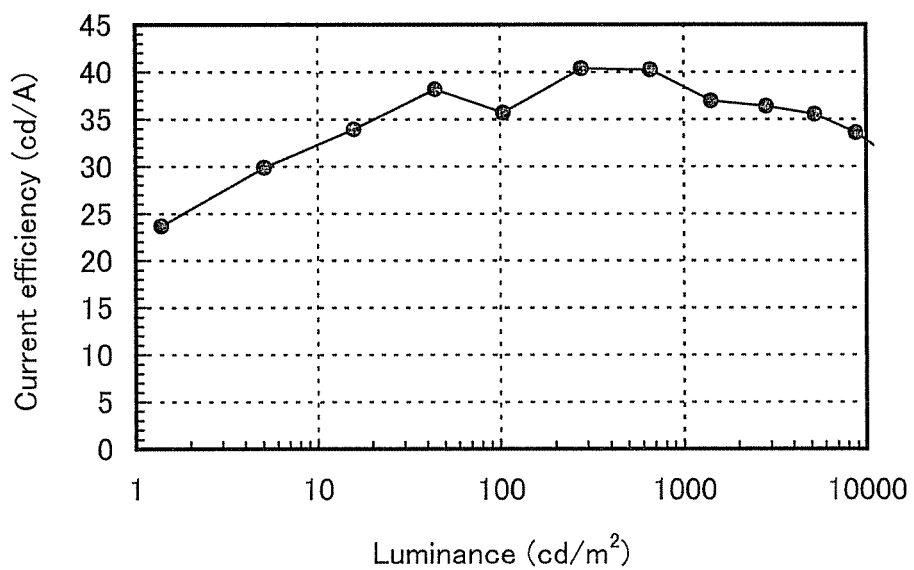
FIG. 30 shows current efficiency versus luminance characteristics of the light-emitting element 3.
Figure 31:
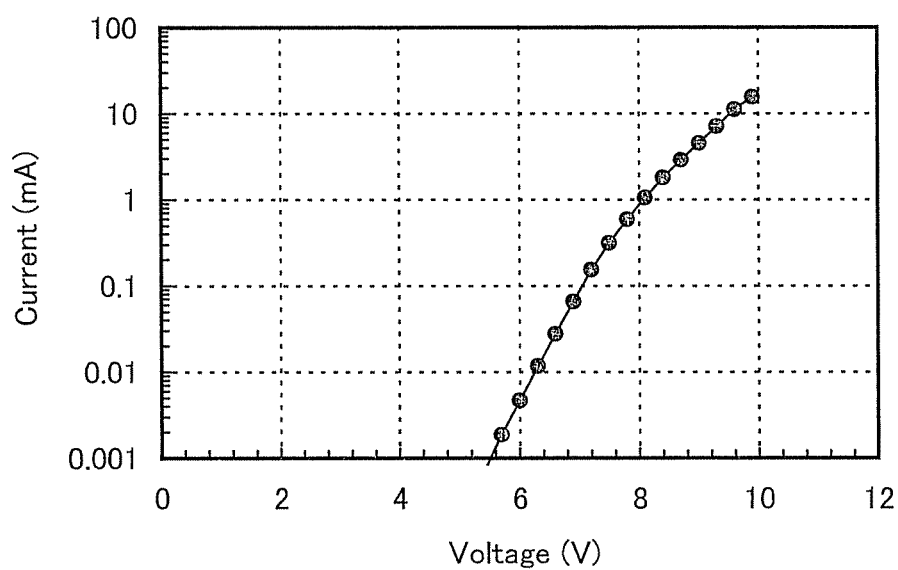
FIG. 31 shows current versus voltage characteristic of the light-emitting element 3.
Figure 32:
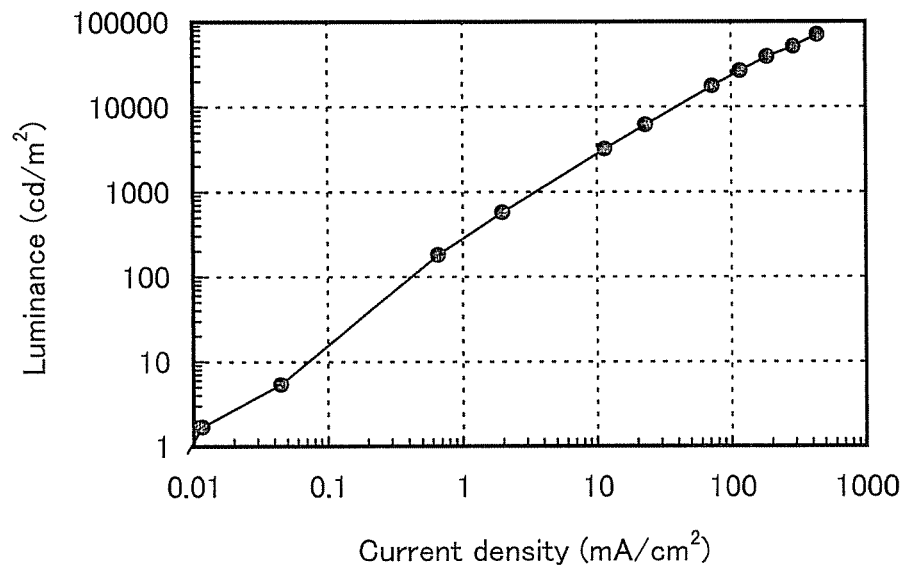
FIG. 32 shows luminance versus current density characteristics of a light-emitting element 4.
Figure 33:
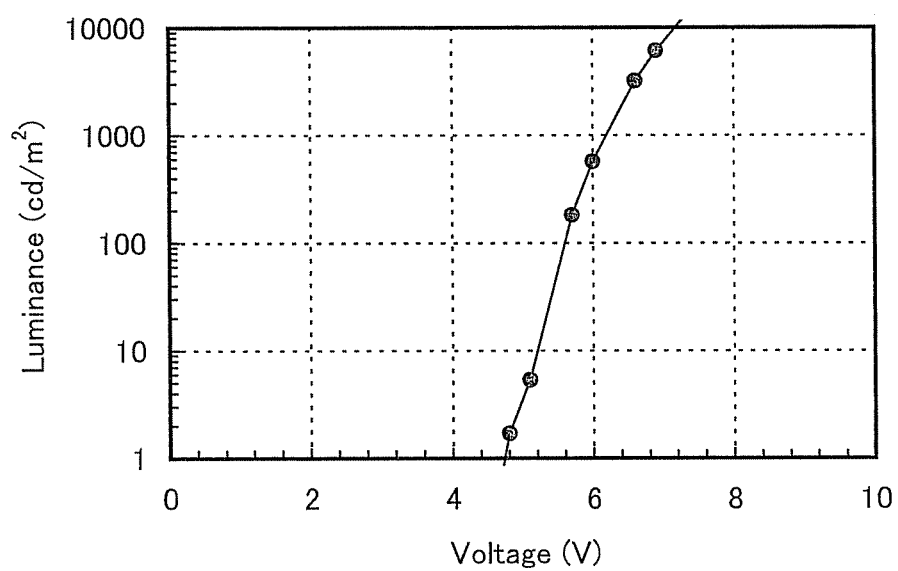
FIG. 33 shows luminance versus voltage characteristics of the light-emitting element 4.
Figure 34:
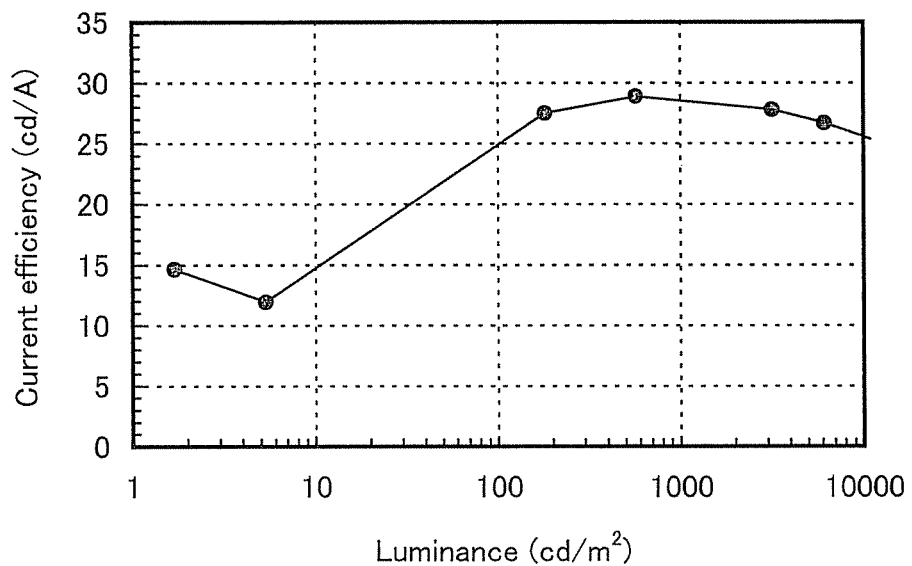
FIG. 34 shows current efficiency versus luminance characteristics of the light-emitting element 4.
Figure 35:
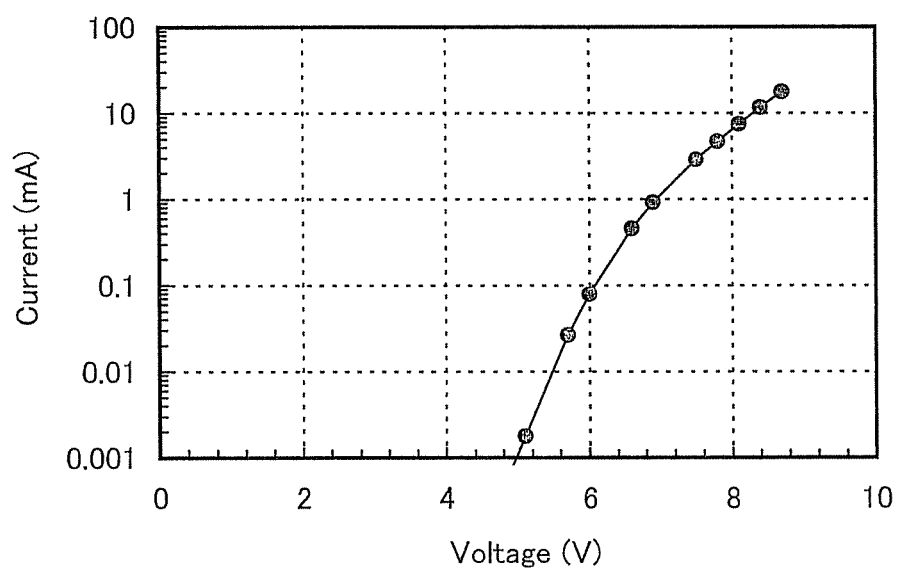
FIG. 35 shows current versus voltage characteristic of the light-emitting element 4.

FIG. 28 shows luminance versus current density characteristics of the light-emitting element 3, FIG. 29 shows its luminance versus voltage characteristics, FIG. 30 shows its current efficiency versus luminance characteristics, and FIG. 31 shows its current versus voltage characteristics. FIG. 32 shows luminance versus current density characteristics of the light-emitting element 4, FIG. 33 shows its luminance versus voltage characteristics, FIG. 34 shows its current efficiency versus luminance characteristics, and FIG. 35 shows its current versus voltage characteristics. In FIG. 28 and FIG. 32, the vertical axis represents luminance (cd/m$^2$) and the horizontal axis represents current density (mA/cm$^2$). In FIG. 29 and FIG. 33, the vertical axis represents luminance (cd/m$^2$) and the horizontal axis represents voltage (V). In FIG. 30 and FIG. 34, the vertical axis represents current efficiency (cd/A) and the horizontal axis represents luminance (cd/m$^2$). In FIG. 31 and FIG. 35, the vertical axis represents current (mA) and the horizontal axis represents voltage (V).

FIG. 30 shows the favorable current efficiency versus luminance characteristics of the light-emitting element 3, in which the carbazole compound represented by the general formula (G1) was used for the host material of the light-emitting layer exhibiting blue green phosphorescence. Thus, the element is found to have high emission efficiency. This is because the carbazole compound represented by the general formula (G1) has high triplet excitation energy and a wide energy gap such that even a light-emitting substance that emits blue green phosphorescence can be effectively excited. In addition, FIG. 29 shows the favorable luminance versus voltage characteristics of the light-emitting element, in which the carbazole compound represented by the general formula (G1) was used for the host material of the light-emitting layer exhibiting blue green phosphorescence. Thus, the element is found to have low driving voltage. This means that the carbazole compound represented by the general formula (G1) has an excellent carrier-transport property.

FIG. 34 shows the favorable current efficiency versus luminance characteristics of the light-emitting element 4, in which the carbazole compound represented by the general formula (G1) was used for the hole-transport material adjacent to the light-emitting layer exhibiting blue green phosphorescence. Thus, the element is found to have high emission efficiency. This is because since mDBTCz2P-II, which is a carbazole compound described in Embodiment 1, has a wide energy gap and a high triplet excitation energy accordingly, even when it is used for the hole-transport layer adjacent to the emission center substance that emits blue green phosphorescence, a reduction in emission efficiency is suppressed without transfer of excitation energy to the hole-transport layer. In addition, FIG. 33 shows the favorable luminance versus voltage characteristics of the light-emitting element in which the carbazole compound represented by the general formula (G1) was used for the host material of the light-emitting layer exhibiting blue green phosphorescence. Thus, the element is found to have low driving voltage. This means that the carbazole compound represented by the general formula (G1) has an excellent carrier-transport property.

Figure 36:
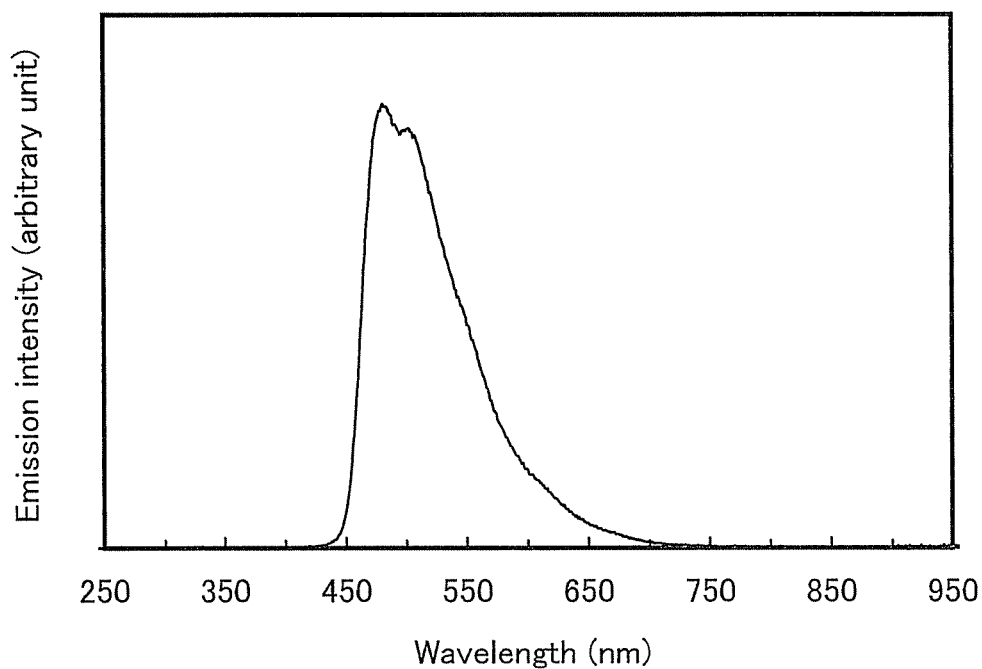
FIG. 36 shows an emission spectrum of the light-emitting element 3.
Figure 37:
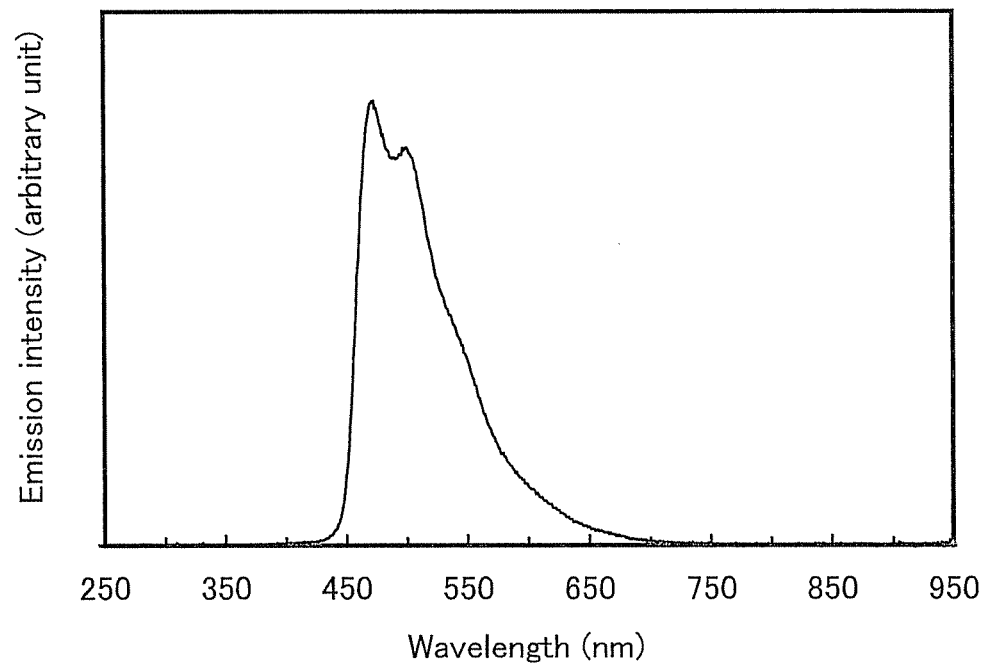
FIG. 37 shows an emission spectrum of the light-emitting element 4.

FIG. 36 shows an emission spectrum when a current of 0.1 mA was made to flow in the fabricated light-emitting element 3, and FIG. 37 shows an emission spectrum when a current of 0.1 mA was made to flow in the light-emitting element 4. In FIG. 36 and FIG. 37, the vertical axis represents emission intensity (arbitrary unit) and the horizontal axis represents wavelength (nm). The emission intensity is shown as a value relative to the greatest emission intensity assumed to be 1. FIG. 36 and FIG. 37 indicate that each of the light-emitting elements 3 and 4 emit blue green light that originates from [Ir(Mptz)$_3$], which was the emission center substance.

Figure 38:
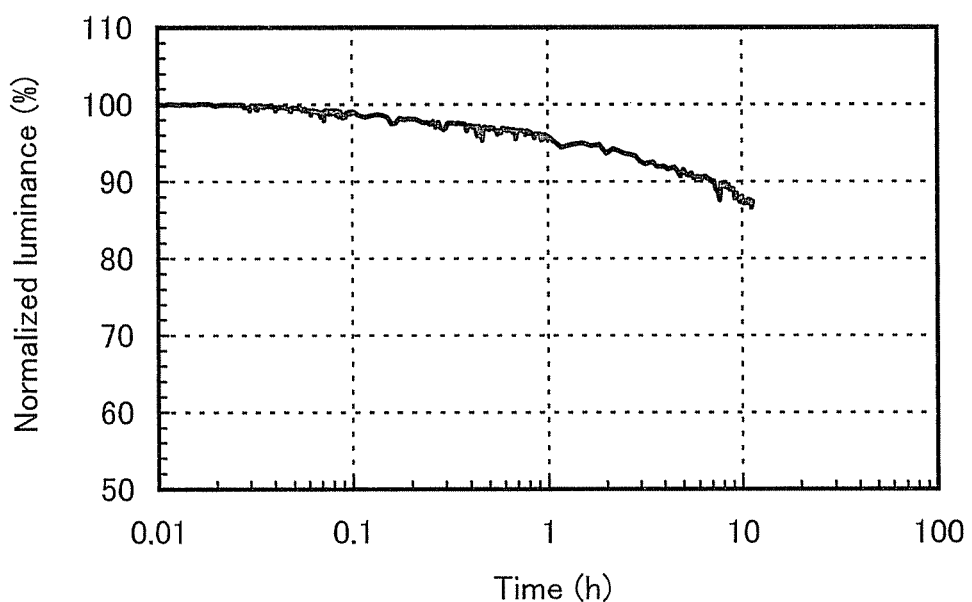
FIG. 38 shows normalized luminance versus time characteristics of the light-emitting element 3.
Figure 39:
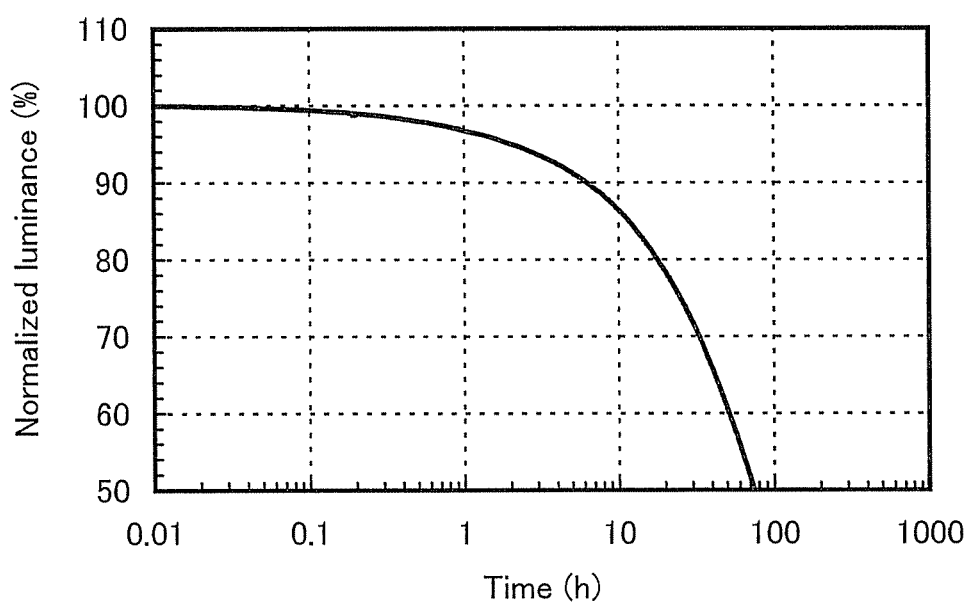
FIG. 39 shows normalized luminance versus time characteristics of the light-emitting element 4.

Next, with an initial luminance set to 1000 cd/m$^2$, these elements were driven under a condition where the current density was constant, and changes in luminance relative to driving time were examined. FIG. 38 shows normalized luminance versus time characteristics of the light-emitting element 3, and FIG. 39 shows those of the light-emitting element 4. As can be seen from FIG. 38 and FIG. 39, the decrease in the luminance of each of the light-emitting elements 3 and 4 relative to driving time is small. Thus, each element is found to have high reliability.

Thus, a light-emitting element, in which an emission center substance emits blue green phosphorescence and a carbazole compound described in Embodiment 1 is used for a host material or for a hole-transport material, can have high emission efficiency by efficient excitation for blue green phosphorescence which is the light emission from the high triplet excitation energy or by prevention of a loss due to energy transfer. This demonstrates the high triplet excitation energy of the carbazole compound described in Embodiment 1.

Example 5

In this example is described a light-emitting element (light-emitting element 5) in which 3,3'-bis(dibenzothiophen-4-yl)-N,N'-(1,3-phenylene)bicarbazole (abbreviation: mDBTCz2P-II, structural formula (100)), which is a carbazole compound described in Embodiment 1, was used for a host material of a light-emitting layer using an emission center substance that emits blue phosphorescence, and a light-emitting element (light-emitting element 6) in which mDBTCz2P-II was used for a material of a hole-transport layer adjacent to a light-emitting layer using an emission center substance that emits blue phosphorescence.

The molecular structures of organic compounds used in this example are represented by structural formulae (iii), (iv), (vii), (viii), (x), and (100) below. In the element structure in FIG. 1A, an electron-injection layer is provided between an electron-transport layer 114 and a second electrode 104.

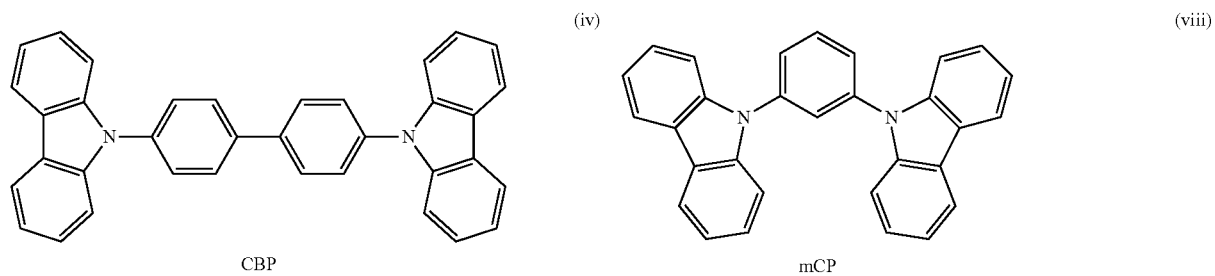

(iv)  CBP (viii)  mCP

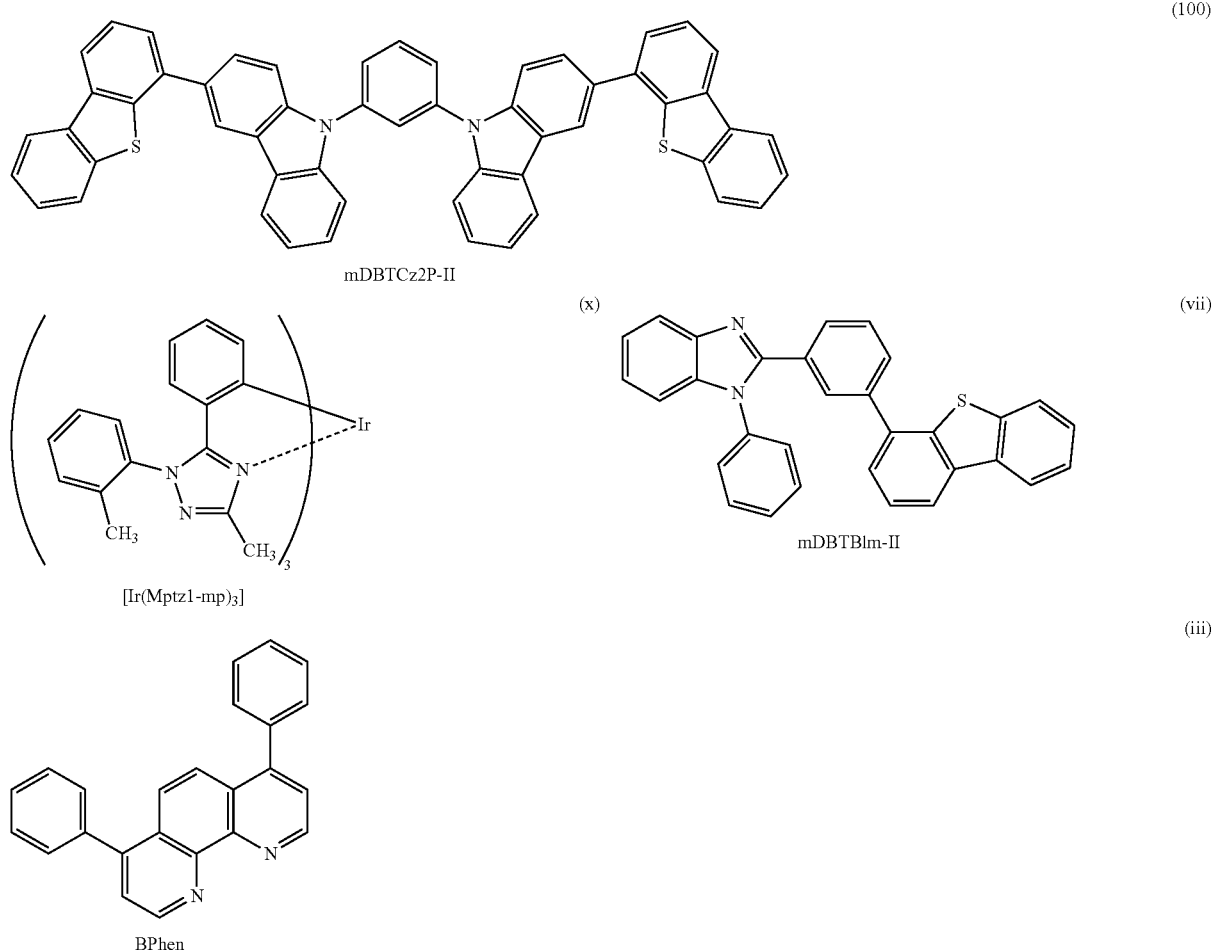

Fabrication of Light-Emitting Element 5 and Light-Emitting Element 6

First, the glass substrate 101, over which a film of indium tin oxide containing silicon (ITSO) was formed to a thickness of 110 nm as the first electrode 102, was prepared. A surface of the ITSO film is covered with an insulating film, and a 2 mm square portion of the surface is exposed in order that a light-emitting area be set to 2 mm×2 mm. As pretreatment for forming the light-emitting elements over the substrate, the surface of the substrate was washed with water and baked at 200° C. for one hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed to a holder provided in the vacuum evaporation apparatus such that the surface of the substrate 101 over which the ITSO film was formed faced downward.

After the pressure in the vacuum evaporation apparatus was reduced to $10^{-4}$ Pa, or represented by the above structural formula (iv) 4,4'-bis(N-carbazolyl)biphenyl (abbreviation: CBP) and molybdenum(VI) oxide were co-evaporated so that the weight ratio of CBP:molybdenum oxide was 2:1; thus, the hole-injection layer 111 was formed. The thickness thereof was set to 60 nm. Note that the co-evaporation is an evaporation method in which a plurality of different substances is concurrently vaporized from the respective different evaporation sources.

Next, for the light-emitting element 5, 1,3-bis(N-carbazolyl)benzene (abbreviation: mCP) represented by the above structural formula (viii) was evaporated a thickness of 20 nm, thereby forming the hole-transport layer 112. For the light-emitting element 6, 3,3'-bis(dibenzothiophen-4-yl)-N,N-(1,3-phenylene)bicarbazole (abbreviation: mDBTCz2P-II), which is a carbazole compound described in Embodiment 1 and represented by the above structural formula (100), was evaporated a thickness of 20 nm, thereby forming the hole-transport layer 112.

Further, for the light-emitting element 5, a light-emitting layer 113 was formed over the hole-transport layer 112 by forming a stacked layer in such a way that tris[3-methyl-1-(2-methylphenyl)-5-phenyl-1H-1,2,4-triazolato]iridium(III) (abbreviation: [Ir(Mptzl-mp)$_3$]) represented by the above structural formula (x) were evaporated to a thickness of 30 nm so that the weight ratio of mDBTCz2P-II to [Ir(Mptzl-mp)$_3$] was 1:0.08, and thereover, 2-[3-(dibenzothiophen-4-yl)phenyl]-1-phenyl-1H-benzimidazole (abbreviation: mDBTBIm-II) represented by the above structural formula (vii) and [Ir(Mptzl-mp)$_3$] were evaporated to a thickness of 10 nm so that the weight ratio of mDBTBIm-II to [Ir(Mptzl-mp)$_3$] was 1:0.08.

For the light-emitting element 6, a light-emitting layer 113 was formed by forming a stacked layer in such a way that mCP and [Ir(Mptzl-mp)$_3$] were evaporated to a thickness of 30 nm so that the weight ratio of mCP to [Ir(Mptzl-mp)$_3$] was 1:0.08, and thereover, mDBTBIm-II and [Ir(Mptzl-mp)$_3$] were evaporated to a thickness of 10 nm so that the weight ratio of mDBTBIm-II to [Ir(Mptzl-mp)$_3$] was 1:0.08.

Next, bathophenanthroline (abbreviation: BPhen) represented by the above structural formula (iii) was evaporated to a thickness of 15 nm, thereby forming the electron-transport layer 114.

Further, lithium fluoride was evaporated to a thickness of 1 nm on over the electron-transport layer 114, thereby forming the electron-injection layer. Lastly, an aluminum film was formed to a thickness of 200 nm as the second electrode 104 functioning as a cathode. Thus, the light-emitting elements 5 and 6 were completed. Note that in the above evaporation processes, evaporation was all performed by a resistance heating method.

Operation Characteristics of Light-Emitting Element 5 and Light-Emitting Element 6

The light-emitting elements 5 and 6 thus obtained were sealed in a glove box under a nitrogen atmosphere without being exposed to the air. Then, the operation characteristics of these light-emitting elements were measured. Note that the measurements were carried out at room temperature (in an atmosphere kept at 25° C.).

Figure 40:
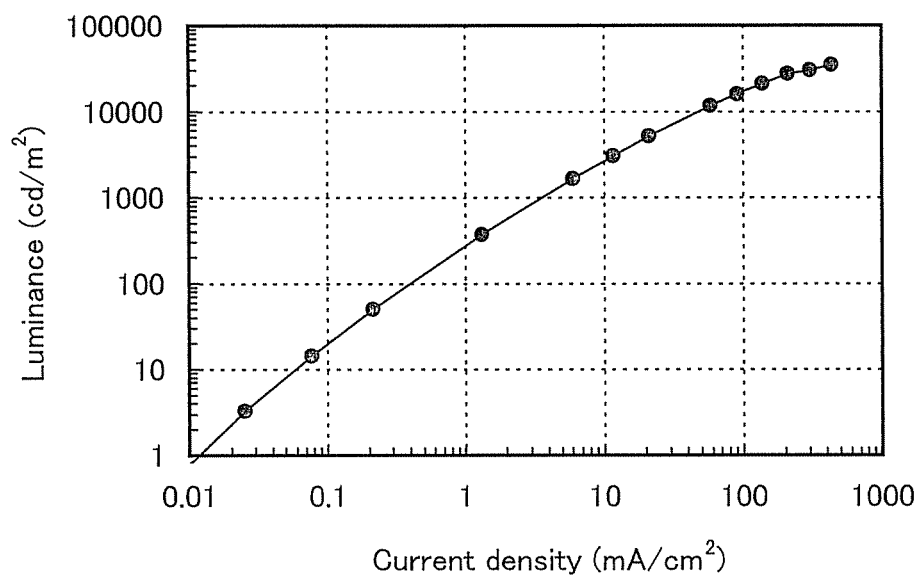
FIG. 40 shows luminance versus current density characteristics of a light-emitting element 5.
Figure 41:
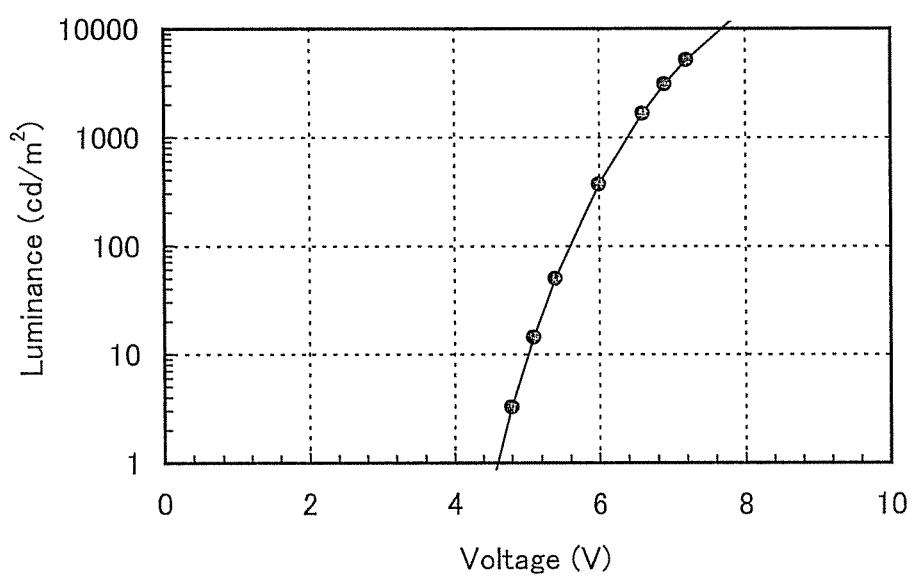
FIG. 41 shows luminance versus voltage characteristics of the light-emitting element 5.
Figure 42:
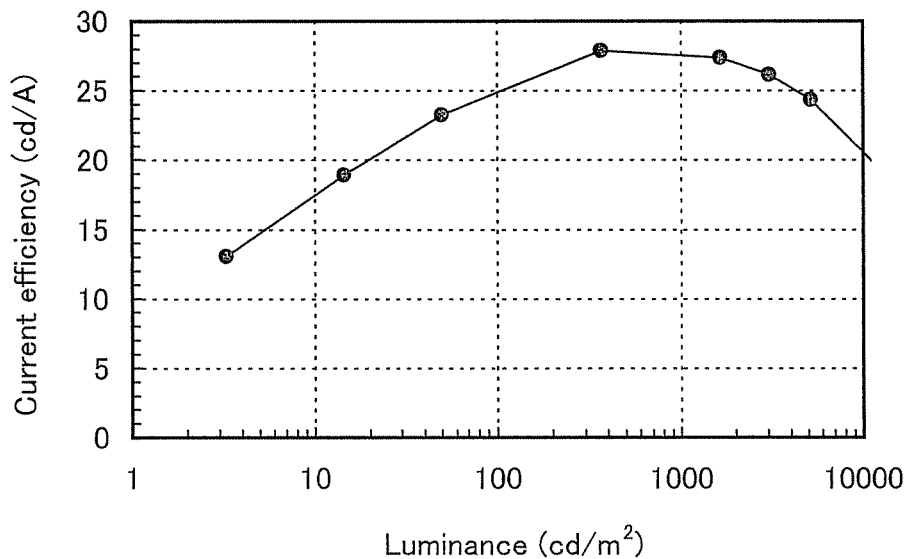
FIG. 42 shows current efficiency versus luminance characteristics of the light-emitting element 5.
Figure 43:
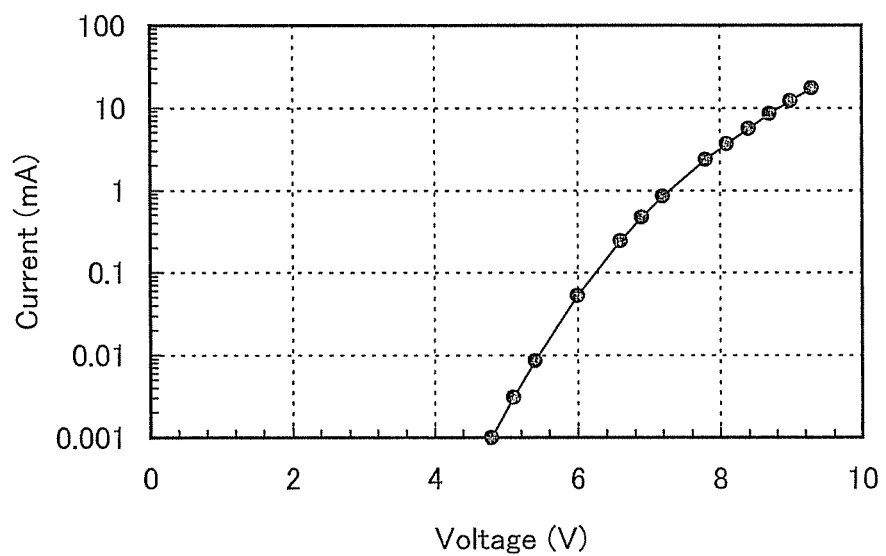
FIG. 43 shows current versus voltage characteristic of the light-emitting element 5.
Figure 44:
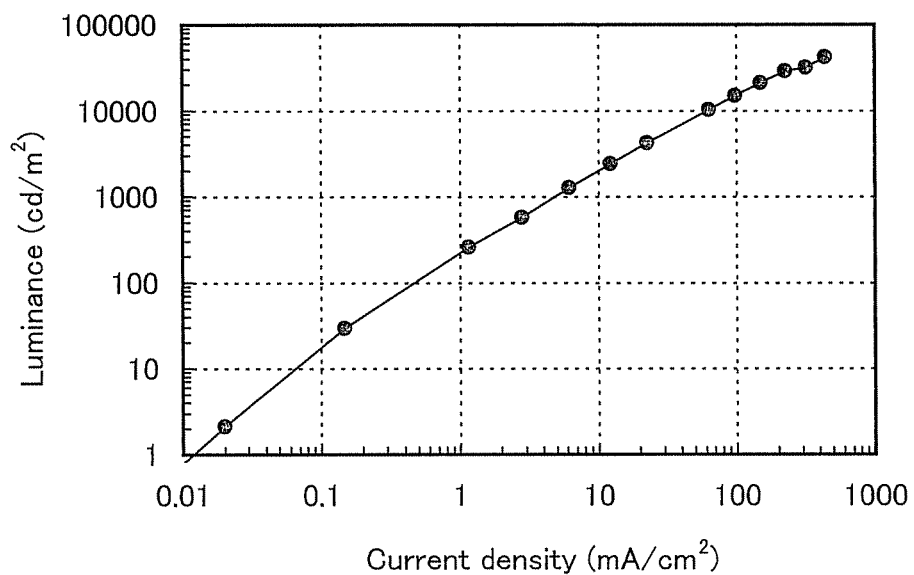
FIG. 44 shows luminance versus current density characteristics of a light-emitting element 6.
Figure 45:
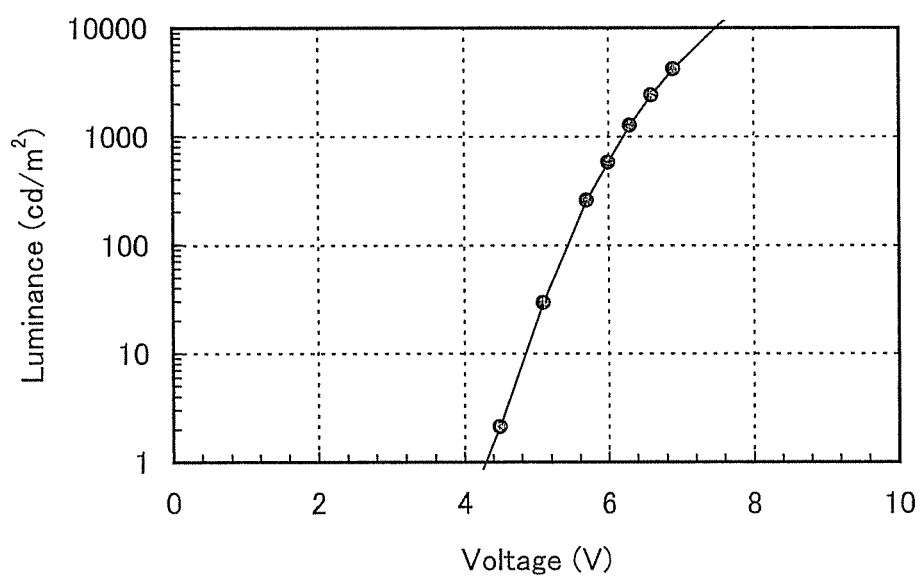
FIG. 45 shows luminance versus voltage characteristics of the light-emitting element 6.
Figure 46:
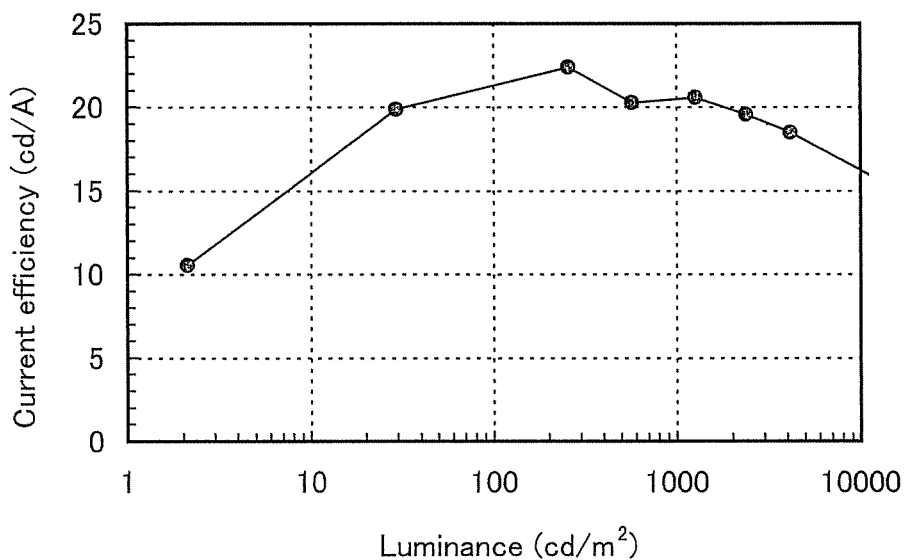
FIG. 46 shows current efficiency versus luminance characteristics of the light-emitting element 6.
Figure 47:
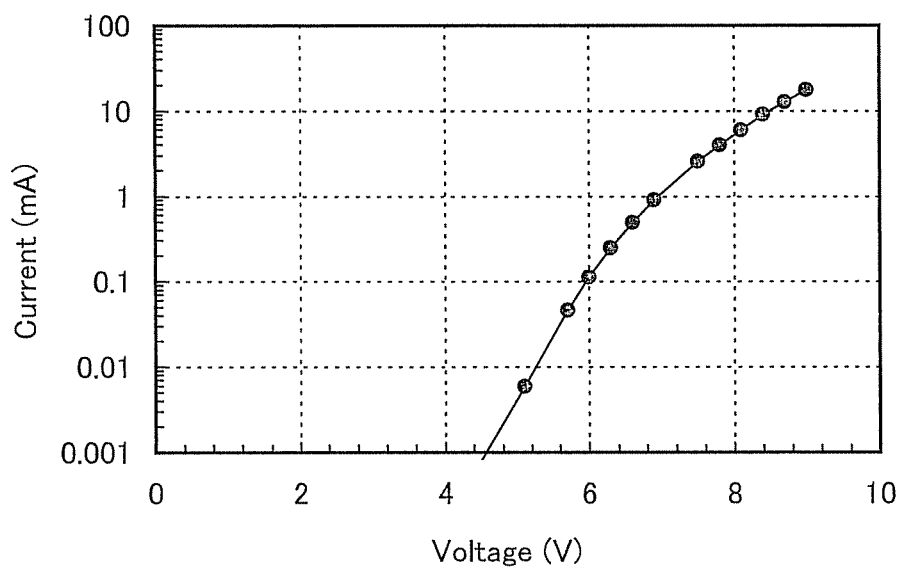
FIG. 47 shows current versus voltage characteristic of the light-emitting element 6.

FIG. 40 shows luminance versus current density characteristics of the light-emitting element 5, FIG. 41 shows its luminance versus voltage characteristics, FIG. 42 shows its current efficiency versus luminance characteristics, and FIG. 43 shows its current versus voltage characteristics. FIG. 44 shows luminance versus current density characteristics of the light-emitting element 6, FIG. 45 shows its luminance versus voltage characteristics, FIG. 46 shows its current efficiency versus luminance characteristics, and FIG. 47 shows its current versus voltage characteristics. In FIG. 40 and FIG. 44, the vertical axis represents luminance (cd/m$^2$) and the horizontal axis represents current density (mA/cm$^2$). In FIG. 41 and FIG. 45, the vertical axis represents luminance (cd/m$^2$) and the horizontal axis represents voltage (V). In FIG. 42 and FIG. 46, the vertical axis represents current efficiency (cd/A) and the horizontal axis represents luminance (cd/m$^2$). In FIG. 43 and FIG. 47, the vertical axis represents current (mA) and the horizontal axis represents voltage (V).

FIG. 42 shows the favorable current efficiency versus luminance characteristics of the light-emitting element 5, in which the carbazole compound represented by the general formula (G1) was used for the host material of the light-emitting layer exhibiting blue phosphorescence. Thus, the element is found to have high emission efficiency. This is because the carbazole compound represented by the general formula (G1) has high triplet excitation energy and a wide energy gap such that even a light-emitting substance that emits blue phosphorescence can be effectively excited. In addition, FIG. 41 shows the favorable luminance versus voltage characteristics of the light-emitting element in which the carbazole compound represented by the general formula (G1) was used for the host material of the light-emitting layer exhibiting blue phosphorescence. Thus, the element is found to have low driving voltage. This means that the carbazole compound represented by the general formula (G1) has an excellent carrier-transport property.

FIG. 46 shows the favorable current efficiency versus luminance characteristics of the light-emitting element 6, in which the carbazole compound represented by the general formula (G1) was used for the hole-transport material adjacent to the light-emitting layer exhibiting blue phosphorescence. Thus, the element is found to have high emission efficiency. This is because since mDBTCz2P-II, which is a carbazole compound described in Embodiment 1, has a wide energy gap and a high triplet excitation energy accordingly, even when it is used for the hole-transport layer adjacent to the emission center substance that emits blue phosphorescence, a reduction in emission efficiency is suppressed without transfer of excitation energy to the hole-transport layer. In addition, FIG. 45 shows the favorable luminance versus voltage characteristics of the light-emitting element, in which the carbazole compound represented by the general formula (G1) was used for the host material of the light-emitting layer exhibiting blue phosphorescence. Thus, the element is found to have low driving voltage. This means that the carbazole compound represented by the general formula (G1) has an excellent carrier-transport property.

Figure 48:
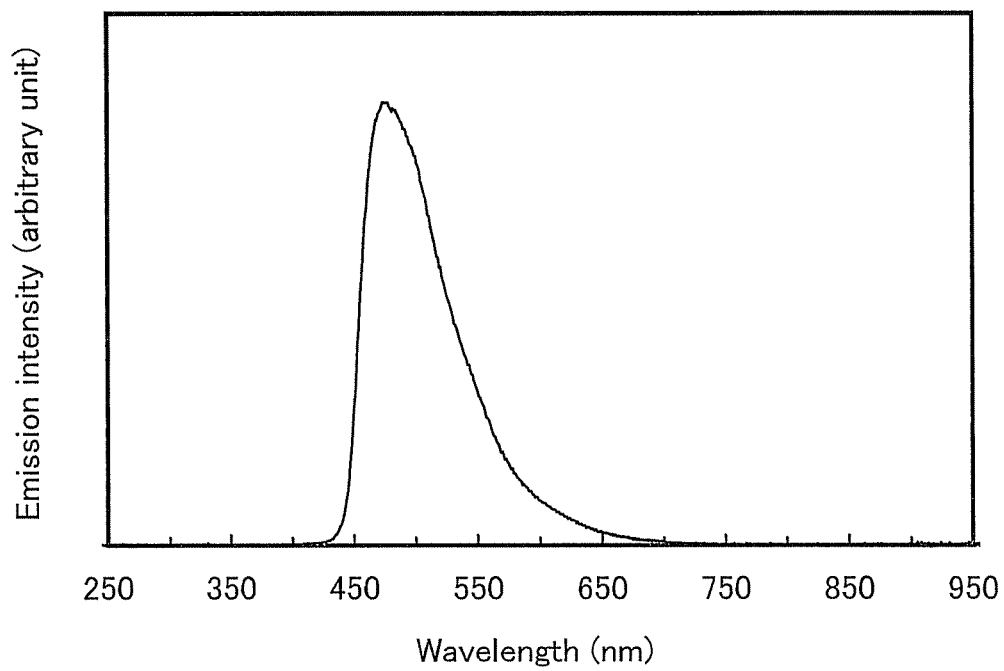
FIG. 48 shows an emission spectrum of the light-emitting element 5.
Figure 49:
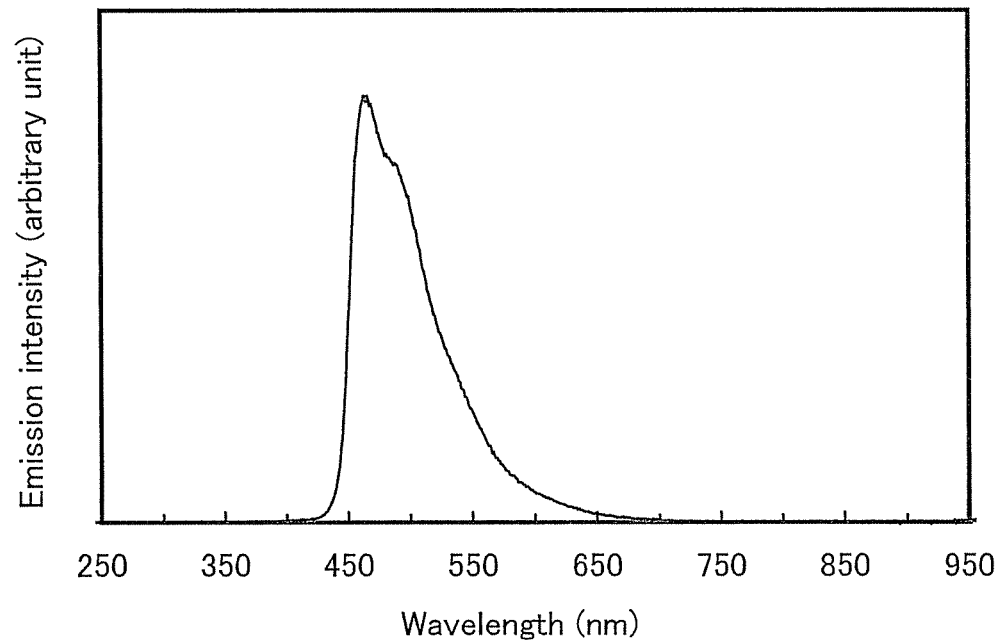
FIG. 49 shows an emission spectrum of the light-emitting element 6.

FIG. 48 shows an emission spectrum when a current of 0.1 mA was made to flow in the fabricated light-emitting element 5, and FIG. 49 shows an emission spectrum when a current of 0.1 mA was made to flow in the light-emitting element 6. In FIG. 48 and FIG. 49, the vertical axis represents emission intensity (arbitrary unit) and the horizontal axis represents wavelength (nm). The emission intensity is shown as a value relative to the greatest emission intensity assumed to be 1. FIG. 48 and FIG. 49 indicate that each of the light-emitting elements 5 and 6 emit blue light that originates from [Ir(Mptzl-mp)$_3$], which was the emission center substance.

Figure 50:
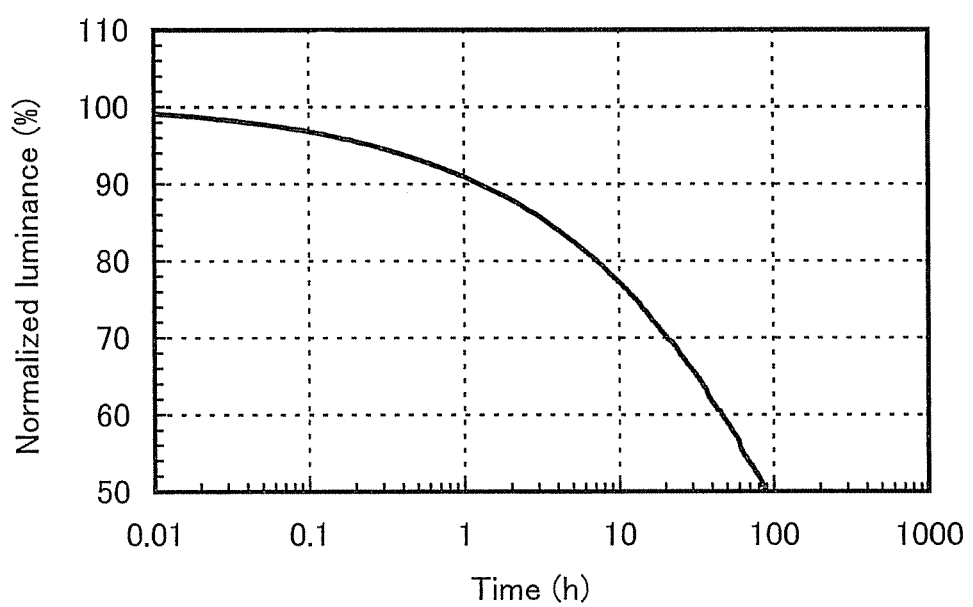
FIG. 50 shows normalized luminance versus time characteristics of the light-emitting element 5.
Figure 51:
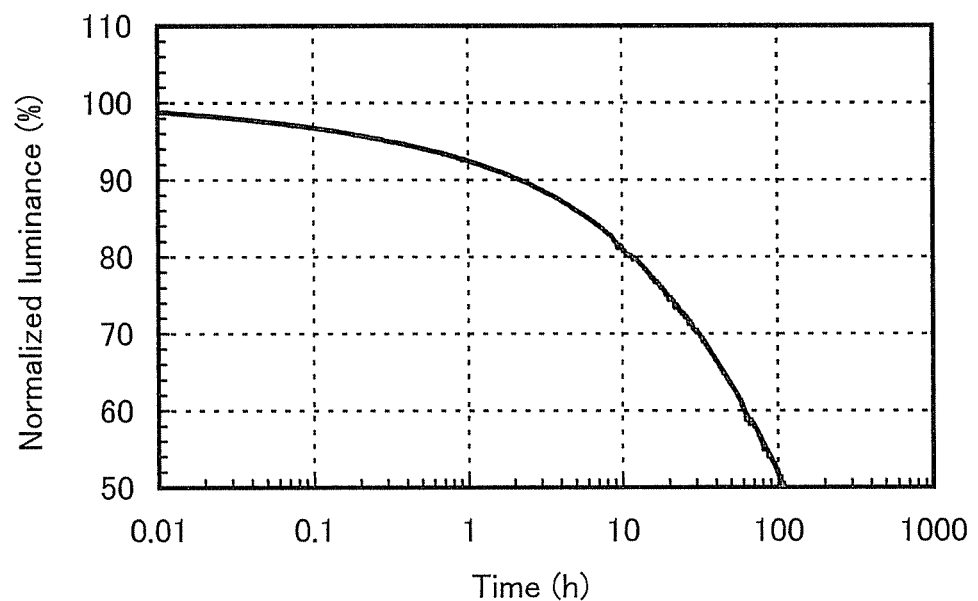
FIG. 51 shows normalized luminance versus time characteristics of the light-emitting element 6.

Next, with an initial luminance set to 1000 cd/m$^2$, these elements were driven under a condition where the current density was constant, and changes in luminance relative to driving time were examined. FIG. 50 shows normalized luminance versus time characteristics of the light-emitting element 5, and FIG. 51 shows those of the light-emitting element 6. As can be seen from FIG. 50 and FIG. 51, the decrease in the luminance of each of the light-emitting elements 5 and 6 relative to driving time is small. Thus, each element is found to have high reliability.

Thus, a light-emitting element, in which an emission center substance emits blue phosphorescence and a carbazole compound described in Embodiment 1 is used for a host material or for a hole-transport material, can have high emission efficiency by efficient excitation for blue phosphorescence which is the light emission from the high triplet excitation energy or by prevention of a loss due to energy transfer. This demonstrates the high very triplet excitation energy of the carbazole compound described in Embodiment 1.

Example 6

Synthesis Example 2

In this example is specifically described a method of synthesizing 3,3'-bis(dibenzothiophen-4-yl)-N,N'-(3,3'-biphenyl)bicarbazole (abbreviation: mDBTCz2BP-II), which is represented by the structural formula (103) in Embodiment 1, and characteristics of this compound. A structural formula of mDBTCz2P-II is shown below.

(103)

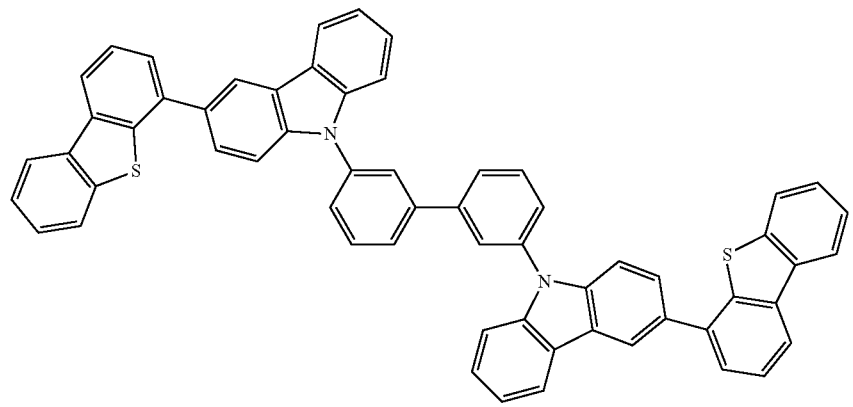

Step 1: Synthesis of 3-(Dibenzothiophen-4-yl)-9H-carbazole

This was synthesized as in a manner similar to that of Step 1 in Synthesis Example 1.

Step 2: Synthesis of 3,3'-Bis(dibenzothiophen-4-yl)-N,N'-(3,3'-biphenyl)bicarbazole (abbreviation: mDBTCz2BP-II)

Into a 200 mL three-neck flask were placed 5.79 g (16.6 mmol) of 3-(dibenzothiophen-4-yl)-9H-carbazole and 4.2 g (43.3 mmol) of sodium tert-butoxide, and the air in the flask was replaced with nitrogen. To this mixture were added 20.0 mL of xylene, 0.5 mL of a 10% hexane solution of 2.3 g (7.2 mmol) of 3,3'-dibromobiphenyl and tri(tert-butyl)phosphine dissolved in 30 mL of xylene, and 67.1 mg (0.1 mmol) of bis(dibenzylideneacetone)palladium(0). The temperature was adjusted to 130° C. and the mixture was stirred for 22.5 hours. Two and a half hours after the start of the stirring with the temperature adjusted to 130° C., 71.2 mg (0.1 mmol) of bis(dibenzylideneacetone)palladium(0) was added to the mixture. Nine hours after the start of the stirring, 67.1 mg (0.1 mmol) of bis(dibenzylideneacetone)palladium(0) was added to the mixture. Twelve hours after the start of the stirring, 0.8 mL of a 10% hexane solution of tri(tert-butyl)phosphine was added to the mixture. Thirteen and a half hours after the start of the stirring, 1.5 mL of a 10% hexane solution of tri(tert-butyl)phosphine was added to the mixture. Fourteen hours after the start of the stirring, 54.1 mg (0.1 mmol) of bis(dibenzylideneacetone)palladium(0) was added to the mixture. Eighteen hours after the start of the stirring, 41.5 mg (0.1 mmol) of bis(dibenzylideneacetone)palladium(0) and 0.5 mL of a 10% hexane solution of tri(tert-butyl)phosphine were added to the mixture. After the stirring, suction filtration was carried out to give a filtrate and a residue. The obtained residue was washed with water and ethanol, and the resulting mixture was dissolved in toluene. The obtained filtrate and the mixture dissolved in toluene were suction filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The obtained filtrate was concentrated to give a solid. The obtained solid was purified by silica gel column chromatography (with a developing solvent containing hexane and toluene in a 3:2 ratio), whereby a solid was obtained. The obtained solid was recrystallized from toluene and hexane, so that 1.8 g of a solid which was the object of the synthesis was obtained in a yield of 29%. The synthesis scheme of Step 2 is illustrated in the following scheme (b-2).

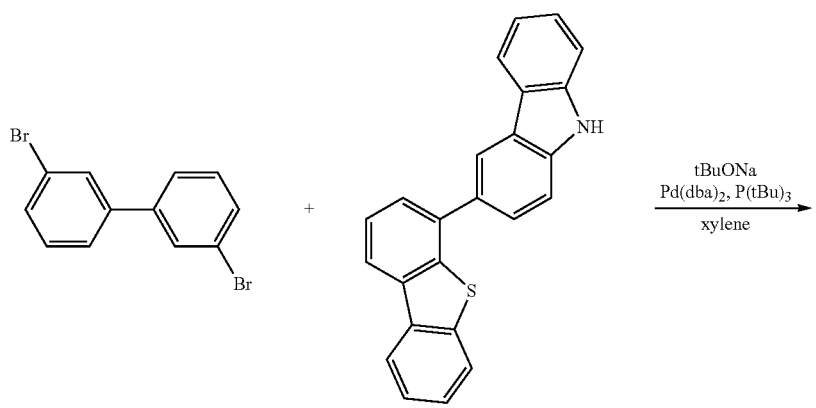

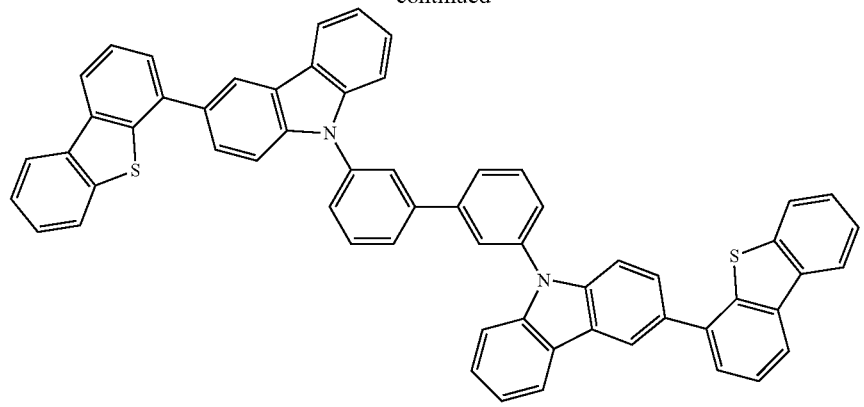

Using a train sublimation method, 1.0 g of the obtained solid was purified by sublimation. In the purification by sublimation, the solid was heated at 352° C. under a pressure of 2.6 Pa with a flow rate of argon gas of 5.0 mL/min. After the purification by sublimation, 0.9 g of a solid which was the object of the synthesis was recovered in a yield of 90%.

Figure 52A:
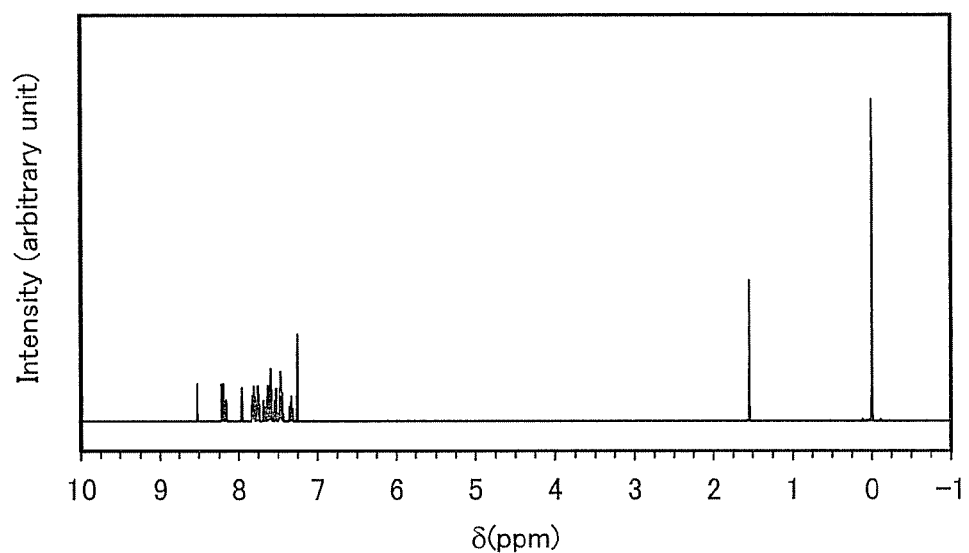
FIGS. 52A and 52B are NMR charts of mDBTCz2BP-II.
Figure 52B:
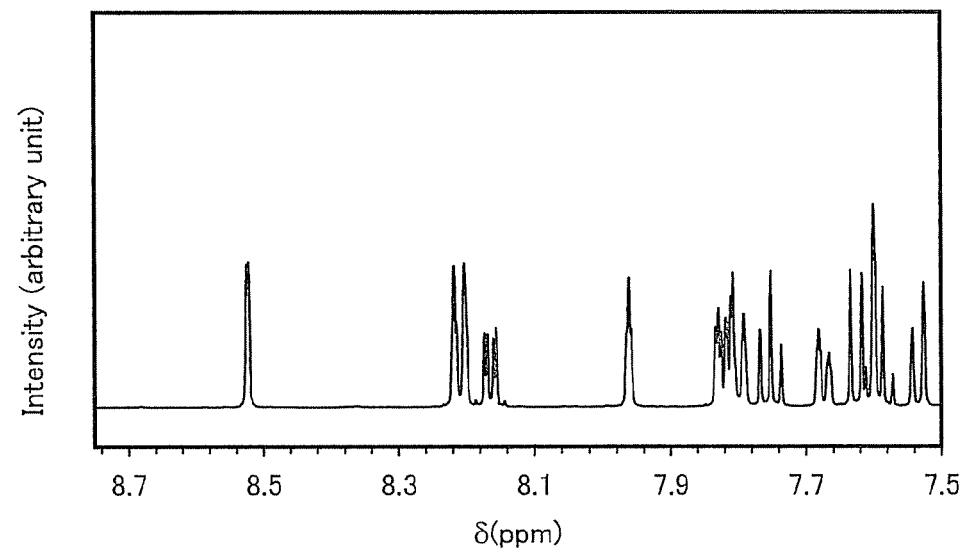

This compound was subjected to nuclear magnetic resonance (NMR) spectroscopy. The obtained NMR charts are shown in FIGS. 52A and 52B. Note that FIG. 52B is a chart where the range of from 7.5 ppm to 8.75 ppm in FIG. 52A is enlarged. In addition, $^1$H NMR data of the obtained compound is shown below.

$^1$H NMR (CDCl$_3$, 500 M Hz): δ (ppm)=7.33 (t, J=7.5 Hz, 2H), 7.43-7.49 (m, 6H), 7.53 (d, J=7.8 Hz, 2H), 7.57-7.64 (m, 6H), 7.67 (d, J=8.0 Hz, 2H), 7.75 (t, J=7.5 Hz, 2H), 7.79-7.83 (m, 6H), 7.96 (s, 2H), 8.17 (dd, J=2.5 Hz, 6.5 Hz, 2H), 8.21 (d, J=7.5 Hz, 4H), 8.52 (d, J=2.0 Hz, 2H)

Thus, the solid obtained in this synthesis example was confirmed to be 3,3'-bis(dibenzothiophen-4-yl)-N,N'-(3,3'-biphenyl)bicarbazole (abbreviation: mDBTCz2BP-II).

Physical Properties of mDBTCz2BP-II

Thermogravimetry-differential thermal analysis (TG-DTA) of mDBTCz2BP-II, which was obtained, was performed. For the measurement, a high vacuum differential type differential thermal balance (manufactured by Bruker AXS K.K., TG/DTA 2410SA) was used. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 500° C. or more, which is indicative of high heat resistance.

Figure 53:
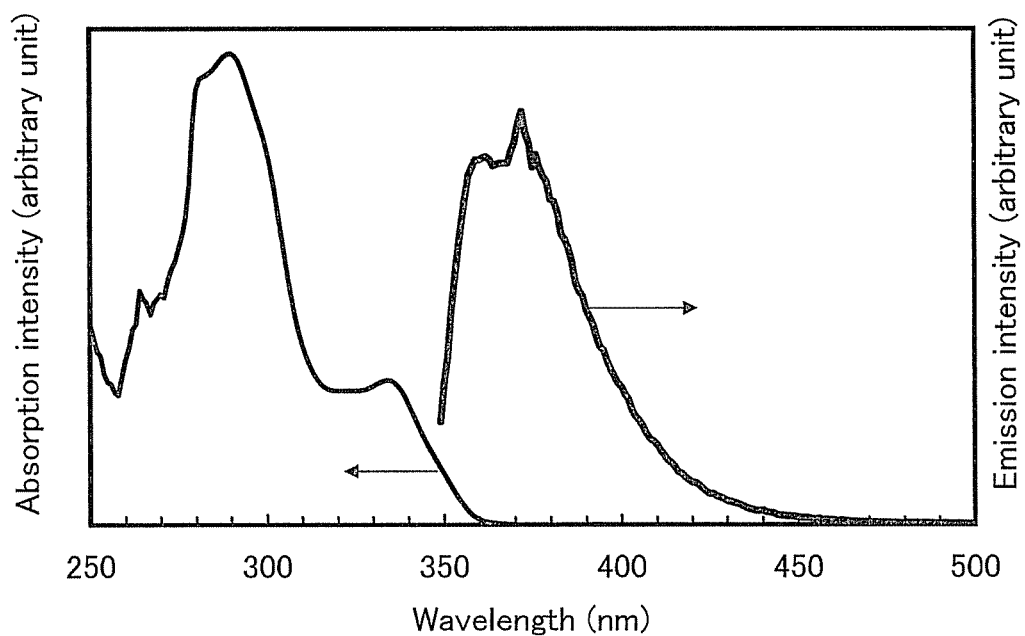
FIG. 53 shows an absorption and emission spectra of mDBTCz2BP-II in a toluene solution of mDBTCz2BP-II.

An absorption and emission spectra of mDBTCz2BP-II in a toluene solution of mDBTCz2BP-II are shown in FIG. 53. An ultraviolet-visible spectrophotometer (V-550, produced by JASCO Corporation) was used for the measurements of the spectra. The spectra of the toluene solution were measured with a toluene solution of mDBTCz2BP-II put in a quartz cell. FIG. 53 shows the absorption spectrum of the toluene solution which was obtained by subtraction of the absorption spectra of quartz and toluene from the measured spectra.

FIG. 53 shows that the absorption peak wavelengths of mDBTCz2BP-II in the toluene solution of mDBTCz2BP-II were around 334 nm, 290 nm, 281 nm, and 264 nm, and the emission peak wavelength thereof was around 372 nm and 362 nm (at an excitation wavelength of 334 nm).

Electrochemical characteristics (oxidation and reduction characteristics) of a solution of mDBTCz2BP-II were measured by cyclic voltammetry (CV). Note that an electrochemical analyzer (ALS model 600A or 600C, produced by BAS Inc.) was used for the measurements.

In the measurements, the potential of a working electrode with respect to the reference electrode was changed within an appropriate range, so that the oxidation peak potential and the reduction peak potential were each obtained. From the obtained peak potentials, the HOMO and LUMO levels of mDBTCz2BP-II were respectively calculated at −5.87 eV and −2.26 eV.

The calculations of the HOMO and LUMO levels using CV measurement are detailed below.

For a solution for the CV measurements, dehydrated N,N-dimethylformamide (DMF, produced by Sigma-Aldrich Inc., 99.8%, catalog No. 22705-6) was used as a solvent, and tetra-n-butylammonium perchlorate (n-Bu$_4$NClO$_4$, produced by Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L.

A platinum electrode (a PTE platinum electrode, produced by BAS Inc.) was used as the working electrode; a platinum electrode (a VC-3 Pt counter electrode (5 cm), produced by BAS Inc.) was used as an auxiliary electrode; and an Ag/Ag$^+$ electrode (an RE5 nonaqueous solvent reference electrode, produced by BAS Inc.) was used as the reference electrode. Note that the measurements were conducted at room temperature (20° C. to 25° C.). The scan rates for the CV measurements were uniformly set to 0.1 V/s.

In the measurement of the oxidation characteristics, one cycle was scanning in which the potential of the working electrode with respect to the reference electrode was changed from 0.11 V to 1.10 V and then changed from 1.10 V to 0.11 V.

In the measurements of the reduction characteristics, one cycle was scanning in which the potential of the working electrode with respect to the reference electrode was changed from −1.51 V to −2.82 V and then changed from −2.82 V to −1.51 V.

The HOMO level was obtained by subtraction of a half-wave potential $E_{1/2}$ (an intermediate potential between $E_{pa}$ and $E_{pc}$), which was calculated from the oxidation peak potential $E_{pa}$ and reduction peak potential $E_{pc}$ obtained in the measurement of the oxidation characteristics of mDBTCz2BP-II, from the potential energy of the reference electrode, which was used, with respect to the vacuum level.

The oxidation peak potential $E_{pa}$ was 1.00 V and the reduction peak potential $E_{pc}$ was 0.86 V according to the measurement of the oxidation characteristics of mDBTCz2BP-II. The half-wave potential $E_{1/2}$ was therefore 0.93 V, and since the potential energy of the reference electrode, which was used in the measurements, with respect to the vacuum level is −4.94 eV, the HOMO level of the solution of mDBTCz2BP-II can be calculated as follows: −4.94−0.93=−5.87 eV.

The LUMO level was obtained by subtraction of a half-wave potential $E_{12}$ (an intermediate potential between $E_{pa}$ and $E_{pc}$), which was calculated from the reduction peak potential $E_{pc}$ and oxidation peak potential $E_{pa}$ obtained in the measurement of the reduction characteristics of mDBTCz2BP-II, from the potential energy of the reference electrode, which was used, with respect to the vacuum level.

The reduction peak potential $E_{pa}$ was −2.75V and the oxidation peak potential $E_{pc}$ was −2.61 according to the measurement of the reduction characteristics of mDBTCz2BP-II. The half-wave potential $E_{1/2}$ was therefore −2.68 V, and since the potential energy of the reference electrode, which was used in the measurements, with respect to the vacuum level is −4.94 eV, the LUMO level of the solution of mDBTCz2BP-II can be calculated as follows: −4.94−(−2.68)=−2.26 eV.

Note that the potential energy of the reference electrode (Ag/Ag$^+$ electrode) with respect to the vacuum level corresponds to the Fermi level of the Ag/Ag$^+$ electrode, and should be calculated from a value obtained by measuring a substance whose potential energy with respect to the vacuum level is known, with the use of the reference electrode (Ag/Ag$^+$ electrode).

How the potential energy (eV) of the reference electrode (Ag/Ag$^+$ electrode), which was used in this example, with respect to the vacuum level is calculated will be specifically described. It is known that the oxidation-reduction potential of ferrocene in methanol is +0.610 V [vs. SHE] with respect to the standard hydrogen electrode (reference: Christian R. Goldsmith et al., *J. Am. Chem. Soc.*, Vol. 124, No. 1, pp. 83-96, 2002). In contrast, using the reference electrode used in this example, the oxidation-reduction potential of ferrocene in methanol was calculated at +0.11 V [vs. Ag/Ag$^+$]. Thus, it was found that the potential energy of this reference electrode was lower than that of the standard hydrogen electrode by 0.50 [eV].

Here, it is known that the potential energy of the standard hydrogen electrode with respect to the vacuum level is −4.44 eV (reference: Toshihiro Ohnishi and Tamami Koyama, *High molecular EL material*, Kyoritsu shuppan, pp. 64-67). Therefore, the potential energy of the reference electrode, which was used in this example, with respect to the vacuum level can be calculated as follows: −4.44−0.50=−4.94 [eV].

Reference Example

In this reference example, materials used in Examples are described.

Synthesis Example of 1,6mMemFLPAPrn

Here is described an example in which N'-bis(3-methylphenyl)-N,N-bis[3-(9-phenyl-9H-fluoren-9-yl)phenyl]-pyrene-1,6-diamine (abbreviation: 1,6mMemFLPAPrn), which was used for a material of the light-emitting element 1, is synthesized.

Step 1: Synthesis of Synthesizing 3-Methylphenyl-3-(9-phenyl-9H-fluoren-9-yl)phenylamine (abbreviation: mMemFLPA)

Into a 200 mL three-neck flask were placed 3.2 g (8.1 mmol) of 9-(3-bromophenyl)-9-phenylfluorene and 2.3 g (24.1 mmol) of sodium tert-butoxide. The air in the flask was replaced with nitrogen. To this mixture were added 40.0 mL of toluene, 0.9 mL (8.3 mmol) of m-toluidine, and 0.2 mL of a 10% hexane solution of tri(tert-butyl)phosphine. The temperature of this mixture was set to 60° C., and 44.5 mg (0.1 mmol) of bis(dibenzylideneacetone)palladium(0) was added to the mixture. The temperature of this mixture was raised to 80° C., and the mixture was stirred for 2.0 hours. After that, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. A solid obtained by concentration of the obtained filtrate was purified by silica gel column chromatography (a developing solvent in which the ratio of hexane to toluene was 1:1) and recrystallized from a mixed solvent of toluene and hexane. Accordingly, 2.8 g of a white solid of the object of the synthesis was obtained in 82% yield. The synthesis scheme of Step 1 above is illustrated in the following scheme.

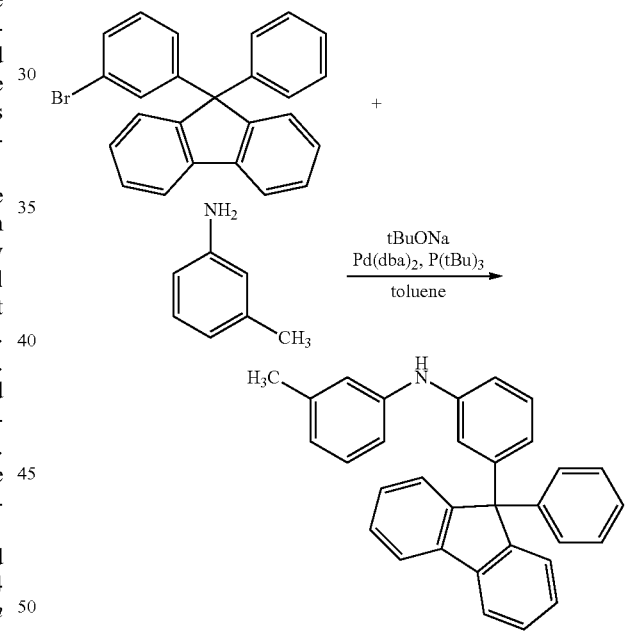

Step 2: Method of Synthesizing N,N'-Bis(3-methylphenyl)-N,N'-bis[3-(9-phenyl-9H-fluoren-9-yl)phenyl]-pyrene-1,6-diamine (abbreviation: 1,6mMemFLPAPrn)

Into a 100 mL three-neck flask were placed 0.6 g (1.7 mmol) of 1,6-dibromopyrene, 1.4 g (3.4 mmol) of 3-methylphenyl-3-(9-phenyl-9H-fluoren-9-yl)phenylamine, and 0.5 g (5.1 mmol) of sodium tert-butoxide. The air in the flask was replaced with nitrogen. To this mixture were added 21.0 mL of toluene and 0.2 mL of a 10% hexane solution of tri(tert-butyl)phosphine. The temperature of this mixture was set to 60° C., and 34.9 mg (0.1 mmol) of bis(dibenzylideneacetone) palladium(0) was added to the mixture. The temperature of this mixture was raised to 80° C., and the mixture was stirred for 3.0 hours. After that, 400 mL of toluene was added to the mixture, and the mixture was heated. While kept hot, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (a developing solvent in which the ratio of hexane to toluene was 3:2) to give a yellow solid. Recrystallization of the obtained yellow solid from a mixed solvent of toluene and hexane gave 1.2 g of a yellow solid of the object of the synthesis in 67% yield.

By a train sublimation method, 1.0 g of the obtained yellow solid was purified by sublimation. In the sublimation purification by sublimation, the yellow solid was heated at 317° C. under a pressure of 2.2 Pa with a flow rate of argon gas of 5.0 mL/min. After the sublimation purification by sublimation, 1.0 g of a yellow solid of the object of the synthesis was obtained in a yield of 93%. The synthesis scheme of Step 2 above is shown in the following scheme.

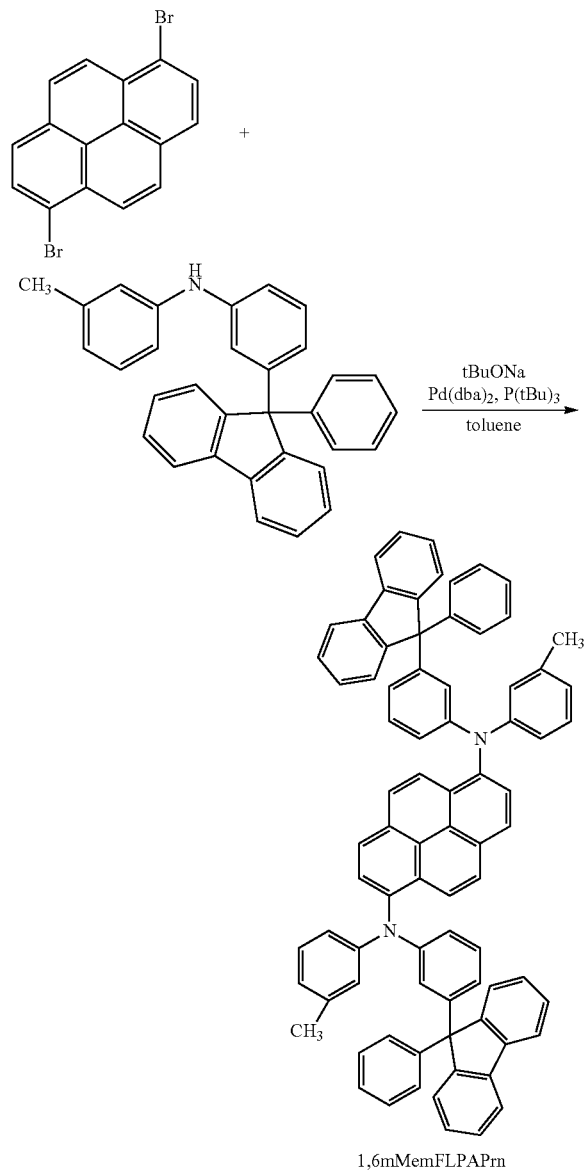

1,6mMemFLPAPrn

A nuclear magnetic resonance (NMR) method identified this compound as N,N'-bis(3-methylphenyl)-N,N'-bis[3-(9-phenyl-9H-fluoren-9-yl)phenyl]-pyrene-1,6-diamine (abbreviation: 1,6mMemFLPAPrn), which was the object of the synthesis.

$^1$H NMR data of the obtained compound is shown below.
$^1$H NMR (CDCl$_3$, 300 MHz): δ=2.21 (s, 6H), 6.67 (d, J=7.2 Hz, 2H), 6.74 (d, J=7.2 Hz, 2H), 7.17-7.23 (m, 34H), 7.62 (d, J=7.8 Hz, 4H), 7.74 (d, J=7.8 Hz, 2H), 7.86 (d, J=9.0 Hz, 2H), 8.04 (d, J=8.7 Hz, 4H).

Synthesis Example of mDBTBIm-II

A synthesis example of 2-[3-(dibenzothiophen-4-yl)phenyl]-1-phenyl-1H-benzimidazole (abbreviation: mDBTBIm-II), which was used for a material of the light-emitting elements 2 to 6, will be described.

Synthesis of 2-[3-(Dibenzothiophen-4-yl)phenyl]-1-phenyl-1H-benzimidazole (abbreviation: mDBTBIm-II)

Into a 50-mL three-neck flask were put 1.2 g (3.3 mmol) of 2-(3-bromophenyl)-1-phenyl-1H-benzimidazole, 0.8 g (3.3 mmol) of dibenzothiophene-4-boronic acid, and 50 mg (0.2 mmol) of tri(ortho-tolyl)phosphine. The air in the flask was replaced with nitrogen. To this mixture were added 3.3 mL of a 2.0 mmol/L aqueous solution of potassium carbonate, 12 mL of toluene, and 4 mL of ethanol. Under reduced pressure, this mixture was stirred to be degassed. Then, 7.4 mg (33 μmol) of palladium(II) acetate was added to this mixture, and the mixture was stirred at 80° C. for 6 hours under a nitrogen stream. After a predetermined time, the aqueous layer of the obtained mixture was subjected to extraction with toluene. The solution of the obtained extract combined with the organic layer was washed with saturated brine, and then the organic layer was dried over magnesium sulfate. This mixture was separated by gravity filtration, and the filtrate was concentrated to give an oily substance. This oily substance was purified by silica gel column chromatography. The silica gel column chromatography was carried out using toluene as a developing solvent. The obtained fraction was concentrated to give an oily substance. This oily substance was purified by high performance liquid chromatography. The high performance liquid chromatography was performed using chloroform as a developing solvent. The obtained fraction was concentrated to give an oily substance. This oily substance was recrystallized from a mixed solvent of toluene and hexane, so that the substance which was the object of the synthesis was obtained as 0.8 g of a pale yellow powder in 51% yield. The synthesis scheme is illustrated in the following formula.

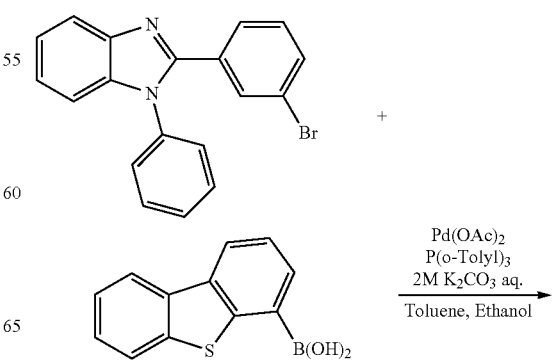

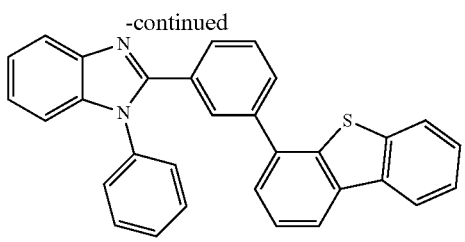

By a train sublimation method, 0.8 g of the obtained pale yellow powder was purified by sublimation. In the purification by sublimation, the pale yellow powder was heated at 215° C. under a pressure of 3.0 Pa with a flow rate of argon gas of 5 mL/min. After the purification by sublimation, 0.6 g of a white powder of the substance which was the object of the synthesis was obtained in a yield of 82%.

This compound was identified as 2-[3-(dibenzothiophen-4-yl)phenyl]-1-phenyl-1H-benzimidazole (abbreviation: mDBTBIm-II), which was the object of the synthesis, by nuclear magnetic resonance (NMR) spectroscopy.

$^1$H NMR data of the obtained compound are as follows: $^1$H NMR (CDCl$_3$, 300 MHz): δ (ppm)=7.23-7.60 (m, 13H), 7.71-7.82 (m, 3H), 7.90-7.92 (m, 2H), 8.10-8.17 (m, 2H).

Synthesis Example of [Ir(Mptz)$_3$]

A synthesis example of tris(5-methyl-3,4-diphenyl-4H-1,2,4-triazolato)iridium(III) (abbreviation: [Ir(Mptz)$_3$]), which was used for a material of the light-emitting elements 3 and 4, will be described.

Step 1: Synthesis of 3-Methyl-4,5-diphenyl-4H-1,2,4-triazole (abbreviation: HMptz)

First, 5.04 g of thioacetanilide, 5.44 g of benzoylhydrazine, and 50 mL of 1-butanol were put in a round-bottom flask provided with a reflux pipe, and the air in the flask was replaced with argon. This reaction container was subjected to irradiation with a microwave (2.45 GHz, 100 W) for 2 hours and 45 minutes to perform heating. Then, water was added to this solution and an organic layer was extracted with dichloromethane. The obtained organic layer was washed with water and dried over magnesium sulfate. After the drying, the solution was filtered. The solvent of this solution was distilled off, and the resulting residue was purified by silica gel column chromatography which uses ethyl acetate as a developing solvent, so that 3-methyl-4,5-diphenyl-4H-1,2,4-triazole (abbreviation: HMptz) was obtained (pale yellow powder, 18% yield). The synthesis scheme of Step 1 is shown below.

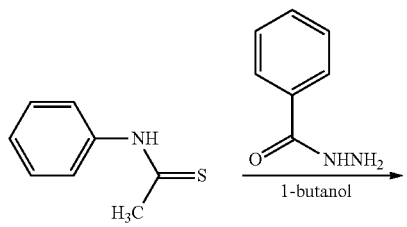

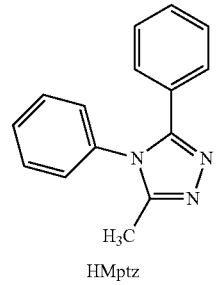

Step 2: Synthesis of Tris(5-methyl-3,4-diphenyl-4H-1,2,4-triazolato)iridium(III) (abbreviation: [Ir(Mptz)$_3$])

Next, 1.40 g of the ligand HMptz, which was prepared in Step 1 above, and 0.58 g of tris(acetylacetonato)iridium(III) were put in a reaction container provided with a three-way cock, and the air in the reaction container was replaced with argon. Then, the mixture was heated at 250° C. for 17 hours and 30 minutes to be reacted. The reactant was dissolved in dichloromethane, and the solution was filtered. The solvent of the resulting filtrate was distilled off and purification was conducted by silica gel column chromatography which uses ethyl acetate as a developing solvent. Further, recrystallization was carried out with a mixed solvent of dichloromethane and hexane, so that the organometallic complex [Ir(Mptz)$_3$] was prepared (yellow powder, 22% yield). The synthesis scheme of Step 2 is shown below.

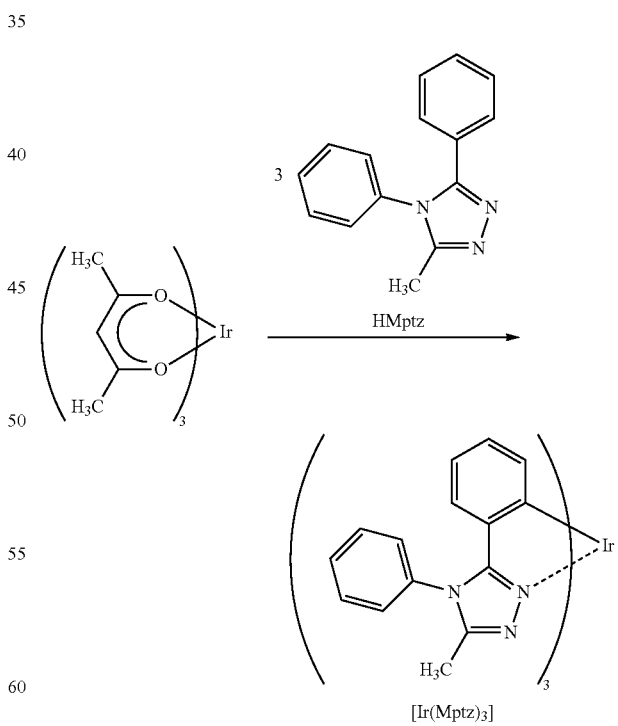

Analysis results by nuclear magnetic resonance ($^1$H-NMR) spectroscopy of the yellow powder prepared in Step 2 described above are shown below. These results indicate that the organometallic complex Ir(Mptz)$_3$ was obtained.

$^1$H NMR. δ (CDCl$_3$): 2.17 (s, 9H), 6.38 (d, 3H), 6.54 (t, 3H), 6.72 (dt, 3H), 6.87 (dd, 3H), 7.34 (m, 3H), 7.51 (b, 3H), 7.57 (m, 9H).

Synthesis Example of [Ir(Mptzl-mp)$_3$]

A synthesis example of tris[3-methyl-1-(2-methylphenyl)-5-phenyl-1H-1,2,4-triazolato]iridium(III) (abbreviation: [Ir(Mptzl-mp)$_3$]), which was used for a material of the light-emitting elements 5 and 6, will be described.

Step 1: Synthesis of N-(1-Ethoxyethylidene)benzamide

First, 15.5 g of ethyl acetimidate hydrochloride, 150 mL of toluene, and 31.9 g of triethylamine (Et$_3$N) were put into a 500-mL three-neck flask and stirred at room temperature for 10 minutes. With a 50-mL dropping funnel, a mixed solution of 17.7 g of benzoyl chloride and 30 mL of toluene were added dropwise to this mixture, and the mixture was stirred at room temperature for 24 hours. After a predetermined time elapsed, the reaction mixture was suction-filtered, and the solid was washed with toluene. The obtained filtrate was concentrated to give N-(1-ethoxyethylidene)benzamide (a red oily substance, 82% yield). A scheme of the synthesis of Step 1 is shown below.

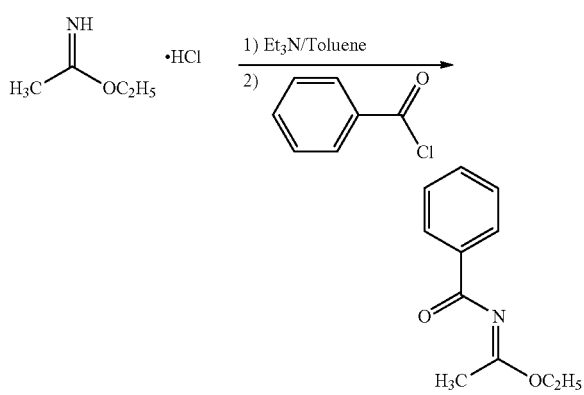

Step 2: Synthesis of 3-Methyl-1-(2-methylphenyl)-5-phenyl-1H-1,2,4-triazole (abbreviation: HMptzl-mp)

Next, into a 300-mL recovery flask were put 8.68 g of o-tolyl hydrazine hydrochloride, 100 mL of carbon tetrachloride, and 35 mL of triethylamine (Et$_3$N), and the mixture was stirred at room temperature for 1 hour. After a predetermined time elapsed, 8.72 g of N-(1-ethoxyethylidene)benzamide obtained in the above Step 1 was added to this mixture, and the mixture was stirred at room temperature for 24 hours. After a predetermined time elapsed, water was added to the reaction mixture, and the aqueous layer was subjected to extraction with chloroform. The organic layer of the resulting mixture was washed with saturated brine, and dried with anhydrous magnesium sulfate added thereto. The obtained mixture was gravity-filtered, and the filtrate was concentrated to give an oily substance. The obtained oily substance was purified by silica gel column chromatography. Dichloromethane was used as a developing solvent. The obtained fraction was concentrated to give 3-methyl-1-(2-methylphenyl)-5-phenyl-1H-1,2,4-triazole (abbreviation: HMptzl-mp) (an orange oily substance, 84% yield). A synthesis scheme of Step 2 is shown below.

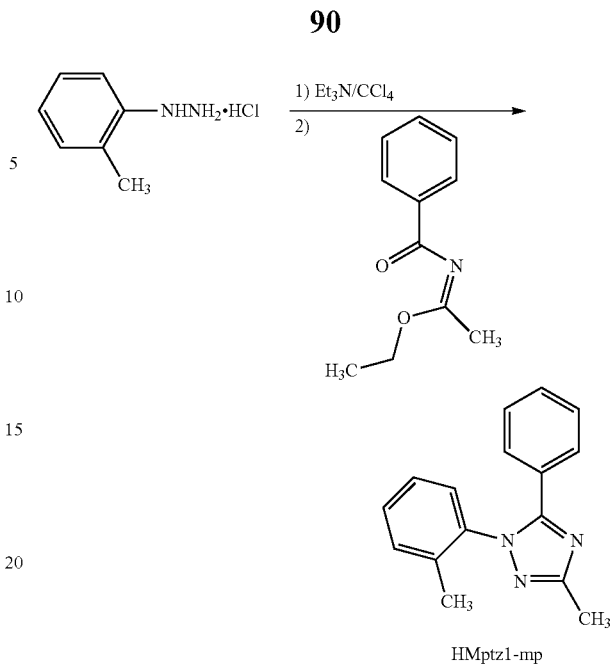

Step 3: Synthesis of Tris[3-methyl-1-(2-methylphenyl)-5-phenyl-1H-1,2,4-triazolato]iridium(III) (abbreviation: [Ir(Mptzl-mp)$_3$])

Next, 2.71 g of the ligand HMptzl-mp obtained in the above Step 2 and 1.06 g of tris(acetylacetonato)iridium(III) were put into a reaction container provided with a three-way cock. The air in this flask was replaced with argon, and heated at 250° C. for 48 hours to be reacted. This reaction mixture was dissolved in dichloromethane and purified by silica gel column chromatography. As the developing solvent, dichloromethane was first used, and a mixed solvent of dichloromethane and ethyl acetate in a ratio of 10:1 (v/v) was then used. The obtained fraction was concentrated to give a solid. This solid was washed with ethyl acetate, and recrystallized from a mixed solvent of dichloromethane and ethyl acetate to give the organometallic complex Ir(Mptzl-mp)$_3$ (a yellow powder, 35% yield). A scheme of the synthesis of Step 3 is shown below.

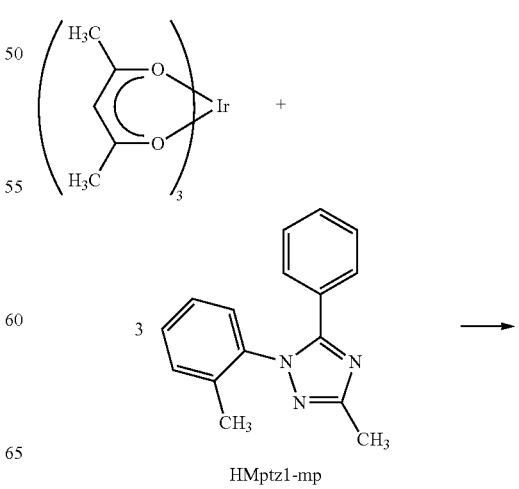

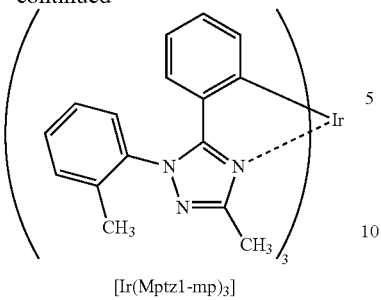

[Ir(Mptz1-mp)₃]

Analysis results by nuclear magnetic resonance spectrometry (¹H-NMR) of the yellow powder obtained in the above Step 3 are shown below. Thus, [Ir(Mptz1-mp)₃] was found to be obtained.

¹H NMR data of the obtained substance are as follows: ¹H NMR (CDCl₃): 1.94-2.21 (m, 18H), 6.47-6.76 (m, 12H), 7.29-7.52 (m, 12H).

This application is based on Japanese Patent Application Serial No. 2011-108093 filed with the Japan Patent Office on May 13, 2011, the entire contents of which are hereby incorporated by reference.

What is claimed is:

1. A compound represented by a formula (G1):

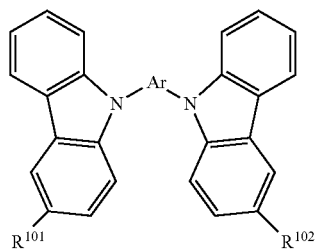

(G1)

wherein Ar represents a substituted or unsubstituted phenylene group or a substituted or unsubstituted biphenyldiyl group, and wherein $R^{101}$ and $R^{102}$ each independently represent a group represented by a formula (g1):

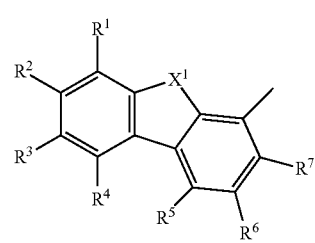

(g1)

wherein $X^1$ represents sulfur or oxygen, and wherein $R^1$ to $R^7$ each independently represent any of hydrogen, an alkyl group having 1 to 4 carbon atoms, or an aryl group having 6 to 12 carbon atoms.

2. The compound according to claim 1, wherein the compound is represented by a formula (G3):

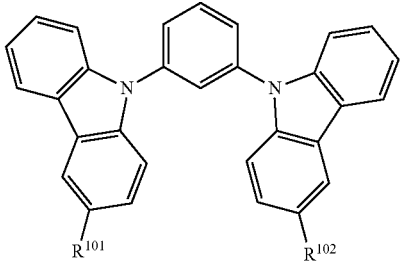

(G3)

3. The compound according to claim 1, wherein the compound is represented by a formula (G4):

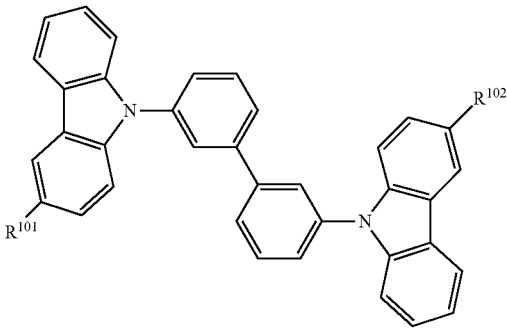

(G4)

4. The compound according to claim 1, wherein the group represented by the formula (g1) is represented by a formula (g3):

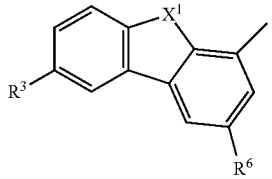

(g3)

5. The compound according to claim 1, wherein the group represented by the formula (g1) is represented by a formula (g5):

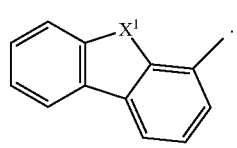

(g5)

6. The compound according to claim 1, wherein $X^1$ represents sulfur.

7. The compound according to claim 1, wherein $R^{101}$ and $R^{102}$ the same.

8. The compound according to claim 1, wherein the compound is represented by a formula (100):

(100)

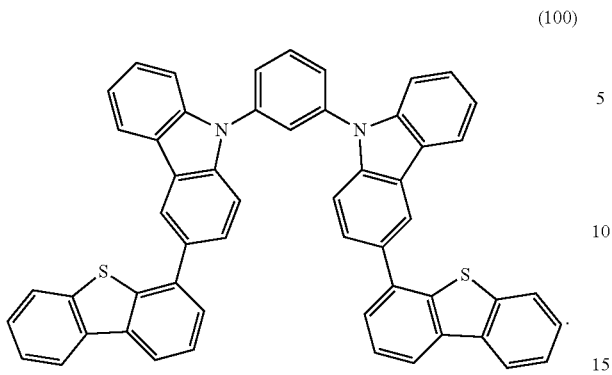

9. The compound according to claim 1, wherein the compound is represented by a formula (106):

(106)

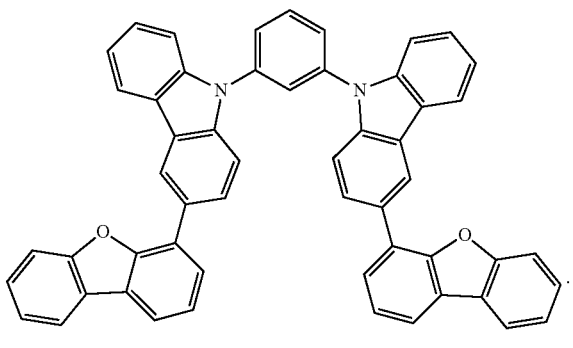

10. A light-emitting material comprising the compound according to claim 1.

11. An organic semiconductor material comprising the compound according to claim 1.

12. A light-emitting device comprising a light-emitting element, the light-emitting element comprising a layer containing a compound represented by a formula (G1):

(G1)

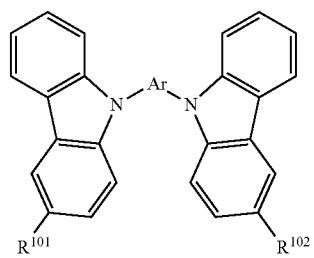

wherein Ar represents a substituted or unsubstituted phenylene group or a substituted or unsubstituted biphenyldiyl group, and wherein $R^{101}$ and $R^{102}$ each independently represent a group represented by a formula (g1):

(g1)

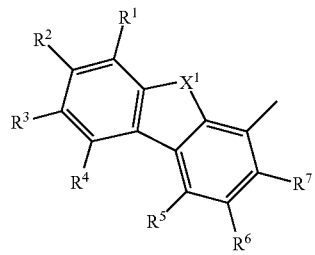

wherein $X^1$ represents sulfur or oxygen, and wherein $R^1$ to $R^7$ each independently represent any of hydrogen, an alkyl group having 1 to 4 carbon atoms, or an aryl group having 6 to 12 carbon atoms.

13. The compound according to claim 12, wherein the compound is represented by a formula (100):

(100)

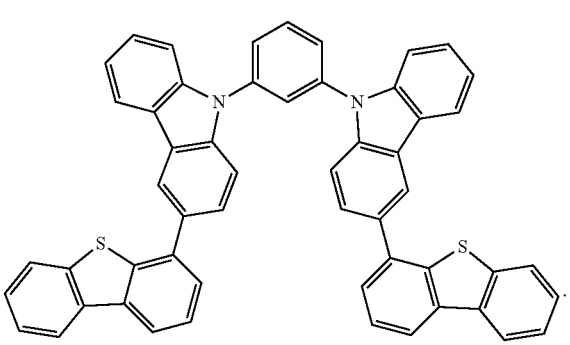

14. The compound according to claim 12, wherein the compound is represented by a formula (106):

(106)

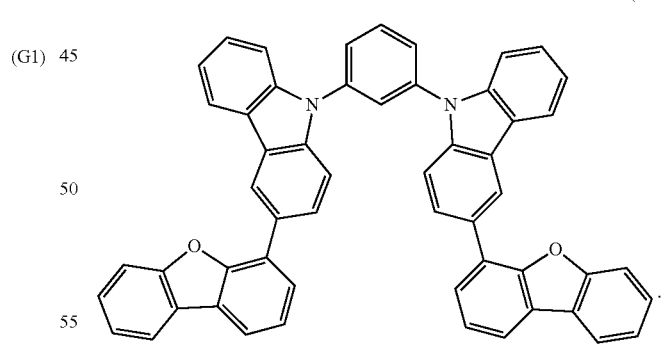

15. The compound according to claim 12, wherein $R^{101}$ and $R^{102}$ the same.

* * * * *

UNITED STATES PATENT AND TRADEMARK OFFICE
CERTIFICATE OF CORRECTION

PATENT NO.        : 8,674,114 B2                                            Page 1 of 2
APPLICATION NO.   : 13/469619
DATED             : March 18, 2014
INVENTOR(S)       : Sachiko Kawakami et al.

It is certified that error appears in the above-identified patent and that said Letters Patent is hereby corrected as shown below:

In the Specification:

Column 37, Line 38; Change "and $R^{1Oz}$ and" to --and $R^{101}$ and--.

Column 37, Line 41; Change "to $R^{2}$" to --to $R^{7}$--.

Column 41, Line 28; Change "fanned" to --formed--.

Column 42, Line 11; Change "[1,1-biphenyl]" to --[1,1'-biphenyl]--.

Column 42, Lines 60 to 61; Change "[1,1-biphenyl]" to --[1,1'-biphenyl]--.

Column 43, Line 42; Change "N-phenylamino}" to --N'-phenylamino}--.

Column 43, Line 43; Change "[N,N-bis(" to --[N,N'-bis(--.

Column 43, Line 44; Change "N,N-bis(phenyl)" to --N,N'-bis(phenyl)--.

Column 44, Line 20; Change "N,N-diphenyl]" to --N,N'-diphenyl]--.

Column 46, Line 26; Change "CzAlPA)," to --CzAlPA),--.

Column 49, Line 34; Change "511 and, a" to --511 and a--.

Column 51, Line 51; Change "switching II-T 611," to --switching TFT 611,--.

Column 59, Line 23; Change "N,N-(1,3-phenylene)" to --N,N'-(1,3-phenylene)--.

Column 60, Line 43; Change "288 inn" to --288 nm--.

Column 63, Line 40; Change "formula (I)" to --formula (i)--.

Column 63, Line 42; Change "1,6-MemFLPAPm)" to --1,6mMemFLPAPm)--.

Column 63, Line 46; Change "was fainted." to --was formed.--.

Column 63, Line 50; Change "fanning" to --forming--.

Column 63, Line 53; Change "fowling" to --forming--.

Column 67, Line 17; Change "of iridium" to --of indium--.

Column 67, Line 49; Change "fowling" to --forming--.

Signed and Sealed this
Ninth Day of September, 2014

Michelle K. Lee
*Deputy Director of the United States Patent and Trademark Office*

CERTIFICATE OF CORRECTION (continued)
U.S. Pat. No. 8,674,114 B2

Column 71, Line 41; Change "formula (Iv)" to --formula (iv)--.

Column 76, Line 59; Change "[Ir(Mptzl-mp)$_3$])" to --[Ir(Mptz1-mp)$_3$])--.

Column 76, Line 61; Change "[Ir(Mptzl-mp)$_3$])" to --[Ir(Mptz1-mp)$_3$])--.

Column 76, Line 65; Change "[Ir(Mptzl-mp)$_3$])" to --[Ir(Mptz1-mp)$_3$])--.

Column 76, Line 66; Change "[Ir(Mptzl-mp)$_3$])" to --[Ir(Mptz1-mp)$_3$])--.

Column 77, Line 3; Change "[Ir(Mptzl-mp)$_3$])" to --[Ir(Mptz1-mp)$_3$])--.

Column 77, Line 4; Change "[Ir(Mptzl-mp)$_3$])" to --[Ir(Mptz1-mp)$_3$])--.

Column 77, Line 5; Change "[Ir(Mptzl-mp)$_3$])" to --[Ir(Mptz1-mp)$_3$])--.

Column 77, Line 7; Change "[Ir(Mptzl-mp)$_3$])" to --[Ir(Mptz1-mp)$_3$])--.

Column 78, Lines 33 to 34; Change "[Ir(Mptzl-mp)$_3$]," to --[Ir(Mptz1-mp)$_3$],--.

Column 83, Line 12; Change "halfwave potential $E_{12}$" to --halfwave potential $E_{1/2}$--.

Column 83, Line 64; Change "N,N-bis[" to --N,N'-bis[--.

Column 89, Line 5; Change "[Ir(Mptzl-mp)$_3$]" to --[Ir(Mptz1-mp)$_3$]--.

Column 89, Lines 8 to 9; Change "[Ir(Mptzl-mp)3])," to --[Ir(Mptz1-mp)3]),--.

Column 89, Line 46; Change "HMptzl-mp)" to --HMptz1-mp)--.

Column 89, Line 65; Change "HMptzl-mp)" to --HMptz1-mp)--.

Column 90, Line 30; Change "[Ir(Mptzl-mp)3])" to --[Ir(Mptz1-mp)3])--.

Column 90, Line 32; Change "ligand HMptzl-mp" to --ligand HMptz1-mp--.

Column 90, Line 44; Change "complex Ir(Mptzl-mp)3" to --complex Ir(Mptz1-mp)3--.

Column 91, Line 17; Change "Thus, [Ir(Mptzl-mp)3]" to --Thus, [Ir(Mptz1-mp)3]--.

In the Claims:

Column 92, Line 64, Claim 7; Change "$R^{102}$ the same." to --$R^{102}$ are the same.--.

Column 94, Line 59, Claim 15; Change "$R^{102}$ the same." to -- $R^{102}$ are the same.--.